(12) United States Patent
Fushimi et al.

(10) Patent No.: US 7,375,113 B2
(45) Date of Patent: May 20, 2008

(54) NITROGENOUS FUSED-RING DERIVATIVES, MEDICINAL COMPOSITIONS CONTAINING THE DERIVATIVES, AND USE THEREOF AS DRUGS

(75) Inventors: Nobuhiko Fushimi, Azumino (JP); Hirotaka Teranishi, Azumino (JP); Kazuo Shimizu, Azumino (JP); Shigeru Yonekubo, Azumino (JP); Fumiaki Ito, Azumino (JP); Masayuki Isaji, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/591,757

(22) PCT Filed: Mar. 3, 2005

(86) PCT No.: PCT/JP2005/004145

§ 371 (c)(1),
(2), (4) Date: Sep. 1, 2006

(87) PCT Pub. No.: WO2005/085267

PCT Pub. Date: Sep. 15, 2005

(65) Prior Publication Data

US 2007/0191289 A1 Aug. 16, 2007

(30) Foreign Application Priority Data

Mar. 4, 2004 (JP) ................................ 2004-61426

(51) Int. Cl.
*A61K 31/44* (2006.01)
*A61K 31/405* (2006.01)
*A01N 43/38* (2006.01)
*C07D 498/02* (2006.01)
*C07D 513/02* (2006.01)

(52) U.S. Cl. ...................... 514/303; 514/415; 546/119; 548/361.1

(58) Field of Classification Search ................ 546/119; 548/361.1; 514/303, 415
See application file for complete search history.

(56) References Cited

FOREIGN PATENT DOCUMENTS

| | | | |
|---|---|---|---|
| DE | 2032171 | * | 6/1970 |
| JP | 2003-12686 A | | 1/2003 |
| WO | WO 2004/087727 A1 | | 10/2004 |
| WO | WO 2004/113359 A1 | | 12/2004 |

OTHER PUBLICATIONS

Majowicz et al., Peptides, 2003, vol. 24, pp. 1971-1976.*

Ohsumi, K. et al.; Pyrazole-*o*-Glucosides as Novel Na⁼-Glucose Cotransporter (SGLT) Inhibitors. Bioorganic & Medicinal Chemistry Letters, 2003, vol. 13, pp. 2269 to 2272.

* cited by examiner

*Primary Examiner*—Margaret D. Seaman
*Assistant Examiner*—Niloofar Rahmani
(74) *Attorney, Agent, or Firm*—Sughrue Mion, PLLC

(57) ABSTRACT

The present invention provides nitrogen-containing fused-ring derivatives represented by the following general formula, or pharmaceutically acceptable salts thereof, or prodrugs thereof, which exhibit an excellent inhibitory activity in human SGLT and are useful as agents for the prevention or treatment of a disease associated with hyperglycemia such as diabetes, postprandial hyperglycemia, impaired glucose tolerance, diabetic complications or obesity, in the formula $R^1$ represent H, an optionally substituted alkyl group, analkenyl group, etc.; $R^2$ represent H, a halogen atom or an alkyl group; $R^3$ and $R^4$ represent H, OH, a halogen atom, an optionally substituted alkyl group, etc.; Y represents CH or N; Q represents alkylene, alkenylene, etc.; ring A represents an aryl group or a heteroaryl group; G represents a group represented by the following general formula (G-1) or (G-2) (in which $E^1$ represents H, F or OH; and $E^2$ represents H, F, a methyl group, etc.), and pharmaceutical compositions comprising the same, and pharmaceutical uses thereof

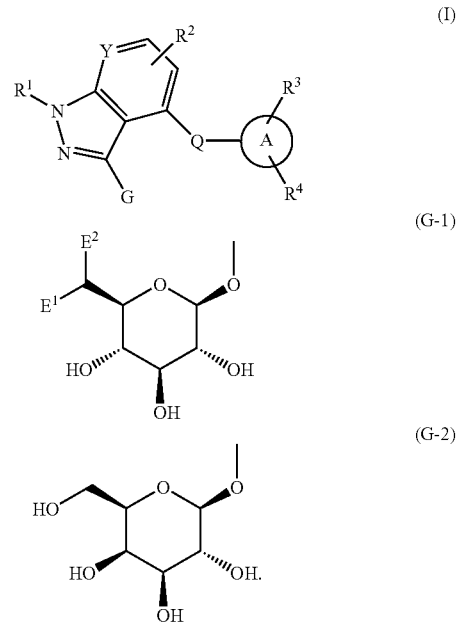

11 Claims, No Drawings

NITROGENOUS FUSED-RING DERIVATIVES, MEDICINAL COMPOSITIONS CONTAINING THE DERIVATIVES, AND USE THEREOF AS DRUGS

TECHNICAL FIELD

The present invention relates to nitrogen-containing fused-ring derivatives, pharmaceutically acceptable salts thereof or prodrugs thereof which are useful as medicaments, pharmaceutical compositions comprising the same and pharmaceutical uses thereof.

More particularly, the present invention relates to nitrogen-containing fused-ring derivatives having an inhibitory activity in human SGLT, pharmaceutically acceptable salts thereof or prodrugs thereof which are useful as agents for the prevention or treatment of a disease associated with hyperglycemia such as diabetes, impaired glucose tolerance, diabetic complications or obesity, pharmaceutical compositions comprising the same and pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. In addition, it has been confirmed by large-scale clinical trial that it is necessary to practice a long-term strict control of blood sugar level so as to prevent patients with diabetes from occurring and advancing diabetic complications by receiving treatment (for example, see the following References 1 and 2). Furthermore, many epidemiologic studies on impaired glucose tolerance and macroangiopathy show that impaired glucose tolerance as the boundary type is also a risk factor in macroangiopathy as well as diabetes. Thus, needs to improve postprandial hyperglycemia have been focused (for example, see the following Reference 3).

In recent years, development of various antidiabetic agents has been progressing with the background of a rapid increase of patients with diabetes. For example, Antidiabetic agents such as biguanides, sulfonylureas, insulin sensitivity enhancers, α-glucosidase inhibitors and the like have been employed. However, biguanides and sulfonylureas show occasionally adverse effects such as lactic acidosis and hypoglycemia, respectively. Insulin sensitivity enhancers show occasionally adverse effects such as edema, and are concerned for advancing obesity. In addition, α-glucosidase inhibitors, which delay carbohydrate digestion and absorption at the small intestine, are used to improve postprandial hyperglycemia. It has been also reported that acarbose, one of α-glucosidase inhibitors, has an effect of preventing or delaying the incidence of diabetes by applying to patients with impaired glucose tolerance (for example, see the following Reference 4). However, since α-glucosidase inhibitors do not affect elevated glucose levels by ingesting a monosaccharide of glucose (for example, see the following Reference 5), with recently changing compositions of sugars in meals, a wider range of activities inhibiting carbohydrate absorption has been desired.

In recent years, research and development of new type antidiabetic agents have been progressing, which promote urinary glucose excretion and lower blood glucose level by preventing reabsorption of excess glucose at the kidney (for example, see the following Reference 6). In addition, it is reported that SGLT2 (sodium-dependent glucose transporter 2) is present in the S1 segment of the kidney's proximal tubule and participates mainly in reabsorption of glucose filtrated through glomerular (for example, see the following Reference 7). Accordingly, inhibiting a human SGLT2activity prevents reabsorption of excess glucose at the kidney, subsequently promotes excreting excess glucose though the urine, and normalizes blood glucose level. In addition, since such agents for promoting the excretion of urinary glucose excrete excess glucose though the urine and consequently the glucose accumulation in the body is decreased, they are also expected to have a preventing or alleviating effect on obesity and a diuretic effect. Furthermore, the agents are considered to be useful for various related diseases which occur accompanying the progress of diabetes or obesity due to hyperglycemia.

Furthermore, it has been known that SGLT1, sodium-dependent glucose transporter 1, exists in the small intestine which controls carbohydrate absorption. It has been also reported that insufficiency of glucose and galactose absorption arises in patients with dysfunction due to congenital abnormalities of human SGLT1 (for example, see the following References 8-10). In addition, it has been confirmed that SGLT1 is involved in glucose and galactose absorption (for example, see the following References 11 and 12). Furthermore, it is confirmed that mRNA and protein of SGLT1 increase and absorption of glucoses are accelerated in OLETF rats and rats with streptozotocin-induced diabetic symptoms (for example, see the following References 13 and 14). Generally in patients with diabetes, carbohydrate digestion and absorption are increased. For example, it is confirmed that mRNA and protein of SGLT1 are highly increased in the human small intestine (for example, see the following Reference 15). Therefore, blocking a human SGLT1 activity inhibits absorption of carbohydrates such as glucose at the small intestine, subsequently can prevent increase of blood sugar level. Especially, it is considered that delaying glucose absorption based on the above mentioned mechanism is effective to normalize postprandial hyperglycemia.

Therefore, fast development of antidiabetic agents with novel action mechanism, which have an inhibitory activity in human SGLT, has been desired to improve or solve the above-mentioned problems.

Fused heterocyclic derivatives provided in the present invention are entirely novel compounds. It has not ever been reported that these derivatives have an inhibitory activities in SGLT1 and/or SGLT2 and inhibit absorption of glucose and galactose at the small intestine, or are useful as agents to inhibit reabsorption of excess glucose at the kidney.

Reference 1: The Diabetes Control and Complications Trial Research Group, N. Engl. J. Med., 1993.9, Vol.329, No. 14, pp. 977-986;

Reference2: UK Prospective Diabetes Study Group, Lancet, 1998.9, Vol.352, No. 9131, pp. 837-853;

Reference 3: Makoto TOMINAGA, Endocrinology & Diabetology, 2001.11, Vol.13, No. 5, pp. 534-542;

Reference 4: Jean-Louis Chiassonand5persons, Lancet, 2002.6, Vol.359, No. 9323, pp. 2072-2077;

Reference 5: Hiroyuki ODAKA and 3 persons, Journal of Japanese Society of Nutrition and Food Science, 1992, Vol.45, p. 27;

Reference 6: Luciano Rossetti and 4 persons, J. Clin. Invest., 1987.5, Vol.79, pp. 1510-1515;

Reference 7: Yoshikatsu Kanai and 4 persons, J. Clin. Invest., 1994.1, Vol.93, pp. 397-404;

Reference 8: Tadao BABA and 1 person, Supplementary volume of Nippon Rinsho, Ryoikibetsu Shokogun, 1998, No. 19, pp. 552-554;

Reference 9: Michihiro KASAHARA and 2 persons, Saishin Igaku, 1996.1, Vol.51, No. 1, pp. 84-90;

Reference 10: Tomofusa TSUCHIYA and 1 person, Nippon Rinsho, 1997.8, Vol.55, No. 8, pp. 2131-2139;

Reference 11: Yoshikatsu KANAI, Kidney and Dialysis, 1998.12, Vol.45, extra edition, pp. 232-237;

Reference 12: E. Turk and 4 persons, Nature, 1991.3, Vol.350, pp. 354-356;

Reference 13: Y. Fujita and 5 persons, Diabetologia, 1998, Vol.41, pp. 1459-1466;

Reference 14: J. Dyer and 5 persons, Biochemical Society Transactions, 1997, Vol.25, p. 479S;

Reference 15: J. Dyer and 4 persons, American Journal of Physiology, 2002.2, Vol.282, No. 2, pp.G241-G248

DISCLOSURE OF THE INVENTION

The present inventors have studied earnestly to find compounds having an inhibitory activity in human SGLT. As a result, it was found that certain nitrogen-containing fused-ring derivatives represented by the following general formula (I) show an inhibitory activity in human SGLT1 and/or SGLT2 and are excellent agents having inhibitory activity in increase of blood glucose level or lowering blood glucose level as shown below, thereby forming the basis of the present invention.

The present invention is to provide novel compounds which show an inhibitory activity in human SGLT, pharmaceutical compositions comprising the same and pharmaceutical uses thereof.

This is, the present invention relates to

[1] a nitrogen-containing fused-ring derivative represented by the following general formula (I):

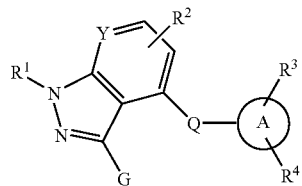

(I)

wherein $R^1$ represents a hydrogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy($C_{1-6}$ alkyl) group, a $C_{2-7}$ alkoxycarbonyl($C_{1-6}$ alkyl) group, a carboxy($C_{1-6}$ alkyl) group, a $C_{2-6}$ alkenyl group, -J-N($R^5$)-$Z^1$, -J-CON($R^5$)-$Z^1$, or any of the following substituents (a) to (d) which may have any 1 to 3 substituents selected from the following substituent group α on the ring;

(a) a $C_{3-7}$ cycloalkyl group, (b) a $C_{3-7}$ cycloalkyl($C_{1-6}$ alkyl) group, (c) a $C_{6-10}$ aryl group or (d) a $C_{6-10}$ aryl($C_{1-6}$ alkyl) group, $R^2$ represents a hydrogen atom, a halogen atom or a $C_{1-6}$ alkyl group;

$R^3$ and $R^4$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkenyl) group, a hydroxy($C_{1-6}$ alkoxy) group, a hydroxy($C_{1-6}$ alkylthio) group, a carboxy group, a carboxy($C_{1-6}$ alkyl) group, a carboxy($C_{2-6}$ alkenyl) group, a carboxy($C_{1-6}$ alkoxy) group, a carboxy($C_{1-6}$ alkylthio) group, a $C_{2-7}$ alkoxycarbonyl group, a $C_{2-7}$ alkoxycarbonyl($C_{1-6}$ alkyl) group, a $C_{2-7}$ alkoxycarbonyl($C_{2-6}$ alkenyl) group, a $C_{2-7}$ alkoxycarbonyl($C_{1-6}$alkoxy) group, a $C_{2-7}$ alkoxycarbonyl($C_{1-6}$ alkylthio) group, a $C_{1-6}$ alkylsulfinyl group, a $C_{1-6}$ alkylsulfonyl group, —U—V—W—N($R^6$)-$Z^2$, or any of the following substituents (i) to (xxviii) which may have any 1 to 3 substituents selected from the following substituent group α on the ring;

(i) a $C_{6-10}$ aryl group, (ii) $C_{6-10}$ aryl-O—, (iii) $C_{6-10}$ aryl-S—, (iv) a $C_{6-10}$ aryl ($C_{1-6}$ alkyl) group, (v) a $C_{6-10}$ aryl ($C_{1-6}$ alkoxy) group, (vi) a $C_{6-10}$ aryl($C_{1-6}$ alkylthio) group, (vii) a heteroaryl group, (viii) heteroaryl-O—, (ix) heteroaryl-S—, (x) a heteroaryl($C_{1-6}$ alkyl) group, (xi) a heteroaryl($C_{1-6}$ alkoxy) group, (xii) a heteroaryl($C_{1-6}$alkylthio) group, (xiii) a $C_{3-7}$ cycloalkyl group, (xiv) $C_{3-7}$ cycloalkyl-O—, (xv) $C_{3-7}$ cycloalkyl-S—, (xvi) a $C_{3-7}$ cycloalkyl($C_{1-6}$ alkyl) group, (xvii) a $C_{3-7}$ cycloalkyl($C_{1-6}$ alkoxy) group, (xviii) a $C_{3-7}$ cycloalkyl($C_{1-6}$ alkylthio) group, (xix) a heterocycloalkyl group, (xx) heterocycloalkyl-O—, (xxi) heterocycloalkyl-S—, (xxii) a heterocycloalkyl($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group or (xxvii) an aromatic cyclic amino($C_{1-6}$ alkoxy) group or (xxviii) an aromatic cyclic amino($C_{1-6}$ alkylthio) group, J represents a $C_{1-6}$ alkylene group which may have a hydroxy group, or a $C_{2-6}$ alkenylene group;

U represents —O—, —S— or a single bond and with the proviso that at least one of V and W is not a single bond when U is —O— or —S—);

V represents a $C_{1-6}$ alkylene group which may have a hydroxy group, a $C_{2-6}$ alkenylene group or a single bond;

W represents —CO—, —SO$_2$—, —C(=NH)— or a single bond;

$Z^1$ and $Z^2$ independently represent a hydrogen atom, a $C_{2-7}$ alkoxycarbonyl group, a $C_{6-10}$ aryl($C_{2-7}$ alkoxycarbonyl) group, a formyl group, —$R^A$, —COR$^B$, —SO$_2$R$^B$, —CON($R^C$)$R^D$, —CSN($R^C$)$R^D$, —SO$_2$NHR or —C(=NR$^E$)N($R^F$)$R^G$;

$R^5$, $R^6$, $R^A$, $R^C$ and $R^D$ independently represent a hydrogen atom, a $C_{1-6}$ alkyl group which may have any 1 to 5 substituents selected from the following substituent group β or any of the following substituents (xxix) to (xxxii) which may have any 1 to 3 substituents selected from the following substituent group α;

(xxix) a $C_{6-10}$aryl group, (xxx) a heteroaryl group, (xxxi) a $C_{3-7}$ cycloalkyl group or (xxxii) a heterocycloalkyl group or both of $Z^1$ and $R^5$ or both of $Z^2$ and $R^6$ bind together with the neighboring nitrogen atom to form an aliphatic cyclic amino group which may have any 1 to 3 substituents selected from the following substituent group α;

or $R^C$ and $R^D$ bind together with the neighboring nitrogen atom to form an aliphatic cyclic amino group which may have any 1 to 3 substituents selected from the following substituent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have any 1 to 5 substituents selected from the following substituent group β or any of the following substituents (xxxiii) to (xxxvi) which may have any 1 to 3 substituents selected from the following substituent group α;

(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl($C_{2-7}$ alkoxycarbonyl) group, a nitro group, a $C_{1-6}$ alkylsulfonyl group, a sulfamoyl group, a carbamimidoyl group or a $C_{1-6}$ alkyl group which may have any 1 to 5 substituents selected from the following substituent group β;

or $R^E$ and $R^F$ bind together to form an ethylene group;

or $R^F$ and $R^G$ bind together with the neighboring nitrogen atom to form an aliphatic cyclic amino group which may have a substituent selected from the following substituent group α;

Y represents CH or N;

Q represents —$C_{1-6}$ alkylene-, —$C_{2-6}$ alkenylene-, —$C_{2-6}$ alkynylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$ alkylene-S—$C_{1-6}$ alkylene-, —CON($R^7$)—, —N($R^7$)CO—, —$C_{1-6}$ alkylene-CON($R^7$)— or —CON($R^7$)—$C_{1-6}$ alkylene-;

$R^7$ represents a hydrogen atom or a $C_{1-6}$ alkyl group; ring A represents a $C_{6-10}$ aryl group or a heteroaryl group; represents a group represented by a formula:

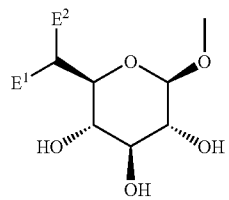

(G-1)

or a formula:

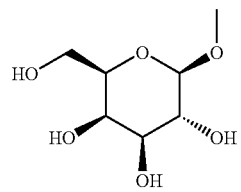

(G-2)

$E^1$ represents a hydrogen atom, a fluorine atom or a hydroxy group;

$E^2$ represents a hydrogen atom, a fluorine atom, a methyl group or a hydroxymethyl group;

[substituent group α]

a halogen atom, a hydroxy group, an amino group, a $C_{1-6}$ alkyl group, a $C_{1-6}$alkoxy group, a halo($C_{1-6}$alkyl) group, a halo($C_{1-6}$ alkoxy)group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$alkylsulfonylamino($C_{1-6}$alkyl) group, a carboxy group, a $C_{2-7}$ alkoxycarbonyl group, a sulfamoyl group and —CON($R^H$)$R^I$

[substituent group β]

a halogen atom, a hydroxy group, an amino group, a $C_{1-6}$ alkoxy group, a $C_{1-6}$ alkylthio group, a halo ($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$alkylthio) group, a mono or di($C_{1-6}$alkyl)amino group, a mono or di[hydroxy($C_{1-6}$ alkyl)]amino group, an ureido group, a sulfamide group, a mono or di($C_{1-6}$ alkyl) ureido group, a mono or di[hydroxy ($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino ($C_{2-7}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group, —CON($R^H$)$R^I$, and any of the following substituents (xxxvii) to (xxxxviii) which may have any 1 to 3 substituents selected from the above substituent group α on the ring;

(xxxvii) a $C_{6-10}$ aryl group, (xxxviii) $C_{6-10}$ aryl-O—, (xxxix) a $C_{6-10}$ aryl ($C_{1-6}$ alkoxy) group, (xxxx) a $C_{6-10}$ aryl ($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloalkyl-O—, (xxxxv) a heterocycloalkyl group, (xxxxvi) heterocycloalkyl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have any 1 to 3 substituents selected from the following substituent group γ;

or both of $R^H$ and $R^I$ bind together with the neighboring nitrogen atom to form an aliphatic cyclic amino group which may have any 1 to 3 substituents selected from the following substituent group δ;

[substituent group γ]

a halogen atom, a hydroxy group, an amino group, a $C_{1-6}$ alkoxy group, a halo ($C_{1-6}$ alkoxy) group, a hydroxy($C_{1-6}$ alkoxy) group, an amino($C_{1-6}$ alkoxy) group, a mono or di($C_{1-6}$ alkyl)amino group, a mono or di[hydroxy($C_{1-6}$ alkyl)] amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino ($C_{2-7}$ acylamino) group, a $C_{1-6}$ alkylsulfonyl group, a $C_{1-6}$ alkylsulfonylamino group, a carbamoyl($C_{1-6}$ alkylsulfonylamino) group, a carboxy group, a $C_{2-7}$ alkoxycarbonyl group and —CON($R^J$)$R^K$

[substituent group δ]

a halogen atom, a hydroxy group, an amino group, a $C_{1-6}$ alkyl group, a $C_{1-6}$alkoxy group, a halo($C_{1-6}$alkyl) group, a halo($C_{1-6}$ alkoxy) group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino ($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di ($C_{1-6}$alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl)amino group, a $C_{1-6}$ alkyl group, a hydroxy($C_{1-6}$ alkyl) group, a $C_{2-7}$ alkoxycarbonyl group, a $C_{2-7}$ alkoxycarbonyl($C_{1-6}$ alkyl) group and a carbamoyl group, or a pharmaceutically acceptable salt thereof, or a prodrug thereof;

[2] a nitrogen-containing fused-ring derivative as described in the above [1], wherein Q represents an ethylene group, or a pharmaceutically acceptable salt thereof, or a prodrug thereof;

[3] a nitrogen-containing fused-ring derivative as described in the above [1], wherein Q represents a methylene group, or a pharmaceutically acceptable salt thereof, or a prodrug thereof;

[4] a nitrogen-containing fused-ring derivative as described in any one of the above [1] to [3], wherein G represents a group represented by the formula:

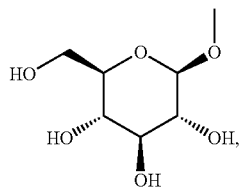

or a pharmaceutically acceptable salt thereof, or a prodrug thereof;

[5] a nitrogen-containing fused-ring derivative as described in any one of the above [1] to [4], wherein ring A represents a group derived from a benzene ring, a pyridine ring, a pyrimidine ring, a pyrazine ring or a pyridazine ring, or a pharmaceutically acceptable salt thereof, or a prodrug thereof;

[6] a nitrogen-containing fused-ring derivative as described in the above [5], where in the ring A represents a benzene ring, or a pharmaceutically acceptable salt thereof, or a prodrug thereof;

[7] a nitrogen-containing fused-ring derivative as described in the above [5], wherein the ring A represents a pyridine ring, or a pharmaceutically acceptable salt thereof, or a prodrug thereof;

[8] a nitrogen-containing fused-ring derivative as described in the above [5], wherein $R^3$ represents a hydrogen atom, a halogen atom or a $C_{1-6}$ alkyl group; $R^4$ represents a hydrogen atom, a hydroxy group, a halogen atom, a $C_{1-6}$ alkyl group, a $C_{1-6}$ alkoxy group, a $C_{1-6}$ alkylthio group, a hydroxy($C_{1-6}$ alkyl) group, a $C_{3-7}$ cycloalkyl group, or —$U^a$—$V^a$—$W^a$—N($R^{6a}$)—$Z^{2a}$—; $U^a$ represents —O— or a single bond and with the proviso that at least one of $V^a$ and $W^a$ does not represents a single bond when $U^a$ represents —O—; $V^a$ represents a $C_{1-6}$ alkylene group, a $C_{2-6}$ alkenylene group or a single bond; $W^a$ represents —CO— or a single bond; $Z^{2a}$ represents a hydrogen atom, —$R^{Aa}$, —CON($R^c$)$R^D$, or —C(=NR$^E$)N(R$^F$)R$^G$; $R^{6a}$ and $R^{Aa}$ independently represent a hydrogen atom, or a $C_{1-6}$ alkyl group which may have any 1 to 5 groups selected from substituent group β; $R^C$, $R^D$, $R^E$, $R^F$, $R^G$ and substituent group β have the same meanings as defined above, or a pharmaceutically acceptable salt thereof, or a prodrug thereof;

[9] a nitrogen-containing fused-ring derivative as described in the above [5] or [8], wherein $R^1$ represents a hydrogen atom, a $C_{1-6}$ alkyl group, a hydroxy($C_{1-6}$ alkyl) group, or —J—CONH$_2$; $J^a$ represents a $C_{1-6}$ alkylene group; $R^2$ represents a hydrogen atom, or a pharmaceutically acceptable salt thereof, or a prodrug thereof;

[10] a pharmaceutical composition comprising as an active ingredient a nitrogen-containing fused-ring derivative as described in any one of the above [1] to [9], or a pharmaceutically acceptable salt thereof, or a prodrug thereof;

[11] a human SGLT inhibitor comprising as an active ingredient a nitrogen-containing fused-ring derivative as described in anyone of the above [1] to [9], or a pharmaceutically acceptable salt thereof, or a prodrug thereof;

[12] a human SGLT inhibitor as described in the above [11], wherein the SGLT is SGLT1 and/or SGLT2;

[13] a human SGLT inhibitor as described in the above [11], which is an agent for the inhibition of postprandial hyperglycemia;

[14] a human SGLT inhibitor as described in the above [11], which is an agent for the prevention or treatment of a disease associated with hyperglycemia;

[15] a human SGLT inhibitor as described in the above [14], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[16] ahuman SGLT inhibitor as described in the above [11], which is an agent for the inhibition of advancing impaired glucose tolerance into diabetes in a subject;

[17] a pharmaceutical composition as described in the above [10], wherein the dosage form is sustained release formulation;

[18] a human SGLT inhibitor as described in the above [11], wherein the dosage form is sustained release formulation;

[19] a method for the inhibition of postprandial hyperglycemia, which comprises administering an effective amount of a nitrogen-containing fused-ring derivative as described in any one of the above [1] to [9], or a pharmaceutically acceptable salt thereof, or a prodrug thereof;

[20] a method for the prevention or treatment of a disease associated with hyperglycemia, which comprises administering an effective amount of a nitrogen-containing fused-ring derivative as described in any one of the above [1] to [9], or a pharmaceutically acceptable salt there of, or a prodrug there of;

[21] a method for the prevention or treatment as described in the above [20], wherein the disease associated with hyperglycemia is a disease selected from the group consisting of diabetes, impaired glucose tolerance, diabetic complications, obesity, hyperinsulinemia, hyperlipidemia, hyper-cholesterolemia, hypertriglyceridemia, lipid metabolism disorder, atherosclerosis, hypertension, congestive heart failure, edema, hyperuricemia and gout;

[22] a method for the inhibition of advancing impaired glucose tolerance into diabetes in a subject, which comprises administering an effective amount of a nitrogen-containing fused-ring derivative as described in any one of the above [1] to [9], or a pharmaceutically acceptable salt thereof, or a prodrug thereof;

[23] a use of a nitrogen-containing fused-ring derivative as described in any one of the above [1] to [9], or a pharmaceutically acceptable salt thereof, or a prodrug thereof for the manufacture of a pharmaceutical composition for the inhibition of postprandial hyperglycemia;

[24] a use of a nitrogen-containing fused-ring derivative as described in any one of the above [1] to [9], or a pharmaceutically acceptable salt thereof, or a prodrug thereof for the manufacture of a pharmaceutical composition for the prevention or treatment of a disease associated with hyperglycemia;

[25] a use as described in the above [24], wherein the disease associated with hyperglycemia is a disease selected from the group consisting of diabetes, impaired glucose tolerance, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[26] a use of a nitrogen-containing fused-ring derivative as described in any one of the above [1] to [9], or a pharmaceutically acceptable salt thereof, or a prodrug thereof for the manufacture of a pharmaceutical composition for the inhibition of advancing impaired glucose tolerance into diabetes in a subject;

[27] a pharmaceutical composition as described in the above [10], which comprises combination with at least one member selected from the group consisting of an insulin sensitivity enhancer, a glucoseabsorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[28] a human SGLT inhibitor as described in the above [11], which comprises combination with at least one member selected from the group consisting of an insulin sensitivity enhancer, aglucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[29] a method for the inhibition of postprandial hyperglycemia as described in the above [19], which comprises administering in combination with at least one member selected from the group consisting of an insulin sensitivity enhancer, a glucose absorption inhibitor, abiguanide, aninsulinsecretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, anendothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[30] a method for the prevention or treatment of a disease associated with hyperglycemia as described in the above [20], which comprises administering in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinicacidderivative, abileacid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[31] a method for the inhibition of advancing impaired glucose tolerance into diabetes in a subject as described in the above [22], which comprises administering in combination with at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinicacidderivative, abileacid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, anangiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[32] a use of (A) a nitrogen-containing fused-ring derivative as described in any one of the above [1] to [9], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinicacidderivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the inhibition of postprandial hyperglycemia;

[33] a use of (A) a nitrogen-containing fused-ring derivative as described in any one of the above [1] to [9], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, anamylinanalogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinicacidderivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia;

[34] a use of (A) a nitrogen-containing fused-ring derivative as described in any one of the above [1] to [9], or a pharmaceutically acceptable salt thereof, or a prodrug thereof and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the inhibition of advancing impaired glucose tolerance into diabetes in a subject; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{1-6}$ alkylene group" or "—$C_{1-6}$ alkylene-" means a straight-chained or branched alkylene group having 1 to 6carbon atoms such as a methylene group, an ethylene group, a trimethylene group, a tetramethylene group, a propylene group, a 1,1-dimethylethylene group or the like; and the term "$C_{1-4}$ alkylene group" or "—$C_{1-4}$ alkylene-" means a straight-chained or branched alkylene group having 1 to 4 carbon atoms such as a methylene group, an ethylene group, a trimethylene group, a tetramethylene group, a propylene group, a 1,1-dimethylethylene group or the like. The term "hydroxy($C_{1-6}$ alkyl) group" means the above $C_{1-6}$ alkyl group substituted by a hydroxy group; the term "dihydroxy($C_{1-6}$ alkyl) group" means the above $C_{1-6}$ alkyl group substituted by two hydroxy groups such as a 2,3-dihydroxypropyl group, a 1,3-dihydroxy-2-propyl group or the like; the term "amino ($C_{1-6}$ alkyl) group" means the above $C_{1-6}$ alkyl group substituted by an amino group such as an aminomethyl group, a 2-aminoethyl group or the like; and the term "carboxy($C_{1-6}$ alkyl) group" means the above $C_{1-6}$ alkyl group substituted by a carboxy group.

The term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "hydroxy ($C_{1-6}$ alkoxy) group" means the above $C_{1-6}$ alkoxy group substituted by a hydroxy group; the term "carboxy($C_{1-6}$ alkoxy) group" means the above $C_{1-6}$ alkoxy group substituted by a carboxy group; the term "amino($C_{1-6}$ alkoxy) group" means the above $C_{1-6}$ alkoxy group substituted by an amino group; and the term "alkoxy($C_{1-6}$ alkyl) group" means the above $C_{1-6}$ alkyl group substituted by the above $C_{1-6}$ alkoxy group. The term "$C_{1-6}$ alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like; the term "hydroxy($C_{1-6}$ alkylthio) group" means the above $C_{1-6}$ alkylthio group substituted by a hydroxy group; the term "carboxy($C_{1-6}$ alkylthio) group" means the above $C_{1-6}$ alkylthio group substituted by a carboxy group; and the term "amino ($C_{1-6}$ alkylthio) group" means the above $C_{1-6}$ alkylthio group substituted by an amino group.

The term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkenylene group" or "-$C_{2-6}$ alkenylene-" means a straight-chained or branched alkenylene group having 2 to 6 carbon atoms such as a vinylene group, a propenylene group or the like; the term "$C_{2-4}$ alkenylene group" means a straight-chained or branched alkenylene group having 2 to 4 carbon atoms such as a vinylene group, a propenylene group or the like; the term "hydroxy($C_{2-6}$ alkenyl) group" means the above $C_{2-6}$ alkenyl group substituted by a hydroxy group; the term "carboxy($C_{2-6}$ alkenyl) group" means the above $C_{2-6}$ alkenyl group substituted by a carboxy group; the term "$C_{2-6}$ alkenyloxy group" means a straight-chained or branched alkenyloxy group having 2 to 6 carbon atoms such as a vinyloxy group, an allyloxy group, a 1-propenyloxy group, an isopropenyloxy group, a 1-butenyloxy group, a 2-butenyloxy group, a 2-methylallyloxy group or the like; the term "$C_{2-6}$ alkenylthio group" means a straight-chained or branched alkenylthio group having 2 to 6 carbon atoms such as a vinylthio group, an allylthio group, a 1-propenylthio group, an isopropenylthio group, a 1-butenylthio group, a 2-butenylthio group, a 2-methylallylthio group or the like; the term "$C_{2-6}$ alkynyl group" means a straight-chained or branched alkynyl group having 2 to 6 carbon atoms such as an ethynyl group, a 2-propynyl group or the like; and the term "—$C_{2-6}$ alkynyl-" means a straight-chained or branched alkynylene group having 2 to 6 carbon atoms such as an ethynylene group, a propynylene group or the like.

The term "mono or di($C_{1-6}$ alkyl)amino group" means an amino group mono-substituted by the above $C_{1-6}$ alkyl group or di-substituted by the same or different $C_{1-6}$ alkyl groups as defined above; the term "mono or di[hydroxy($C_{1-6}$ alkyl)] amino group" means an amino group mono-substituted by the above hydroxy($C_{1-6}$ alkyl) group or di-substituted by any of the above hydroxy($C_{1-6}$ alkyl) groups; the term "mono or di($C_{1-6}$ alkyl)ureido group" means an ureido group mono-substituted by the above $C_{1-6}$ alkyl group or di-substituted by any of the above $C_{1-6}$ alkyl groups; the term "mono or di[hydroxy($C_{1-6}$ alkyl)]ureido group" means an ureido group mono-substituted by the above hydroxy($C_{1-6}$ alkyl) group or di-substituted by any of the above hydroxy($C_{1-6}$ alkyl) groups; the term "mono or di($C_{1-6}$ alkyl) sulfamide group" means a sulfamide group mono-substituted by the above $C_{1-6}$ alkyl group or di-substituted by any of the above $C_{1-6}$ alkyl groups; the term "mono or di[hydroxy($C_{1-6}$ alkyl)] sulfamide group" means a sulfamide group mono-substituted by the above hydroxy($C_{1-6}$ alkyl) group or di-substituted by any of the above hydroxy($C_{1-6}$ alkyl) groups; the term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; the term "$C_{2-7}$ acylamino group" means an amino group substituted by the above $C_{2-7}$ acyl group; and the term "amino ($C_{2-7}$ acylamino) group" means the above $C_{2-7}$ acylamino group substituted by an amino group, such as a 2-aminoacetylamino group, a 3-aminopropionylamino group or the like. The term "$C_{1-6}$ alkyl-sulfinyl group" means a straight-chained or branched alkyl-sulfinyl group having 1 to 6 carbon atoms such as a methylsulfinyl group, an ethylsulfinyl group or the like; the term "$C_{1-6}$ alkylsulfonyl group" means a straight-chained or branched alkylsulfonyl group having 1 to 6 carbon atoms such as a methanesulfonyl group, an ethanesulfonyl group or the like; the term "$C_{1-6}$ alkyl-sulfonylamino group" means an amino group substituted by the above $C_{1-6}$ alkylsulfonyl group; the term "carbamoyl($C_{1-6}$ alkyl-sulfonylamino) group" means the above $C_{1-6}$ alkylsulfonylamino group substituted by a carbamoyl group, such as a carbamoylmethanesulfonylamino group or the like; and the term "$C_{1-6}$ alkylsulfonylamino($C_{1-6}$ alkyl) group" means the above $C_{1-6}$ alkyl group substituted by the above $C_{1-6}$ alkylsulfonylamino group.

The term "halogen atom" means a fluorine atom, a chlorine atom, a bromine atom or an iodine atom; the term "halo($C_{1-6}$alkyl) group" means the above $C_{1-6}$ alkyl group substituted by any 1 to 3 halogen atoms as defined above; the term "halo ($C_{1-6}$ alkoxy) group" means the above $C_{1-6}$ alkoxy group substituted by any 1 to 3 halogen atoms as defined above; and the term "halo($C_{1-6}$ alkylthio) group" means the above $C_{1-6}$ alkylthio group substituted by any 1 to 3 halogen atoms as defined above. The term "$C_{2-7}$ alkoxycarbonyl group" means a straight-chained or branched alkoxycarbonyl group having 2 to 7 carbon atoms such as a methoxycarbonyl group, an ethoxycarbonyl group, a propoxy-carbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; the term "$C_{2-7}$ alkoxycarbonyl($C_{1-6}$ alkyl) group" means the above $C_{1-6}$ alkyl group substituted by the above $C_{2-7}$ alkoxycarbonyl group; the term "$C_{2-7}$alkoxycarbonyl($C_{1-6}$alkoxy) group" means the above $C_{1-6}$alkoxy group substituted by the above $C_{2-7}$ alkoxycarbonyl group; the term "$C_{2-7}$ alkoxycarbonyl ($C_{1-6}$ alkylthio) group" means the above $C_{1-6}$ alkylthio group substituted by the above $C_{2-7}$ alkoxycarbonyl group; and the term "$C_{2-7}$ alkoxycarbonyl($C_{2-6}$ alkenyl) group" means the above $C_{2-6}$ alkenyl group substituted by the above $C_{2-7}$ alkoxycarbonyl group.

The term "$C_{3-7}$ cycloalkyl group" or "$C_{3-7}$ cycloalkyl-" means a cyclopropyl group, a cyclobutyl group, a cyclopentyl group, a cyclohexyl group or a cycloheptyl group; the term "$C_{3-7}$ cycloalkyl($C_{1-6}$ alkyl) group" means the above $C_{1-6}$ alkyl group substituted by the above $C_{3-7}$ cycloalkyl group; the term "$C_{3-7}$ cycloalkyl($C_{1-6}$ alkoxy) group" means the above $C_{1-6}$ alkoxy group substituted by the above $C_{3-7}$ cycloalkyl group; and the term "$C_{3-7}$ cycloalkyl($C_{1-6}$ alkylthio) group" means the above $C_{1-6}$ alkylthio group substituted by the above $C_{3-7}$ cycloalkyl group. The term "heterocycloalkyl group" or "heterocycloalkyl-" means a 3 to 7-membered aliphatic heterocyclic group containing any 1 or 2 hetero atoms in the ring other than the binding position selected from an oxygen atom, a sulfur atom and a nitrogen atom, which is derived from morpholine, thiomorpholine, tetrahydrofuran, tetrahydropyran, aziridine, azetidine, pyrrolidine, imidazolidine, oxazoline, piperidine, piperazine, pyrazolidine, pyrroline, imidazoline or the like, or a 5 or 6-membered aliphatic heterocyclic group containing any 1 or 2 hetero atoms in the ring other than the binding position selected from an oxygen atom, a sulfur atom and a nitrogen atom, fused with a 6-membered ring which is derived from indoline, isoindoline, tetrahydroindoline, tetrahydroisoindoline, hexahydroindoline, hexahydroisoindoline or the like. The term "heterocycloalkyl ($C_{1-6}$ alkyl) group" means the above $C_{1-6}$ alkyl group substituted by the above heterocycloalkyl group; the term "heterocycloalkyl ($C_{1-6}$alkoxy) group" means the above $C_{1-6}$ alkoxy group substituted by the above heterocycloalkyl group; and the term "heterocycloalkyl ($C_{1-6}$ alkylthio) group" means the above $C_{1-6}$ alkylthio group substituted by the above heterocycloalkyl group.

The term "$C_{6-10}$ aryl group" or "$C_{6-10}$ aryl-" means an aromatic cyclic hydrocarbon group having 6 or 10 carbon atoms such as a phenyl group, a naphthyl group or the like; the term "$C_{6-10}$ aryl($C_{1-6}$ alkyl) group" means the above $C_{1-6}$ alkyl group substituted by the above $C_{6-10}$ aryl group; the term "$C_{6-10}$ aryl($C_{1-6}$ alkoxy) group" means the above $C_{1-6}$ alkoxy group substituted by the above $C_{6-10}$ aryl group; and the term "$C_{6-10}$ aryl ($C_{1-6}$ alkylthio) group" means the above $C_{1-6}$ alkylthio group substituted by the above $C_{6-10}$ aryl group. The term "$C_{6-10}$ arylsulfonylamino group" means a sulfonylamino group having the above $C_{6-10}$ aryl group, such as a benzenesulfonylamino group or the like; the term "$C_{6-10}$ aryl ($C_{2-7}$ alkoxycarbonyl) group" means the above $C_{2-7}$ alkoxycarbonyl group substituted by the above $C_{6-10}$ aryl group; and the term "heteroaryl group" or "heteroaryl-" means a 5 or 6-membered a romatic heterocyclic group containing any 1 to 4 hetero atoms in the ring other than the binding position selected from an oxygen atom, a sulfur atom and a nitrogen atom, which is derived from thiazole, oxazole, isothiazole, isooxazole, pyridine, pyrimidine, pyrazine, pyridazine, pyrrole, thiophene, imidazole, pyrazole, oxadiazole, thiodiazole, tetrazole, furazan or the like, or a 5 or 6-membered aromatic heterocyclic group containing any 1 to 4 hetero atoms in the ring other than the binding position selected from an oxygen atom, a sulfur atom and a nitrogen atom fused with a 6-membered aromatic ring, which is derived from indole, isoindole, benzofuran, isobenzofuran, benzothiophene, benzooxazole, benzothiazole, indazole, benzoimidazole, quinoline, isoquinoline, phthalazine, quinoxaline, quinazoline, cinnoline, indolizine, naphthyridine, pteridine or the like. The term "heteroaryl ($C_{1-6}$ alkyl) group" means the above $C_{1-6}$ alkyl group substituted by the above heteroaryl group; the term "heteroaryl ($C_{1-6}$ alkoxy) group" means the above $C_{1-6}$ alkoxy group substituted by the above heteroaryl group; and the term "heteroaryl ($C_{1-6}$ alkylthio) group" means the above $C_{1-6}$ alkylthio group substituted by the above heteroaryl group.

The term "aliphatic cyclic amino group" means a 5 or 6-membered aliphatic cyclic amino group which may contain one hetero atom in the ring other than the nitrogen atom at the binding position selected froman oxygen atom, a sulfur atomand nitrogen atom, such as a morpholino group, a thiomorpholino group, a 1-aziridinyl group, a 1-azetidinyl group, a 1-pyrrolidinylgroup, a piperidino group, a 1-imidazolidinyl group, a 1-piperazinyl group, a pyrazolidinyl group or the like; the term "aromatic cyclic amino group" means a 5-membered aromatic cyclic amino group which may contain 1 to 3 nitrogen atoms other than the nitrogen atom at the binding position, such as a 1-imidazolyl group, a 1-pyrrolyl group, a pyrazolyl group, a 1-tetrazolyl group or the like; the term "aromatic cyclic amino ($C_{1-6}$ alkyl) group" means the above $C_{1-6}$ alkyl group substituted by the above aromatic cyclic amino group; the term "aromatic cyclic amino ($C_{1-6}$ alkoxy) group" means the above $C_{1-6}$ alkoxy group substituted by the above aromatic cyclic amino group; and the term "aromatic cyclic amino ($C_{1-6}$ alkylthio) group" means the above $C_{1-6}$ alkylthio group substituted by the above aromatic cyclic amino group.

The term "hydroxy-protective group" means a hydroxy-protective group used in general organic synthesis such as a methyl group, a benzyl group, a methoxymethyl group, an acetyl group, a pivaloyl group, a benzoyl group, a tert-butyldimethylsilyl group, a tert-butyldiphenylsilyl group, an allyl group or the like; the term "amino-protective group" means an amino-protective group used in general organic synthesis such as a benzyloxycarbonyl group, a tert-butoxycarbonyl group, a benzyl group, an acetyl group, a trifluoroacetyl group or the like; and the term "carboxy-protective group" means a carboxy-protective group used in general organic synthesis such as a methyl group, an ethyl group, a benzyl group, a tert-butyldimethylsilyl group, an allyl group or the like. In addition, in the substituent Q, the left-hand bond means a bond bound to a nitrogen-containing fused ring and the right-hand bond means a bond bound to a ring A.

The compounds represented by the above general formula (I) of the present invention can be prepared according to the following procedures or analogous procedures thereof, or other procedures described in literatures or analogous procedures thereof.

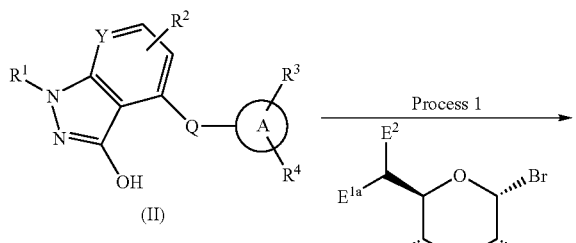

(II)

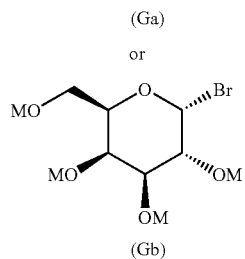

(Ga)

or

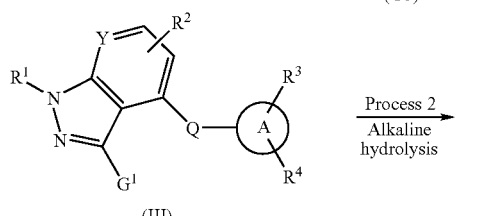

(Gb)

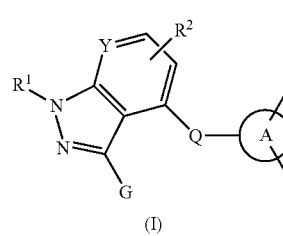

(III)

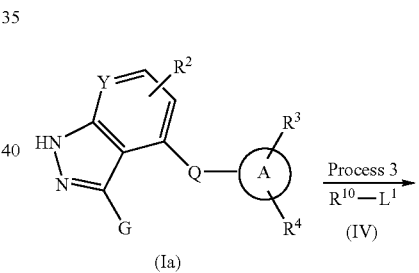

(I)

In the formula, $G^1$ represents the above G wherein a hydroxy group is protected by M; M represents a hydroxy-protective group such as an acetyl group, a pivaloyl group, a benzoyl group or the like; $E^{1a}$ represents a hydrogen atom, a fluorine atom or a hydroxy group protected by M; $E^{2a}$ represents a hydrogen atom, a fluorine atom, a methyl group or a hydroxymethyl group protected by M; and $R^1$ to $R^4$, G, Q, Y and ring A have the same meanings as defined above and with the proviso that in the case that there are a hydroxy group, an amino group and/or a carboxy group in each compound, a compound having a protective group can be suitably used.

Process 1

A glycosidated compound represented by the above general formula (III) can be prepared by subjecting a compound represented by the above general formula (II) to glycosidation using a sugar donor represented by the above general formula (Ga) or (Gb) such as acetobromo-α-D-glucose, acetobromo-α-D-galactose, 2,3,4,6-tetra-O-pivaloyl-α-D-glucopyranosyl bromide, 2,3,4,6-tetra-O-pivaloyl-α-D-galactopyranosyl bromide, 2,3,4,6-tetra-O-benzoyl-α-D-glucopyranosyl bromide, 2,3,4,6-tetra-O-benzoyl-α-D-galactopyranosyl bromide or the like in the presence of a silver salt such as silver carbonate, silver oxide or the like or a base such as sodium carbonate, potassium carbonate, cesium carbonate, sodium hydroxide, potassium hydroxide, sodium hydride or the like in the presence or absence of a phase transfer catalyst such as benzyltri(n-butyl)ammonium chloride, benzyltri(n-butyl)-ammonium bromide, tetra(n-butyl)ammonium hydrogen sulfate or the like in an inert solvent. As the solvent used, for example, tetrahydrofuran, 1,2-dimethoxyethane, N,N-dimethylformamide, acetonitrile, dichloromethane, toluene, benzotrifluoride, water, a mixed solvent thereof and the like can be illustrated. The reaction temperature is usually from room temperature to reflux temperature, and the reaction time is usually from 1 hour to 3 days, varying based on a used starting material, solvent and reaction temperature.

Process 2

A compound represented by the above general formula (I) of the present invention can be prepared by subjecting a glycosidated compound represented by the above general formula (III) to alkaline hydrolysis to remove a protected group. As the solvent used, for example, water, methanol, ethanol, tetrahydrofuran, a mixed solvent thereof and the like can be illustrated. As a basic substance, for example, sodium hydroxide, lithiumhydroxide, sodiummethoxide, sodiumethoxide or the like can be used. The reaction temperature is usually from 0° C. to reflux temperature, and the reaction time is usually from 30 minutes to 1 day, varying based on a used starting material, solvent and reaction temperature.

Of the compounds represented by the above general formula (I) of the present invention, a compound wherein $R^1$ represents a group other than a hydrogen atom can be also prepared according to the following process 3 using the following compound (Ia) which can be prepared by the above method:

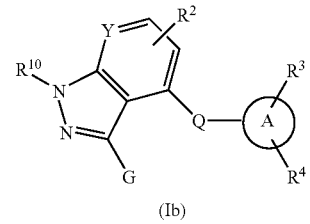

(Ia)

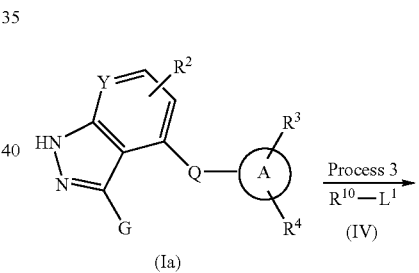

(Ib)

In the formula, $R^{10}$ represents $R^1$ except for a hydrogen atom; $L^1$ represents a leaving group such as a bromine atom, an iodine atom, a mesyloxy group, a tosyloxy group or the like; $R^2$ to $R^4$, G, Q, Y and ring A have the same meanings as defined above.

Process 3

A compound represented by the above general formula (Ib) can be prepared by subjecting a compound represented by the above general formula (Ia) to condensation with a compound represented by the above general formula (IV) in the presence of a base such as potassium carbonate, cesium carbonate, sodium hydride or the like in the presence or absence of sodium iodide in an inert solvent. As the solvent used, for example, acetone, N,N-dimethylformamide, tetrahydrofuran, a mixed solvent thereof and the like can be illustrated. The reaction temperature is usually from 0° C. to reflux temperature, and the reaction time is usually from 1 hour to 1 day, varying based on a used starting material, solvent and reaction temperature.

Of the compounds represented by the above general formula (I) of the present invention, a compound having an unsaturated aliphatic chain can be converted into a corresponding compound having a saturated aliphatic chain represented by the above general formula (I) by catalytic hydrogenation to reduce the double bond or triple bond using a palladium catalyst such as palladium-carbon powder or the like in an inert solvent. As the solvent used in the catalytic hydrogenation, for example, methanol, ethanol, ethyl acetate, tetrahydrofuran, acetic acid, a mixed solvent thereof and the like can be illustrated. The reaction temperature is usually from 0° C. to reflux temperature, and the reaction time is usually from 1 hour to 2 days, varying based on a used starting material, solvent and reaction temperature.

The starting materials used in the above manufacturing methods can be prepared according to procedures described in literatures or analogous procedures thereof. In addition, of the compounds represented by the above formula (III), a compound wherein $R^1$ represents a group other than a hydrogen atom can be also prepared using the following compound (IIIa) which can be prepared by the above method according to the following Process 4.

solvent used in the reaction 1), for example, acetone, N,N-dimethylformamide, tetrahydrofuran, amixed solvent thereof and the like can be illustrated. In the reaction 1), the reaction temperature is usually from 0° C. to reflux temperature and the reaction time is usually from 1 hour to 1 day, varying based on a used starting material, solvent and reaction temperature. As the solvent used in the reaction 2), for example, tetrahydrofuran, ethyl acetate, acetonitrile, a mixed solvent thereof and the like can be illustrated. In the reaction 2), the reaction temperature is usually from 0° C. to reflux temperature and the reaction time is usually from 1 hour to 1 day, varying based on a used starting material, solvent and reaction temperature.

Of the compounds represented by the above general formula (III), a compound having an unsaturated aliphatic chain can be converted into a corresponding compound having a saturated aliphatic chain represented by the above general formula (III) by catalytic hydrogenation to reduce the double bond or triple bond using a palladium catalyst such as palladium-carbon powder or the like in an inert solvent. As the solvent used in the catalytic hydrogenation, for example, methanol, ethanol, ethyl acetate, tetrahydrofuran, acetic acid, a mixed solvent thereof and the like can be illustrated. The reaction temperature is usually from 0° C. to reflux temperature, and the reaction time is usually from 1 hour to 2 days, varying based on a used starting material, solvent and reaction temperature.

Of the compounds represented by the above general formula (III), the following compound (IIIc) wherein Q has a vinylene group can be also prepared according to the following process 5:

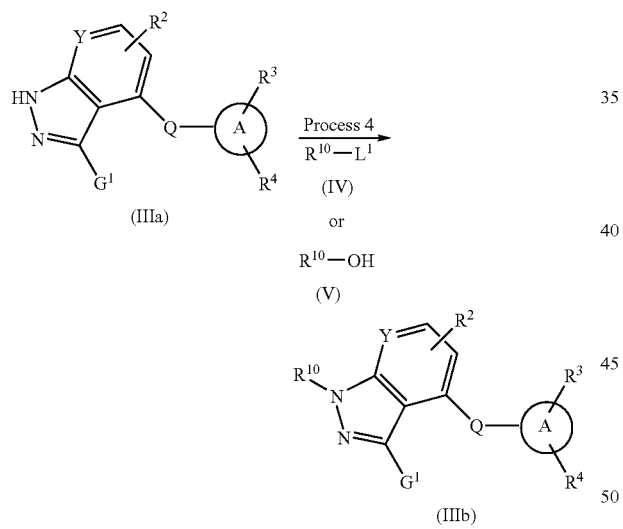

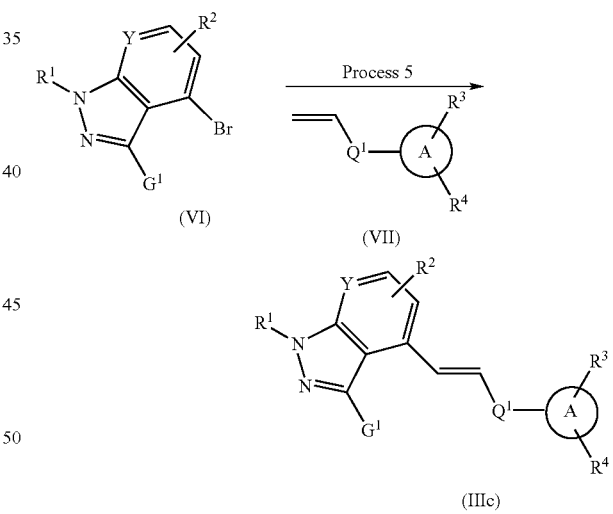

In the formula, $R^2$ to $R^4$, $R^{10}$, $G^1$, $L^1$, Q, Y and ring A have the same meanings as defined above.

Process 4

A compound represented by the above general formula (IIIb) can be prepared by subjecting a compound represented by the above general formula (IIIa) 1) to condensation with a compound represented by the above general formula (IV) in the presence of a base such as potassium carbonate, cesium carbonate, sodium hydride or the like in the presence or absence of an sodium iodide in an inert solvent, or 2) to condensation with a compound represented by the above general formula (V) in the presence of a reagent such as diethyl azodicarboxylate, diisopropyl azodicarboxylate or the like and triphenylphosphine in an inert solvent. As the In the formula, $Q^1$ represents a single bond, —$C_{1-4}$alkylene-, —$C_{1-4}$ alkylene-O—, —$C_{1-4}$ alkylene-S—, —$C_{1-4}$ alkylene-O—$C_{1-6}$ alkylene- or —$C_{1-4}$ alkylene-S—$C_{1-6}$ alkylene-; and $R^1$ to $R^4$, $G^1$, Y and ring A have the same meanings as defined above.

Process 5

A compound represented by the above general formula (IIIC) can be prepared by subjecting a compound represented by the above general formula (VI) to Heck reaction with an olefine derivative represented by the above general formula (VII) using a palladium catalyst such as palladium-carbon powder, palladium acetate, tetrakis(triphenylphosphine)palladium, dibenzylideneacetone palladium, bis(triphenylphosphine) palladium dichloride or the like in the presence or absence of a ligand such as tris(2-methylphenyl)phosphine, triphenylphosphine or the like in the presence of a base such as triethylamine, N,N-diisopropylethylamine, sodium tert-butoxide, potassium tert-butoxide, sodium carbonate, potassium carbonate, cesium fluoride or the like in an inert solvent. As the solvent used, for example, acetonitrile, toluene, tetrahydrofuran, triethylamine, N,N-diisopropylethylamine, a mixed solvent thereof and the like can be illustrated. The reaction temperature is usually from room temperature to reflux temperature, and the reaction time is usually from 1 hour to 1 day, varying based on a used starting material, solvent and reaction temperature.

Of the compounds represented by the above general formula (III), the following compound (IIId) wherein Q has an ethynylene group can be also prepared according to the following processes 6 or 7 to 9:

the presence or absence of a ligand such as tris(2-methylphenyl)phosphine, triphenyl-phosphine or the like in the presence of a base such as triethylamine, N,N-diisopropylethylamine, sodium tert-butoxide, potassium tert-butoxide, sodium carbonate, potassium carbonate, cesium fluoride or the like and copper (I) iodide in an inert solvent. As the solvent used, for example, acetonitrile, toluene, tetrahydrofuran, triethylamine, N,N-diisopropylethylamine, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 7

A compound represented by the above general formula (X) can be prepared by subjecting a compound represented by the above general formula (VI) to Sonogashira reaction

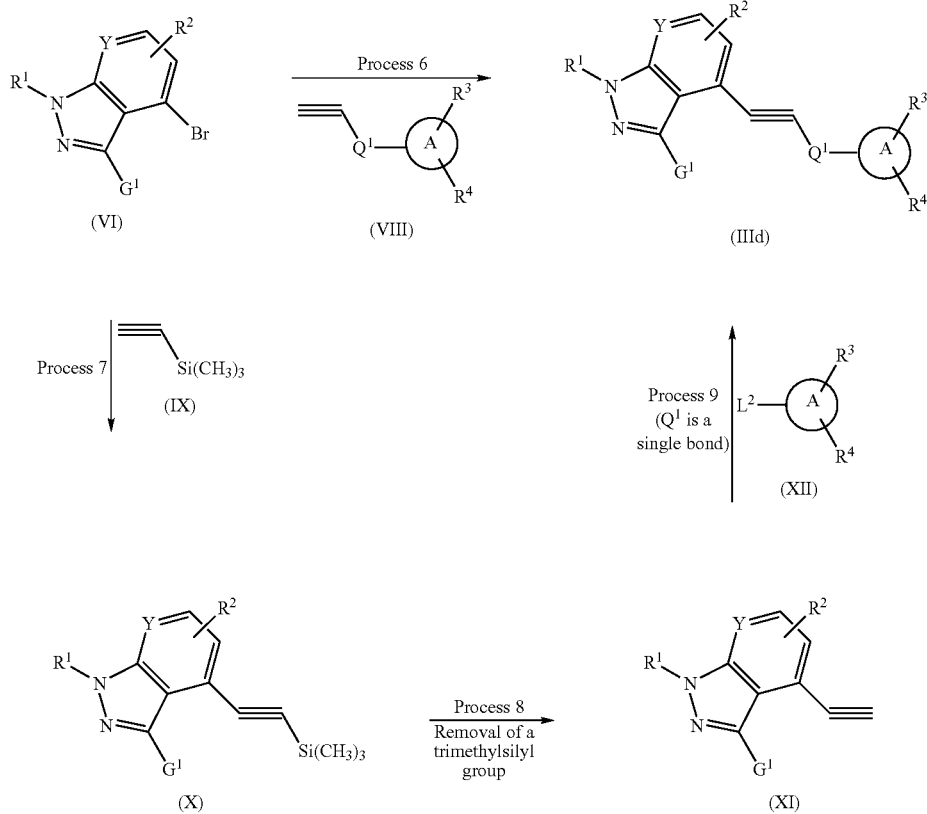

In the formula, $L^2$ represents a leaving group such as a chlorine atom, a bromine atom, an iodine atom, a trifluoromethanesulfonyloxy group or the like; and $R^1$ to $R^4$, $G^1$, $Q^1$, Y and ring A have the same meanings as defined above.

Process 6

A compound represented by the above general formula (IIId) can be prepared by subjecting a compound represented by the above general formula (VI) to Sonogashira reaction with an acetylene derivative represented by the above general formula (VIII) using a palladium catalyst such as palladium-carbon powder, palladium acetate, tetrakis(triphenylphosphine)palladium, dibenzylideneacetone palladium, bis(triphenylphosphine)-palladium dichloride or the like in with an acetylene derivative represented by the above general formula (IX) using a palladium catalyst such as palladium-carbon powder, palladium acetate, tetrakis(triphenylphosphine)palladium, dibenzylideneacetone palladium, bis(triphenylphosphine)-palladium dichloride or the like in the presence or absence of a ligand such as tris(2-methylphenyl)phosphine, triphenyl-phosphine or the like in the presence of a base such as triethylamine, N,N-diisopropylethylamine, sodium tert-butoxide, potassium tert-butoxide, sodium carbonate, potassium carbonate, cesium fluoride or the like and copper (I) iodide in an inert solvent. As the solvent used, for example, acetonitrile, toluene, tetrahydrofuran, triethylamine, N,N-diisopropylethylamine, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 8

A compound represented by the above general formula (XI) can be prepared by treating a compound represented by the above general formula (X) with a reagent such as tetra (n-butyl) ammonium fluoride, pyridinium hydrogen fluoride or the like and removing trimethylsilyl group in an inert solvent. As the solvent used, for example, tetrahydrofuran and the like can be illustrated. The reaction temperature is usually from room temperature to reflux temperature, and the reaction time is usually from 1 hour to 1 day, varying based on a used starting material, solvent and reaction temperature.

Process 9

A compound represented by the above general formula (IIId) wherein $Q^1$ represents a single bond can be prepared by subjecting a compound represented by the above general formula (XI) to Sonogashira reaction using a compound represented by the above general formula (XII) in the presence of a palladium catalyst such as palladium-carbon powder, palladium acetate, tetrakis-(triphenylphosphine) palladium, dibenzylideneacetone palladium, bis(triphenylphosphine)palladium dichloride or the likeandabasesuchastriethylamine, N,N-diisopropylethylamine, sodium tert-butoxide, potassium tert-butoxide, sodium carbonate, potassium carbonate, cesium fluoride or the like in the presence or absence of a ligand such as tris(2-methylphenyl) phosphine, triphenylphosphine or the like in the presence of copper (I) iodide in an inert solvent. As the solvent used, for example, acetonitrile, toluene, tetrahydrofuran, triethylamine, N,N-diisopropylethylamine, a mixed solvent thereof and the like can be illustrated. The reaction temperature is usually from room temperature to reflux temperature, and the reaction time is usually from 1 hour to 1 day, varying based on a used starting material, solvent and reaction temperature.

Of the compounds represented by the above general formula (III), the following compound (IIIe) wherein Q has an amide group can be also prepared according to the following processes 10 to 12:

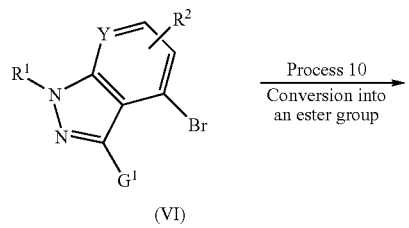

(VI)

Process 10
Conversion into an ester group

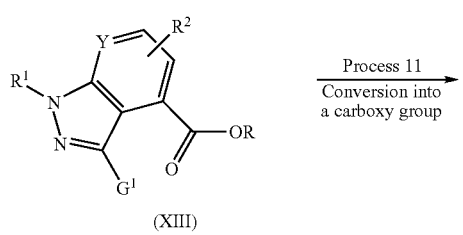

(XIII)

Process 11
Conversion into a carboxy group

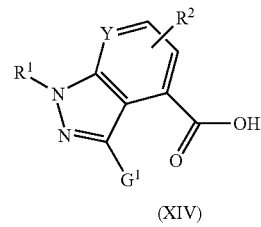

(XIV)

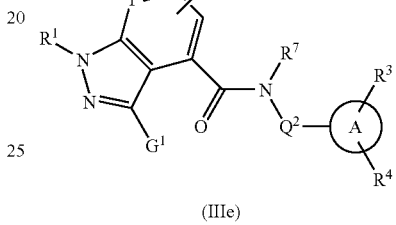

(XV)

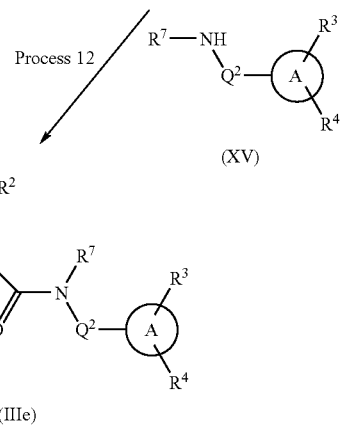

(IIIe)

In the formula, R represents a methyl group, an ethyl group or a benzyl group; $Q^2$ represents a single bond or —$C_{1-6}$ alkylene-; and $R^1$ to $R^4$, $R^7$, $G^1$, Y and ring A have the same meanings as defined above.

Process 10

A compound represented by the above general formula (XIII) can be prepared by treating a compound represented by the above general formula (VI) in the presence of a palladium catalyst such as palladium-carbon powder, palladium acetate, tetrakis-(triphenylphosphine)palladium, dibenzylideneacetone palladium, bis (triphenylphosphine) palladium dichloride or the likeandabasesuchastriethylamine, N,N-diisopropylethylamine, sodium tert-butoxide, potassium tert-butoxide, sodium carbonate, potassium carbonate, cesium fluoride or the like in the presence or absence of a ligand such as 1,3-bis(diphenyl-phosphino)propane, tris(2-methylphenyl)phosphine, triphenylphosphine or the like in an inert solvent under a carbon monoxide atmosphere. As the solvent used, for example, methanol, ethanol, benzyl alcohol, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 11

A compound represented by the above general formula (XIV) can be prepared by subjecting a compound represented by the above general formula (XIII) 1) to alkaline hydrolysis using a basic substance such as sodium hydroxide or the like, or 2) to catalytic hydrogenation using a palladium catalyst such as palladium-carbon powder or the like in an inert solvent. As the solvent used in the reaction 1), for example, water, methanol, ethanol, tetrahydrofuran, a mixed solvent thereof and the like can be illustrated. In the reaction 1), the reaction temperature is usually from 0° C. to reflux temperature and the reaction time is usually from 30 minutes to 1 day, varying based on a used starting material, solvent and reaction temperature. As the solvent used in the reaction 2), for example, methanol, ethanol, ethyl acetate, tetrahydrofuran, acetic acid, a mixed solvent thereof and the like can be illustrated. In the reaction 2), the reaction temperature is usually from 0° C. to reflux temperature and the reaction time is usually from 1 hour to 2 days, varying based on a used starting material, solvent and reaction temperature.

Process 12

A compound represented by the above general formula (IIIe) can be prepared by subjecting a compound represented by the above general formula (XIV) to condensation using a compound represented by the above general formula (XV) in the presence of a condensing agent such as 1-ethyl-3-(3-dimethylaminopropyl) carbodiimide hydrochloride, dicyclohexylcarbodiimide or the like, optionally in the presence of 1-hydroxybenzotriazole, in the presence or absence of a base such as triethylamine, N,N-diisopropylethylamine or the like in an inert solvent. As the solvent used, for example, N,N-dimethylformamide, dichloromethane, tetrahydrofuran, a mixed solvent thereof and the like can be illustrated. The reaction temperature is usually from 0° C. to reflux temperature, and the reaction time is usually from 1 hour to 2 days, varying based on a used starting material, solvent and reaction temperature.

Of the compounds represented by the above general formula (III), the following compounds (IIIg) and (IIIh) wherein $R^4$ represents the following substituent can be also prepared according to the following processes 13 to 16:

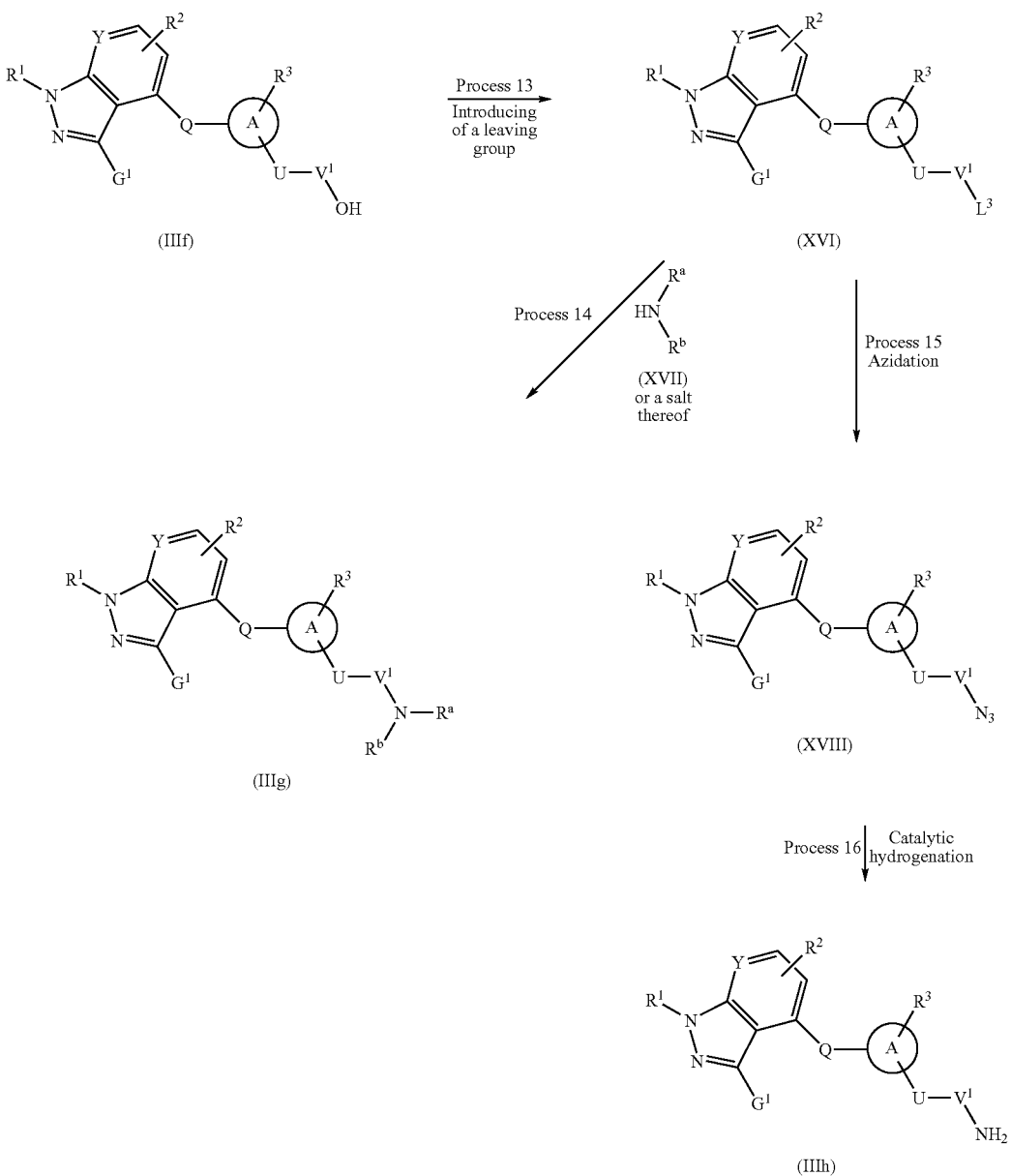

In the formula, one of $R^a$ and $R^b$ represents a hydrogen atom or a $C_{1-6}$ alkyl group which may have any 1 to 5 group selected from the above substituent group β, and the other represents a $C_{1-6}$ alkyl group which may have any 1 to 5 group selected from the above substituent group β; $L^3$ represents a leaving group such as a mesyloxy group, a tosyloxy group or the like; $V^1$ represents a $C_{1-6}$ alkylene group or a $C_{2-6}$ alkenylene group; and $R^1$ to $R^3$, $G^1$, Q, U, Y and ring A have the same meanings as defined above.

Process 13

A compound represented by the above general formula (XVI) can be prepared by subjecting a compound represented by the above general formula (IIIf) to introduction of a leaving group in the presence of a base such as triethylamine, N,N-diisopropyl-ethylamine or the like using an acid chloride such as mesyl chloride, tosyl chloride or the like in an inert solvent. As the solvent used, for example, dichloromethane, ethyl acetate, tetrahydrofuran, pyridine, a mixed solvent thereof and the like can be illustrated. The reaction temperature is usually from 0° C. to room temperature, and the reaction time is usually from 30 minutes to 1 day, varying based on a used starting material, solvent and reaction temperature.

Process 14

A compound represented by the above general formula (IIIg) can be prepared by subjecting a compound represented by the above general formula (XVI) to condensation with an amine compound represented by the above general formula (XVII) or a salt thereof in the presence or absence of a base such as triethylamine, N,N-diisopropylethylamine, pyridine, 1,8-diazabicyclo-[5.4.0] undec-7-en, sodium hydride, potassium tert-butoxide, potassium carbonate, cesium carbonate or the like, optionally adding sodium iodide, in an inert solvent. As the solvent used, for example, acetonitrile, N,N-dimethylformamide, dimethylsulfoxide, N-methylpyrrolidone, methanol, ethanol, tetrahydrofuran, water, a mixed solvent thereof and the like can be illustrated. The reaction temperature is usually from room temperature to reflux temperature, and the reaction time is usually from 1 hour to 3 days, varying based on a used starting material, solvent and reaction temperature.

Process 15

A compound represented by the above general formula (XVIII) can be prepared by subjecting a compound represented by the above general formula (XVI) to azidation using an azidating reagent such as sodium azide or the like in an inert solvent. As the solvent used, for example, dichloromethane, ethyl acetate, N,N-dimethylformamide, dimethylsulfoxide, N-methylpyrrolidone, N,N-dimethylimidazolidinone, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 16

A compound represented by the above general formula (IIIh) can be prepared by subjecting a compound represented by the above general formula (XVIII) to catalytic hydrogenation using a palladium catalyst such as palladium-carbon powder or the like in an inert solvent. As the solvent used, for example, tetrahydrofuran, methanol, ethanol, ethyl acetate, amixed solvent thereof and the like can be illustrated. The reaction temperature is usually from room temperature to reflux temperature, and the reaction time is usually from 30 minutes to 1 day, varying based on a used starting material, solvent and reaction temperature.

Of the compounds represented by the above general formula (III), the following compounds (IIIj) and (IIIk) wherein $R^4$ represents the following substituent can be also prepared according to the following processes 17 or 18 to 19:

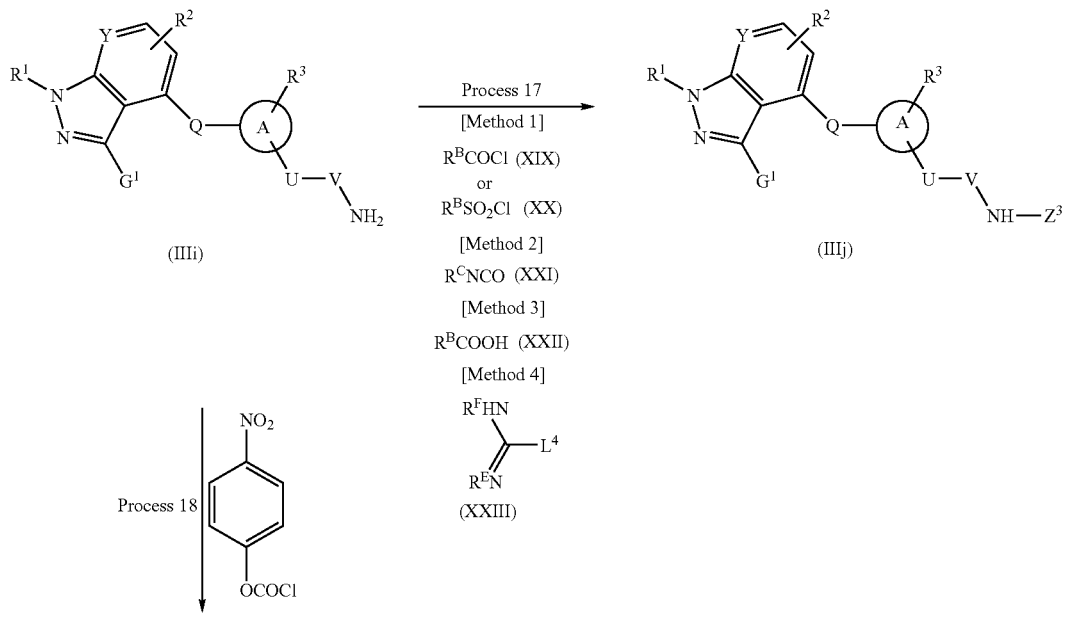

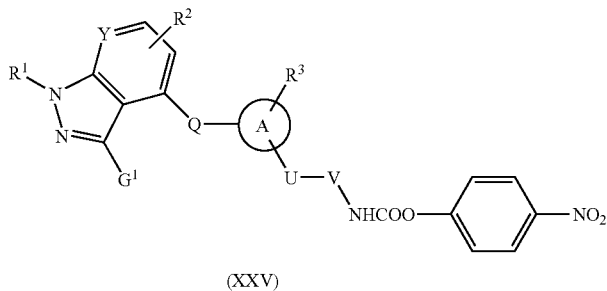

(XXV)

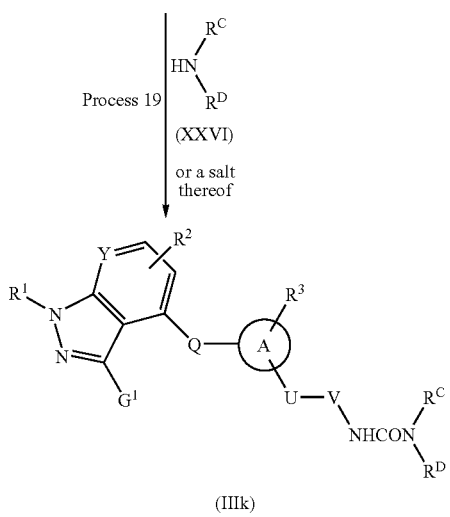

(IIIk)

In the formula, L⁴ represents a leaving group such as a pyrazolyl group, a methylthio group, a benzoriazolyl group or the like; $Z^3$ represents $COR^B$, $SO_2R^B$, $CONHR^C$, $C(=NR^E)NHR^F$; and $R^1$ to $R^3$, $R^B$, $R^C$, $R^D$, $R^E$, $R^F$, $G^1$, Q, U, V, Y and ring A have the same meanings as defined above.

Process 17

A compound represented by the above general formula (IIIj) can be prepared from a compound represented by the above general formula (IIIi) by treatment according to the following methods 1 to 4.

<Method 1>

A compound represented by the above general formula (IIIi) is allowed to react with an acid chloride represented by the above general formula (XIX) or (XX) in the presence of a base such as triethylamine, N,N-diisopropylethylamine, pyridine, 1,8-diazabicyclo[5.4.0] undec-7-en or the like in an inert solvent such as dichloromethane, ethyl acetate, tetrahydrofuran, pyridine, acetonitrile, a mixed solvent thereof or the like usually at 0° C. to reflux temperature usually for 30 minutes to 1 day.

<Method 2>

A compound represented by the above general formula (IIIi) is allowed to react with an isocyanate compound represented by the above general formula (XXI) in the presence or absence of abase such as triethylamine, N,N-diisopropylethylamine, pyridine, 1,8-diazabicyclo[5.4.0] undec-7-en or the like in an inert solvent such as dichloromethane, ethyl acetate,tetrahydrofuran, pyridine, acetonitrile, toluene, amixed solvent thereof or the like usually at 0° C. to reflux temperature usually for 30 minutes to 1 day.

<Method 3>

A compound represented by the above general formula (IIIi) is allowed to react with a carboxylic acid compound represented by the above general formula (XXII) in the presence of a condensing agent such as 1-ethyl-3-(3-dimethylaminopropyl)carbodiimide hydrochloride, dicyclohexylcarbodiimide or the like in the presence or absence of a base such as triethylamine, N,N-diisopropylethylamine or the like, optionally adding 1-hydroxybenzotriazole, in an inert solvent such as N,N-dimethylformamide, dichloromethane, a mixed solvent thereof or the like usually at 0° C. to reflux temperature usually for 1 hour to 2 days.

<Method 4>

A compound represented by the above general formula (IIIi) is allowed to react with a guanidinating reagent represented by the above general formula (XXIII) such as N-(benzyloxy-carbonyl)-1H-pyrazole-1-carboxamidine or the like in an inert solvent such as tetrahydrofuran, methanol, ethanol, toluene, a mixed solvent thereof or the like usually at room temperature to reflux temperature usually for 1 hour to 5 days.

Process 18

An activated ester compound represented by the above general formula (XXV) can be prepared by subjecting a compound represented by the above general formula (IIIi) to condensation with an activated esterifying reagent represented by the above general formula (XXIV) in the presence of a base such as triethylamine, N,N-diisopropylethylamine, Of the compounds represented by the above general formula (III), the following compound (IIII) wherein $R^4$ represents the following substituent can be also prepared according to the following processes 20 to 21 or 22:

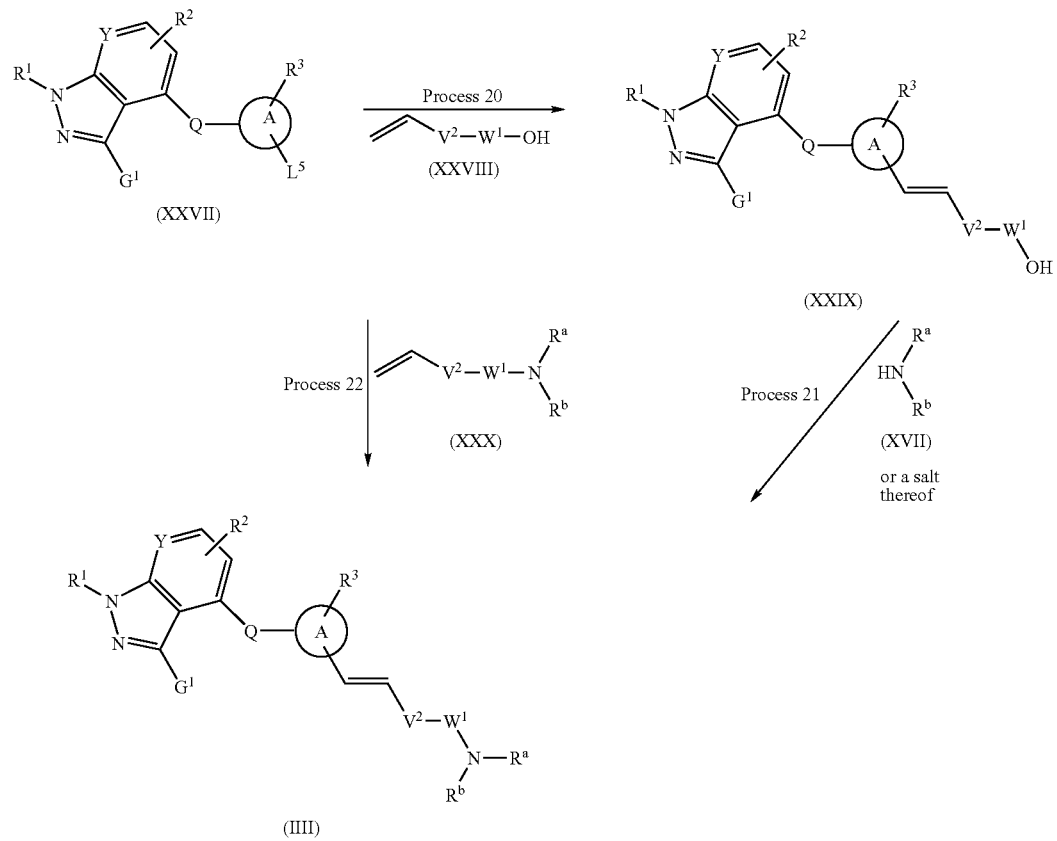

pyridine, 1,8-diazabicyclo-[5.4.0] undec-7-enorthe like in an inert solvent. As the solvent used, for example, dichloromethane, tetrahydrofuran, ethyl acetate, acetonitrile, pyridine, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 19

A compound represented by the above general formula (IIIk) can be prepared by subjecting a compound represented by the above general formula (XXV) to condensation with an amine compound represented by the above general formula (XXVI) or a salt thereof in the presence or absence of a base such as triethylamine, N,N-diisopropylethylamine, pyridine, 1,8-diazabicyclo-[5.4.0] undec-7-en, sodium hydride, potassium tert-butoxide, potassium carbonate, cesium carbonate or the like in an inert solvent. As the solvent used, for example, dichloromethane, methanol, ethanol, tetrahydrofuran, ethyl acetate, acetonitrile, pyridine, N,N-dimethylformamide, a mixed solvent thereof and the like can be illustrated. The reaction temperature is usually from room temperature to reflux temperature, and the reaction time is usually from 30 minutes to 2 days, varying based on a used starting material, solvent and reaction temperature.

In the formula, $L^5$ represents a leaving group such as a chlorine atom, a bromine atom, an iodine atom, a trifluoromethanesulfonyloxy group or the like; $V^2$ represents a $C_{1-4}$ alkylene group, a $C_{2-4}$ alkenylene group or a single bond; $W^1$ represents —CO— or $SO_2$—; and $R^1$ to $R^3$, $R^a$, $R^b$, $G^1$, Q, Y and ring A have the same meanings as defined above.

Process 20

An olefine derivative represented by the above general formula (XXIX) canbepreparedbysubjectinga-compoundrepresented by the above general formula (XXVII) to Heck reaction with an olefine derivative represented by the above general formula (XXVIII) using a palladium catalyst such as palladium-carbon powder, palladium acetate, tetrakis(triphenylphosphine)-palladium, dibenzylideneacetone palladium, bis(triphenyl-phosphine)palladium dichloride or the like in the presence or absence of a phosphine ligand such as tris(2-methylphenyl)-phosphine, triphenylphosphine or the like in the presence of a base such as triethylamine, sodium tert-butoxide, potassium tert-butoxide, cesium fluoride or the like in an inert solvent. As the solvent used, for example, acetonitrile, toluene, tetrahydrofuran, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 21

A compound represented by the above general formula (IIII) can be prepared by subjecting a compound represented by the above general formula (XXIX) to condensation with an amine derivative represented by the above general formula (XVII) or a salt thereof in the presence or absence of a condensing agent such as 1-ethyl-3-(3-dimethylaminopropyl)carbodiimide hydrochloride, dicyclohexylcarbodiimide or the like and a base such as triethylamine, N,N-diisopropylethylamine or the like, optionally adding 1-hydroxybenzotriazole, in an inert solvent. As the solvent used, for example, N,N-dimethylformamide, tetrahydrofuran, dichloromethane, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 22

A compound represented by the above general formula (IIII) can be prepared by subjecting a compound represented by the above general formula (XXVII) to Heck reaction with an olefine derivative represented by the above general formula (XXX) using a palladium catalyst such as palladium-carbon powder, palladium acetate, tetrakis(triphenylphosphine)palladium, dibenzylideneacetone palladium, bis (triphenylphosphine)palladium dichloride or the like in the presence or absence of a phosphine ligand such as tris (2-methylphenyl)phosphine, triphenylphosphine or the like in the presence of a base such as triethylamine, sodium tert-butoxide, potassium tert-butoxide, cesium fluoride or the like in an inert solvent. As the solvent used, for example, acetonitrile, toluene, tetrahydrofuran, a mixed solvent thereof and the like can be illustrated. The reaction temperature is usually from 0° C. to reflux temperature, and the reaction time is usually from 1 hour to 2 days, varying based on a used starting material, solvent and reaction temperature.

Of the compounds represented by the above general formula (II), a compound wherein $R^1$ and $R^2$ represents a hydrogen atom; Q represents a single bond, $—C_{1-6}$ alkylene-, $—C_{1-6}$ alkylene-O—, $—C_{1-6}$ alkylene-S—, $—C_{1-6}$ alkylene-O—$C_{1-6}$ alkylene- or $—C_{1-6}$ alkylene-S—$C_{1-6}$ alkylene-; and Y represents a nitrogen atom can be also prepared according to the following processes 23 to 26:

In the formula, R' represents a methyl group or an ethyl group; $Q^3$ represents a single bond, $—C_{1-6}$ alkylene-, $—C_{1-6}$ alkylene-O—, $—C_{1-6}$ alkylene-S—, $—C_{1-6}$ alkylene-O—$C_{1-6}$ alkylene- or $—C_{1-6}$ alkylene-S—$C_{1-6}$ alkylene-; and $R^3$, $R^4$ and ring A have the same meanings as defined above.

Process 23

A compound represented by the above general formula (XXXIII) can be prepared by subjecting a compound represented by the above general formula (XXXI) to condensation with a cyano acetic acid derivative represented by the above general formula (XXXII) in the presence of an additive such as acetic acid, ammonium acetate or the like in an inert solvent. As the solvent used, for example, toluene, benzene, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 24

A compound represented by the above general formula (XXXV) can be prepared by subjecting a compound represented by the above general formula (XXXIII) to condensation with a compound represented by the above general formula (XXXIV) in an inert solvent. As the solvent used, for example, methanol, ethanol, 2-propanol, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 25

A compound represented by the above general formula (XXXVI) can be prepared by subjecting a compound represented by the above general formula (XXXV) to cyclization by treating with hydrobromic acid in an inert solvent. As the solvent used, for example, acetic acid and the like can be illustrated. The reaction temperature is usually from 0° C. to reflux temperature, and the reaction time is usually from 1 hour to 1 day, varying based on a used starting material, solvent and reaction temperature.

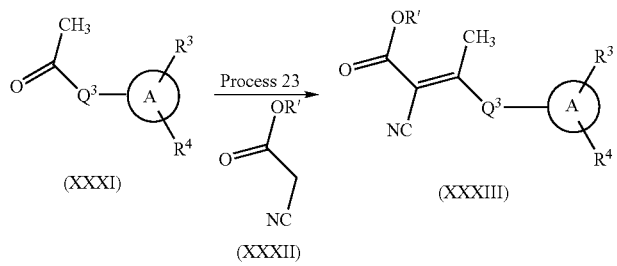

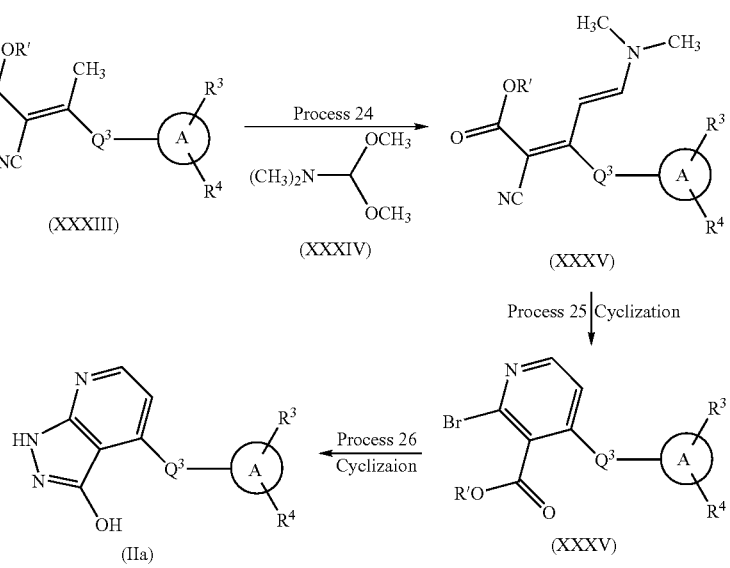

Process 26

A compound represented by the above general formula (IIa) can be prepared by subjecting a compound represented by the above general formula (XXXVI) to cyclization using hydrazine or a hydrate thereof in an inert solvent. As the solvent used, for example, N-methlpyrrolidone, N,N-dimethylformamide, n-butanol, a mixed solvent thereof and the like can be illustrated. The reaction temperature is usually from room temperature to reflux temperature, and the reaction time is usually from 1 hour to 1 day, varying based on a used starting material, solvent and reaction temperature.

Of the compounds represented by the above general formula (VI), a compound wherein Y represents CH can be prepared according to the following processes 27 to 31:

resented by the above general formula (XXXVIII) to reduction in the presence of an acid such as hydrochloric acid or the like using a reducing agent such as tin chloride or a hydrate thereof or the like in an inert solvent. As the solvent used, for example, water and the like can be illustrated. The reaction temperature is usually from room temperature to reflux temperature, and the reaction time is usually from 30 minutes to 1 day, varying based on a used starting material, solvent and reaction temperature.

Process 29

A compound represented by the above general formula (XXXX) can be prepared by deriving a compound represented by the above general formula (XXXIX) into a dia-

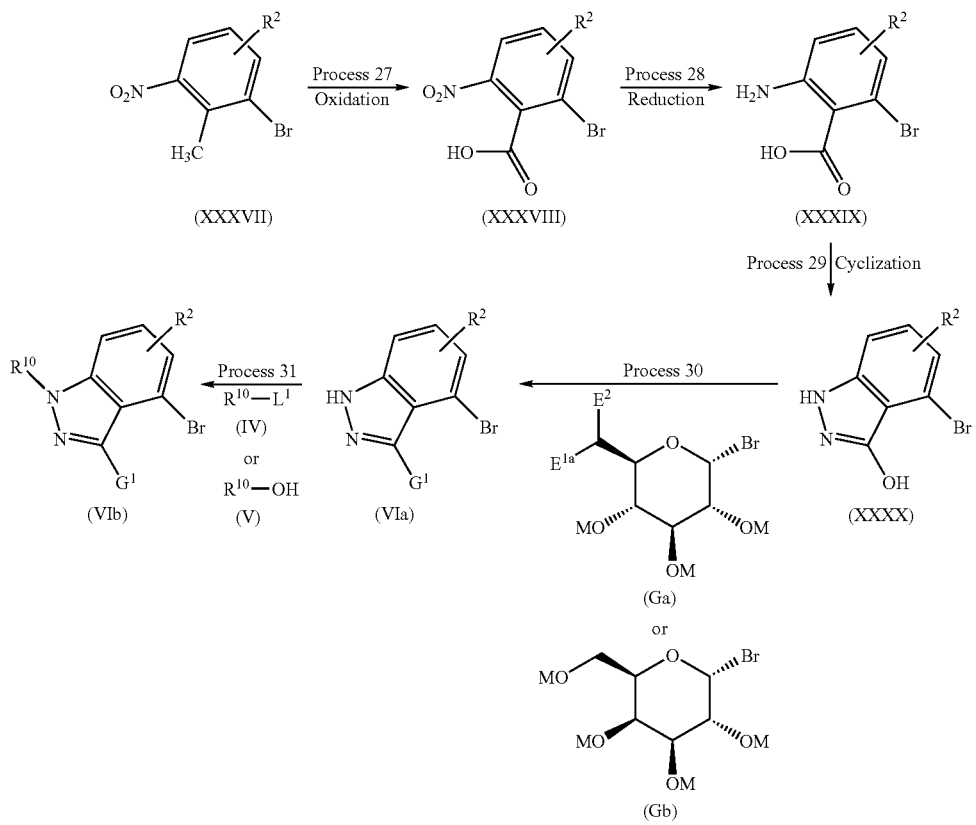

In the formula, $R^2$, $R^{10}$, $E^{1a}$, $E^{2a}$, $L^1$, $G^1$ and M have the same meanings as defined above.

Process 27

A compound represented by the above general formula (XXXVIII) can be prepared by subjecting a compound represented by the above general formula (XXXVII) to oxidation in the presence of a base such as sodium carbonate or the like using an oxidizing agent such as potassium permanganate or the like in an inert solvent. As the solvent used, for example, water and the like can be illustrated. The reaction temperature is usually from room temperature to reflux temperature, and the reaction time is usually from 1 hour to 3 days, varying based on a used starting material, solvent and reaction temperature.

Process 28

A compound represented by the above general formula (XXXIX) can be prepared by subjecting a compound repzonium compound in the presence of an acid such as hydrochloric acid or the like using sodium nitrite in an inert solvent, and then by subjecting the compound to reduction in the presence of an acid such as hydrochloric acid or the like using a reducing agent such as tin chloride or a hydrate thereof or the like in an inert solvent, and cyclization. As the solvent used in the reaction into the diazonium compound, for example, water and the like can be illustrated. The reaction temperature is usually from 0° C. to reflux temperature, and the reaction time is usually from 30 minutes to 1 day, varying based on a used starting material, solvent and reaction temperature. As the solvent used in the reduction and cyclization reactions, for example, water and the like can be illustrated. The reaction temperature is usually from 0° C. to reflux temperature, and the reaction time is usually from 30 minutes to 1 day, varying based on a used starting material, solvent and reaction temperature.

Process 30

A glycosidated compound represented by the above general formula (VIa) can be prepared by subjecting a compound represented by the above general formula (XXXX) to glycosidation using a sugar donor represented by the above general formula (Ga) or (Gb) such as acetobromo-α-D-glucose, acetobromo-α-D-galactose, 2,3,4,6-tetra-O-pivaloyl-α-D-glucopyranosyl bromide, 2,3,4,6-tetra-O-pivaloyl-α-D-galactopyranosyl bromide, 2,3,4,6-tetra-O-benzoyl-α-D-glucopyranosyl bromide, 2,3,4,6-tetra-O-benzoyl-α-D-galactopyranosyl bromide or the like in the presence of a silver salt such as silver carbonate, silver oxide or the like or a base such as sodium carbonate, potassium carbonate, cesium carbonate, sodium hydroxide, potassium hydroxide, sodium hydride or the like in the presence or absence of a phase transfer catalyst such as benzyltri(n-butyl)ammonium chloride, benzyltri(n-butyl)-ammonium bromide, tetra(n-butyl)ammonium hydrogen sulfate or the like in an inert solvent. As the solvent used, for example, tetrahydrofuran, 1,2-dimethoxyethane, N,N-dimethylformamide, acetonitrile, dichloromethane, toluene, benzotrifluoride, water, a mixed solvent thereof and the like can be illustrated. The reaction temperature is usually from room temperature to reflux temperature, and the reaction time is usually from 1 hour to 3 days, varying based on a used starting material, solvent and reaction temperature.

Process 31

A compound represented by the above general formula (VIb) can be prepared by subjecting a compound represented by the above general formula (VIa) 1) to condensation with a compound represented by the above general formula (IV) in the presence of a base such as potassium carbonate, cesium carbonate, sodium hydride or the like in the presence or absence of sodium iodide in an inert solvent, or 2) to condensation with a compound represented by the above general formula (V) in the presence of a reagent such as diethyl azodicarboxylate, diisopropyl azodicarboxylate or the like and triphenylphosphine in an inert solvent. As the solvent used in the reaction 1), for example, acetone, N,N-dimethylformamide, tetrahydrofuran, amixedsolvent thereof and the like can be illustrated. In the reaction 1), the reaction temperature is usually from 0° C. to reflux temperature and the reaction time is usually from 1 hour to 1 day, varying based on a used starting material, solvent and reaction temperature. As the solvent used in the reaction 2), for example, tetrahydrofuran, ethyl acetate, acetonitrile, a mixed solvent thereof and the like can be illustrated. In the reaction 2), the reaction temperature is usually from room temperature to reflux temperature and the reaction time is usually from 1 hour to 1 day, varying based on a used starting material, solvent and reaction temperature.

In case of compounds having a hydroxy group, an amino group and/or a carboxy group in the above procedures, they can be also used in each reaction after introducing any protective group in the usual way as occasion demand. The protective group can be optionally removed in any subsequent reaction in the usual way.

The compounds represented by the above general formula (I) of the present invention obtained by the above production processes can be isolated and purified by conventional separation means such as fractional recrystallization, purification using chromatography, solvent extraction and solid phase extraction.

The nitrogen-containing fused-ring derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris(hydroxymethyl)aminomethane, arginine, lysine and the like.

The compounds represented by the above general formula (I) of the present invention include their solvates with pharmaceutically acceptable solvents such as ethanol and water.

Of the nitrogen-containing fused-ring derivatives represented by the above general formula (I) of the present invention and the prodrugs thereof, there are two geometrical isomers, cis(Z)-isomer and trans(E)-isomer, in each compound having an unsaturated bond. In the present invention, either of the isomers can be employed.

Of the nitrogen-containing fused-ring derivatives represented by the above general formula (I) of the present invention and the prodrugs thereof, there are two optical isomers, R-isomer and S-isomer, in each compound having an asymmetric carbon atomexcluding the sugarmoiety. In the present invention, either of the isomers can be employed, and a mixture of both isomers can be also employed.

A prodrug of a compound represented by the above general formula (I) of the present invention can be prepared by introducing an appropriate group forming a prodrug into any one or more groups selected from a hydroxy group, an amino group and a cyclic amino group such as a pyrazole ring, a piperazine ring or the like of the compound represented by the above general formula (I) using a corresponding reagent to produce a prodrug such as a halide compound or the like in the usual way, and then by suitably isolating and purificating in the usual way as occasion demands. As a group forming a prodrugused in a hydroxy group or an amino group, for example, a $C_{2-7}$ acyl group, a $C_{1-6}$ alkoxy ($C_{2-7}$ acyl) group, a $C_{2-7}$ alkoxycarbonyl($C_{2-7}$ acyl) group, a $C_{2-7}$ alkoxycarbonyl group, a $C_{6-10}$ aryl($C_{2-7}$ alkoxycarbonyl) group, a $C_{1-6}$ alkoxy($C_{2-7}$ alkoxycarbonyl) group or the like can be illustrated. As a group forming a prodrug used in a cyclic amino group, for example, a $C_{2-7}$ acyl group, a $C_{1-6}$ alkoxy($C_{2-7}$ acyl) group, a $C_{2-7}$ alkoxycarbonyl($C_{2-7}$ acyl) group, a $C_{2-7}$ alkoxycarbonyl group, a $C_{6-10}$ aryl ($C_{2-7}$ alkoxycarbonyl) group, a $C_{1-6}$ alkoxy($C_{2-7}$ alkoxycarbonyl) group, a ($C_{2-7}$ acyloxy)methyl group, a 1-($C_{2-7}$ acyloxy)ethyl group, a ($C_{2-7}$ alkoxycarbonyl)-oxymethyl group, a 1-[($C_{2-7}$ alkoxycarbonyl)oxy]ethyl group, a ($C_{3-7}$ cycloalkyl) oxycarbonyloxymethyl group, a 1-[$C_{3-7}$ cycloalkyl)oxycarbonyloxy]ethyl group or the like can be illustrated. The term "$C_{1-6}$ alkoxy($C_{2-7}$ acyl) group" means the above $C_{2-7}$ acyl group substituted by the above $C_{1-6}$ alkoxy group; the term "$C_{2-7}$ alkoxycarbonyl ($C_{2-7}$ acyl) group" means the above $C_{2-7}$ acyl group substituted by the above $C_{2-7}$ alkoxycarbonyl group; and the term "$C_{1-6}$ alkoxy($C_{2-7}$ alkoxycarbonyl) group" means the above $C_{2-7}$ alkoxycarbonyl group substituted by the above $C_{1-6}$ alkoxy group. The term "($C_{2-7}$ acyloxy)methyl group" means a hydroxymethyl group O-substituted by the above $C_{2-7}$ acyl group; the term "1-($C_{2-7}$ acyloxy)ethyl group" means a 1-hydroxyethyl group O-substituted by the above $C_{2-7}$ acyl group; the term "($C_{2-7}$ alkoxycarbonyl)oxymethyl group" means a hydroxymethyl group O-substituted by the above $C_{2-7}$ alkoxycarbonyl group; the term "1-[($C_{2-7}$ alkoxycarbonyl)-oxy] ethyl group" means a 1-hydroxyethyl group O-substituted by the above $C_{2-7}$ alkoxycarbonyl group; the term "($C_{3-7}$ cycloalkyl)oxycarbonyl group" means a cyclic alkoxycarbonyl group having the above $C_{3-7}$ cycloalkyl group; the term "($C_{3-7}$ cycloalkyl)oxycarbonyloxymethyl group" means a hydroxymethyl group O-substituted by the above ($C_{3-7}$ cycloalkyl)oxycarbonyl group; and the term "1-[$C_{3-7}$ cycloalkyl)oxycarbonyloxy]ethyl group" means a 1-hydroxyethyl group O-substituted by the above ($C_{3-7}$ cycloalkyl)oxycarbonyl group. In addition, as a group forming a prodrug, a glucopyranosyl group or a galactopyranosyl group can be illustrated. For example, these groups are preferably introduced into the hydroxy group at the 4 or 6 position of the glucopyranosyloxy group or the galactopyranosyloxy group, and are more preferably introduced into the hydroxy group at the 4 or 6 position of the glucopyranosyloxy group.

The nitrogen-containing fused-ring derivatives represented by the above general formula (I) of the present invention, for example, showed a potent inhibitory activity on human SGLT1 or SGLT2 in a human SGLT1 or SGLT2 inhibitory activity confirmatory test as described below. Therefore, a nitrogen-containing fused-ring derivative represented by the above general formula (I) of the present invention can exert an excellent inhibitory activity of SGLT1 at the small intestine or an excellent inhibitory activity of SGLT2 at the kidney, and significantly inhibit blood glucose level increase or significantly lower blood glucose level. Therefore, a nitrogen-containing fused-ring derivative represented by the above general formula (I) of the present invention, a pharmaceutically acceptable salt thereof and a prodrug thereof is extremely useful as an agent for the inhibition of postprandial hyperglycemia, the inhibition of advancing into diabetes in a subject with impaired glucose tolerance and the prevention or treatment of a disease associated with hyperglycemia such as diabetes, impaired glucose tolerance (IGT), diabetic complications (e.g., retinopathy, neuropathy, nephropathy, ulcer, macroangiopathy), obesity, hyperinsulinemia, hyperlipidemia, hypercholesterolemia, hypertriglyceridemia, lipid metabolism disorder, atherosclerosis, hypertension, congestive heart failure, edema, hyperuricemia, gout or the like, which relates to SGLT1 activity at the small intestine and SGLT2 activity at the kidney.

Furthermore, the compounds of the present invention can be suitably used in combination with at least one member selected from the following drugs. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, anamylinanalogue, anamylinagonist, analdose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growthfactor (PDGF) analogue (e.g., PDGF-AA, PDGF-BB, PDGF-AB), epidermal growth factor (EGF), nerve growth factor, a carnitine derivative, uridine, 5-hydroxy-1-methylhydantoin, EGB-761, bimoclomol, sulodexide, Y-128, antidiarrhoics, cathartics, a hydroxymethylglutaryl coenzyme A reductase inhibitor, a fibrate, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-y agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-αagonists such as GW-9578 and BM-170744, peroxisome proliferator-activated receptor-α/γagonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX- 0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, for example, α-glucosidase inhibitors such as acarbose, voglibose, miglitol, CKD-711, emiglitate, MDL-25,637, camiglibose and MDL-73,945, α-amylase inhibitors such as AZM-127,SGLT1 inhibitors described in pamphlets of International Publication Nos. WO02/098893, WO2004/014932 and the like are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers are used preferably for diabetes, impaired glucose tolerance or diabetic complications, and more preferably for diabetes or impaired glucose tolerance because of lowering blood glucose level by acting on pancreaticβ-cells and enhancing the insulin secretion.

As SGLT2 inhibitors, T-1095 and compounds described in Japanese patent publications Nos. Hei10-237089 and 2001-288178, and International Publications Nos. WO01/16147, WO01/27128, WO01/68660, WO01/74834, WO01/74835, WO02/28872, WO02/36602, WO02/44192, WO02/53573, WO03/000712, WO03/020737 and the like are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at the kidney's proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors are preferably used for diabetic complications because of inhibiting formation of advanced glycation endproducts which are accelerated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelerated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecarnine hydrochloride, levocarnitine chloride, levocarnitine, ST-261or the like are illustrated. These drugs, insulin-like growth factor-I, platelet-derived growth factor, platelet derived growth factor analogues, epidermal growth factor, nerve growth factor, uridine, 5-hydroxy-1-methyl-hydantoin, EGB-761, bimoclomol, sulodexide and Y-128 are preferably used for diabetic complications.

As antidiarrhoics or cathartics, polycarbophil calcium, albumin tannate, bismuth subnitrate or the like are illustrated. These drugs are preferably used for diarrhea, constipation or the like accompanying diabetes or the like.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatinor the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibrates, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibrates are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating β3-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hyper-cholesterolemia, hypertriglyceridemia or lipid metabolism disorder, and more preferably for hyperlipidemia or hyper-cholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856, TAK-475 or the like are illustrated; as nicotinic acid derivatives, nicotinicacid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal trigylceride transfer protein inhibitors, lipoxygenase inhibitors and low-density lipoprotein receptor enhancers are preferably used for hyperlipidemia, hypercholesterolemia, hypertriglyceridemia or lipidmetabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, γ-aminobutyric acid receptor antagonists, $H_3$-histamine antagonists, L-histidine, leptin, leptin analogues, leptin receptor agonists, melanocortin receptor agonists (especially, MC3-R agonists, MC4-Ragonists), α-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activatingpeptide, brain-derived-neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromoctiptine mesylate or the like are illustrated; as cannabinoid receptor antagonists, rimonabant or the like are illustrated; as γ-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 orthe like are illustrated; andasneuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril orthe like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodiumsitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassiumcanrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazinehydrochloride, cadralazine, budralazineorthe like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as ($\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with a compound of the present invention, for example, in the use for diabetes, the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, aglycogensynthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer, a SGLT2 inhibitor and an insulin or insulin analogue is most preferable. Similarly, in the use for diabetic complications, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipidperoxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a glucose-absorption inhibitor, a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered. The pharmaceutical compositions of the present invention also include sustained release formulation including gastrointestinal mucoadhesive formulation (e.g., International publications Nos. WO99/10010, WO99/26606, and Japanese patent publication No. 2001-2567).

These pharmaceutical compositions can be prepared by admixing with or by diluting and dissolving with an appropriate pharmaceutical additive such as excipients, disintegrators, binders, lubricants, diluents, buffers, isotonicities, antiseptics, moistening agents, emulsifiers, dispersing agents, stabilizingagents, dissolvingaids and the like, and formulating the mixture in accordance with conventional methods. In case of the uses of the compound of the present invention in combination with other drug(s), they can be prepared by formulating each active ingredient together or individually in a similar manner as defined above.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with other drug(s), the dosage of the compound of the present invention can be decreased, depending on the dosage of the drug(s).

EXAMPLES

The present invention is further illustrated in more detail by way of the following Reference Examples, Examples and Test Examples. However, the present invention is not limited thereto.

Reference Example 1

2-Amino-2-methylpropionamide

To a solution of 2-benzyloxycarbonylamino-2-methylpropionic acid (1 g) in N,N-dimethylformamide (10 mL) were added 1-hydroxybenzotriazole (0.63 g), 1-ethyl-3-(3-dimethyl-aminopropyl) carbodiimide hydrochloride (1.21 g), triethylamine (1.76 mL) and 28% aqueous ammonia solution (2 mL), and the mixture was stirred at room temperature overnight. The reaction mixture was poured into water, and the resulting mixture was extracted with ethyl acetate. The organic layer was washed with 0.5 mol/L hydrochloric acid, water, 1 mol/L aqueous sodium hydroxide solution, water and brine successively, and dried over anhydrous sodium sulfate. The solvent was removed under reduced pressure to give 2-benzyloxycarbonylamino-2-methylpropionamide (0.26 g) This material was dissolved in methanol (5 mL). To the solution was added 10% palladium-carbon powder (30 mg), and the mixture was stirred at room temperature under a hydrogen atmosphere for 3 hours. The insoluble material was removed by filtration, and the filtrate was concentrated under reduced pressure to give the title compound (0.11 g).

$^1$H-NMR (DMSO-$d_6$) δ ppm: 1.15 (6H, s), 1.9 (2H, brs), 6.83 (1H, brs), 7.26 (1H, brs)

Reference Example 2

4-Bromo-1H-indazol-3-ol

To a mixture of 2-bromo-6-nitrotoluene (8 g), sodium carbonate (18.1 g) and water (500 mL) was added potassium permanganate (23.4 g), and the mixture was heated for reflux overnight. The insoluble material was removed by filtration, and the filtrate was washed with diethyl ether. The aqueous layer was acidified by addition of concentrated hydrochloric acid, and the mixture was extracted with ethyl acetate (three times). The extract was dried over anhydrous magnesium sulfate, and the solvent was removed under reduced pressure to give 2-bromo-6-nitrobenzoic acid (2.78 g). Tin (II) chloride dihydrate (9.18 g) was dissolved in concentrated hydrochloric acid (30 mL). To the solution was added 2-bromo-6-nitrobenzoic acid (2.78 g), and the mixture was stirred at 80° C. for 1.5 hours. The insoluble material was collected by filtration, washed with 2 mol/L hydrochloric acid and dried under reduced pressure. The obtained crystal (2.05 g) was suspended in concentrated hydrochloric acid (35 mL). To the suspension was added a solution of sodium nitrite (0.79 g) in water (6 mL) under ice-cooling, and the mixture was stirred for 20 minutes. To the reaction mixture was added a solution of tin (II) chloride dihydrate (5.78 g) in concentrated hydrochloric acid (10 mL), and the mixture was stirred at room temperature for 1 hour. Then the mixture was stirred at 80° C. for 30 minutes. The reaction mixture was cooled to room temperature, and the precipitated crystals were collected by filtration. The crystals were washed with water and dried under reduced pressure to give the title compound (1.27 g)

$^1$H-NMR (CD$_3$OD) δ ppm: 7.18 (1H, dd, J=6.3 Hz, 1.8 Hz), 7.2-7.3 (2H, m)

Reference Example 3

4-Bromo-3-(2,3,4,6-tetra-O-pivaloyl-β-D-glucopyranosyloxy)-1H-indazole

A mixture of 4-bromo-1H-indazol-3-ol (1.27 g), potassium carbonate (1.65 g) and 2,3,4,6-tetra-O-pivaloyl-α-D-gluco-pyranosyl bromide (which can be prepared in a manner described in literature, for example, Liebigs Ann. Chem. 1982, pp. 41-48; J. Org. Chem. 1996, vol.61, pp. 9541-9545) (4.15 g) in acetonitrile (20 mL) was stirred at room temperature overnight. The reaction mixture was poured into water, and the resulting mixture was extracted with diethyl ether. The extract was washed with water and brine, and dried over an hydrous magnesium sulfate. The solvent was removed under reduced pressure, and the residue was purified by column chromatography on silica gel (eluent: n-hexane/ethyl acetate=5/1-2/1) to give the title compound (2.04 g).

$^1$H-NMR (CDCl$_3$) δ ppm: 1.09 (9H, s), 1.14 (9H, s), 1.17 (9H, s), 1.19 (9H, s), 3.95-4.05 (1H, m), 4.1-4.2 (1H, m), 4.2-4.3 (1H, m), 5.25-5.35 (1H, m), 5.4-5.5 (2H, m), 5.88 (1H, d, J=7.6 Hz), 7.1-7.2 (1H, m), 7.2-7.3 (2H, m), 8.97 (1H, s)

Example 1

4-[(E)-2-Phenylvinyl]-3-(2,3,4,6-tetra-O-pivaloyl-β-D-glucopyranosyloxy)-1H-indazole A mixture of 4-bromo-3-(2,3,4,6-tetra-O-pivaloyl-β-D-glucopyranosyloxy)-1H-indazole (75 mg), styrene (33 mg), triethylamine (0.073 mL), palladium (II) acetate (2 mg) and tris(2-methylphenyl)phosphine (6 mg) inacetonitrile (2 mL) was heated for reflux under an argon atmosphere overnight. The reaction mixture was purified by column chromatography on silica gel (eluent: n-hexane/ethyl acetate=3/1-2/1) to give the title compound (50 mg).

$^1$H-NMR (CDCl$_3$) δ ppm: 0.98 (9H, s), 1.16 (9H, s), 1.18 (9H, s), 1.19 (9H, s), 3.95-4.05 (1H, m), 4.16 (1H, dd, J=12.5 Hz, 5.7 Hz), 4.24 (1H, dd, J=12.5 Hz, 1.9 Hz), 5.25-5.35 (1H,m), 5.45-5.6 (2H,m), 5.96 (1H, d, J=8.1 Hz), 7.18 (1H, d, J=8.4 Hz), 7.2-7.4 (3H, m), 7.4-7.5 (3H, m), 7.67 (2H, d, J=7.7 Hz), 7.78 (1H, d, J=16.4 Hz), 8.89 (1H, s)

Example 2

3-(2,3,4,6-Tetra-O-pivaloyl-β-D-glucopyranosyloxy)-4-[(E)-2-(pyridin-4-yl)vinyl]-1H-indazole The title compound was prepared in a similar manner to that described in Example 1 using 4-vinylpyridine instead of styrene.

$^1$H-NMR (CDCl$_3$) δ ppm: 0.97 (9H, s), 1.17 (9H, s), 1.18 (9H, s), 1.19 (9H, s), 4.0-4.05 (1H, m), 4.16 (1H, dd, J=12.7 Hz, 5.4 Hz), 4.25 (1H, dd, J=12.7 Hz, 1.8 Hz), 5.25-5.35 (1H, m), 5.45-5.6 (2H, m), 5.96 (1H, d, J=8.1 Hz), 7.15 (1H, d, J=16.4 Hz), 7.26 (1H, d, J=7.7 Hz), 7.38 (1H, t, J=7.7 Hz), 7.45-7.6 (3H, m), 7.98 (1H, d, J=16.4 Hz), 8.6-8.7 (2H, m), 8.97 (1H, s)

Reference Example 4

4-Ethynyl-3-(2,3,4,6-tetra-0-pivaloyl-β-D-glucopyranosyloxy)-1H-indazole

To a solution of 4-bromo-3-(2,3,4,6-tetra-O-pivaloyl-β-D-glucopyranosyloxy)-1H-indazole (0.5 g) in triethylamine (5 mL) were added trimethylsilylacetylene (0.2 mL), tetrakis (triphenylphosphine) palladium (0) (81 mg) and copper (I) iodide (27 mg), and the mixture was stirred at 80° C. under an argon atmosphere overnight. The reaction mixture was cooled to room temperature and diluted with diethyl ether. The insoluble material was removed by filtration. The filtrate was washed with water and brine, and dried over anhydrous sodium sulfate. The solvent was removed under reduced pressure, and the residue was purified by column chromatography on silica gel (eluent: n-hexane/ethyl acetate=4/1-3/1-2/1) to give 4-(2-trimethylsilylethynyl)-3-(2,3,4,6-tetra-O-pivaloyl-β-D-glucopyranosyloxy)-1H-indazole (0.4 g). This material was dissolved in tetrahydrofuran (5 mL). To the solution was added tetra(n-butyl) ammonium fluoride (0.15 g), and the mixture was stirred at room temperature for 1 hour. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1-1/1) to give the title compound (0.33 g).

$^1$H-NMR (CDCl$_3$) δ ppm: 1.08 (9H, s), 1.14 (9H, s), 1.17 (9H, s), 1.2 (9H, s), 3.37 (1H, s), 3.95-4.05 (1H, m), 4.17 (1H, dd, J=12.4 Hz, 5.2 Hz), 4.26 (1H, dd, J=12.4 Hz, 1.7 Hz), 5.25-5.35 (1H, m), 5.4-5.5 (2H, m), 5.84 (1H, d, J=8.0 Hz), 7.23 (1H, dd, J=4.7 Hz, 3.0 Hz), 7.25-7.35 (2H, m), 9.0 (1H, s)

Example 3

4-[2-(4-Hydroxy-3-methylphenyl)ethynyl]-3-(2,3,4,6-tetra-O-pivaloyl-β-D-glucopyranosyloxy)-1H-indazole To a solution of 4-ethynyl-3-(2,3,4,6-tetra-o-pivaloyl-β-D-glucopyranosyloxy)-1H-indazole (66 mg) in triethylamine (1 mL) were added 4-iodo-2-methylphenol (25 mg), tetrakis (triphenylphosphine) palladium (0) (12 mg) and copper (I) iodide (4 mg), and the mixture was stirred at 80° C. under an argon atmosphere overnight. The reaction mixture was cooled to room temperature and diluted with ethyl acetate. The insoluble material was removed by filtration, and the filtrate was concentrated under reduced pressure. The residue was purified by column chromatography on silica gel (eluent: n-hexane/ethylacetate=3/1-2/1-1/1) to give the title compound (47 mg).

$^1$H-NMR (CDCl$_3$) δ ppm: 1.02 (9H, s), 1.14 (9H, s), 1.15 (9H, s), 1.17 (9H, s), 2.32 (3H, s), 3.9-4.0 (1H, m), 4.12 (1H, dd, J=12.3 Hz, 5.7 Hz), 4.22 (1H, dd, J=12.3 Hz, 1.9 Hz), 4.84 (1H, s), 5.2-5.3 (1H, m), 5.35-5.5 (2H, m), 6.05 (1H, d, J=7.8 Hz), 6.8 (1H, d, J=8.3 Hz), 7.2-7.35 (3H, m), 7.4 (1H, dd, J=8.3 Hz, 1.9 Hz), 7.51 (1H, d, J=1.9 Hz), 8.97 (1H, s)

Example 4

3-(β-D-Glucopyranosyloxy)-4-(2-phenylethyl)-1H-indazole

To a solution of 4-[ (E)-2-phenylvinyl]-3-(2,3,4,6-tetra-O-pivaloyl-β-D-glucopyranosyloxy)-1H-indazole (50 mg) in tetrahydrofuran (4 mL) was added 10% palladium-carbon powder (25 mg), and the mixture was stirred at room temperature under a hydrogen atmosphere for 5 hours. The insoluble material was removed by filtration, and the filtrate was concentrated under reduced pressure to give 4-(2-phenylethyl)-3-(2,3,4,6-tetra-O-pivaloyl-β-D-glucopyranosyloxy)-1H-indazole (50 mg) This material was dissolved in methanol (4 mL). To the solution was added sodium methoxide (28% methanol solution, 0.065 mL), and the mixture was stirred at 50° C. overnight. To the reaction mixture was added acetic acid (0.04 mL), and the resulting mixture was purified by column chromatography on silica gel (eluent: dichloromethane/methanol=5/1) to give the title compound (21 mg).

$^1$H-NMR (CD$_3$OD) δ ppm: 2.9-3.1 (2H, m), 3.1-3.65 (6H, m), 3.71 (1H, dd, J=12.2 Hz, 5.5 Hz), 3.89 (1H, dd, J=12.2 Hz, 2.2 Hz), 5.66 (1H, d, J=7.9 Hz), 6.76 (1H, d, J=6.9 Hz), 7.1-7.3 (7H, m)

Example 5

3-(β-D-Glucopyranosyloxy)-4-[2-(4-hydroxy-3-methylphenyl)-ethyl]-1H-indazole

The title compound was prepared in a similar manner to that described in Example 4 using 4-[2-(4-hydroxy-3-methyl-phenyl)ethynyl]-3-(2,3,4,6-tetra-O-pivaloyl-β-D-gluco-pyranosyloxy)-1H-indazole instead of 4-[(E)-2-phenylvinyl]-3-(2,3,4,6-tetra-O-pivaloyl-β-D-glucopyranosyloxy)-1H-indazole.

$^1$H-NMR (CD$_3$OD) δ ppm: 2.16 (3H, s), 2.75-2.95 (2H, m), 3.05-3.2 (1H, m), 3.25-3.65 (5H, m), 3.72 (1H, dd, J=12.0 Hz, 5.5 Hz), 3.89 (1H, dd, J=12.0 Hz, 2.1 Hz), 5.65 (1H, d, J=7.9 Hz), 6.64 (1H, d, J=8.1 Hz), 6.76 (1H, d, J=6.5 Hz), 6.89 (1H, dd, J=8.1 Hz, 1.7 Hz), 6.98 (1H, d, J=1.7 Hz), 7.1-7.25 (2H, m)

Example 6

3-(β-D-Glucopyranosyloxy)-4-[2-(pyridin-4-yl) ethyl]-1H-indazole

To a solution of 3-(2,3,4,6-tetra-O-pivaloyl-β-D-glucopyranosyloxy)-4-[(E)-2-(pyridin-4-yl)vinyl]-1H-indazole (0.13 g) in tetrahydrofuran (6 mL) was added 10% palladium-carbon powder (26 mg), and the mixture was stirred at room temperature under a hydrogen atmosphere for 2 hours. The insoluble material was removed by filtration, and the filtrate was concentrated under reduced pressure to give 3-(2,3,4,6-tetra-O-pivaloyl-β-D-glucopyranosyloxy)-4-[2-(pyridin-4-yl)ethyl]-1H-indazole (0.13 g). This material was dissolved in methanol (6 mL). To the solution was added sodium methoxide (28% methanol solution, 0.12 mL), and the mixture was stirred at 50° C. overnight. To the reaction mixture was added acetic acid (0.05 mL), and the resulting mixture was purified by column chromatography on silica gel (eluent: dichloromethane/methanol=5/1 containing triethylamine at 3%) to give the title compound (70 mg).

$^1$H-NMR (CD$_3$OD) δ ppm: 3.0-3.15 (2H, m), 3.2-3.35 (1H, m), 3.35-3.6 (5H, m), 3.71 (1H, dd, J=12.2 Hz, 5.2 Hz), 3.88 (1H, dd, J=12.2 Hz, 1.9 Hz), 5.64 (1H, d, J=7.2 Hz), 6.76 (1H, d, J=6.8 Hz), 7.15-7.25 (2H, m), 7.3-7.4 (2H, m), 8.35-8.4 (2H, m)

Reference Example 5

4-(4-Bromophenyl)-2-butanone

To a suspension of 4-bromoaniline (1.8 g) in concentrated hydrochloric acid (4.5 mL) was added a solution of sodium nitrite (0.76 g) in water (1.68 mL) under ice-cooling, and the mixture was stirred at the same temperature for 1 hour to give diazonium salt. To a solution of 10% titanium (III) chloride in hydrochloric acid (20-30%) (25 mL) was added dropwise N,N-dimethylformamide (23 mL) over 30 minutes under bubbling of nitrogen gas under ice-cooling. To the mixture was added methyl vinyl ketone (1.28 mL). Then the above mixture containing diazonium salt was added to the reaction mixture under ice-cooling, and the resulting mixture was stirred for 1 hour. The reaction mixture was extracted with diethyl ether. The extract was washed with 3% aqueous sodium carbonate solution, water and brine successively, and dried over anhydrous magnesium sulfate. The solvent was removed under reduced pressure, and the residue was purified by column chromatography on silica gel (eluent: n-hexane/ethyl acetate=5/1) to give the title compound (1.27 g).

$^1$H-NMR (CDCl$_3$) δ ppm: 2.13 (3H, s), 2.7-2.8 (2H, m), 2.8-2.9 (2H, m), 7.0-7.1 (2H, m), 7.35-7.45 (2H, m)

Reference Example 6

2-Bromo-3-methoxycarbonyl-4-(2-phenylethyl)pyridine

A mixture of 4-phenyl-2-butanone (1 g), methyl cyanoacetate (0.77 g), acetic acid (0.29 mL), ammonium acetate (0.11 g) and toluene (10 mL) was heated for reflux overnight removing the generated water. The reaction mixture was poured into water, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane/ethyl acetate =3/1) to give methyl 2-cyano-3-methyl-5-phenyl-2-pentenate (1.35 g). To this material were added methanol (10 mL) and N,N-dimethylformamide dimethyl acetal (0.95 mL), and the mixture was heated for reflux overnight. The reaction mixture was concentrated under reduced pressure. To the residue were added acetic acid (8 mL) and a solution of 30% hydrobromic acid in acetic acid (5.9 g), and the mixture was stirred at room temperature for 6 hours. The reaction mixture was poured into ice water, and the resulting mixture was extracted with diethyl ether. The extract was washed with water twice, a saturated aqueous sodium hydrogen carbonate solution twice, water and brine successively, and dried over anhydrous magnesium sulfate. The solvent was removed under reduced pressure, and the residue was purified by column chromatography on silica gel (eluent: n-hexane/ethyl acetate=6/1) to give the title compound (1.7 g).

$^1$H-NMR (CDCl$_3$) δ ppm: 2.85-2.95 (4H, m), 3.97 (3H, s), 7.03 (1H, d, J=5.0 Hz), 7.1-7.15 (2H, m), 7.2-7.35 (3H, m), 8.26 (1H, d, J=5.0 Hz)

Reference Example 7

2-Bromo-4-[2-(4-hydroxyphenyl)ethyl]-3-methoxy-carbonyl-pyridine

The title compound was prepared in a similar manner to that described in Reference Example 6 using 4-(4-hydroxyphenyl)-2-butanone instead of 4-phenyl-2-butanone.

$^1$H-NMR (CDCl$_3$) δ ppm: 2.8-2.9 (4H, m), 3.97 (3H, s), 4.75 (1H, s), 6.7-6.8 (2H, m), 6.95-7.05 (3H, m), 8.25 (1H, d, J=5.0 Hz)

Reference Example 8

2-Bromo-4-[2-(4-bromophenyl)ethyl]-3-methoxycarbonyl-pyridine

The title compound was prepared in a similar manner to that described in Reference Example 6 using 4-(4-bromophenyl)-2-butanone instead of 4-phenyl-2-butanone.

$^1$H-NMR (CDCl$_3$) δ ppm: 2.8-2.9 (4H, m), 3.96 (3H, s), 6.95-7.05 (3H, m), 7.35-7.45 (2H, m), 8.27 (1H, d, J=5.1 Hz)

Reference Example 9

4-(2-Phenylethyl)-1H-pyrazolo[3,4-b]pyridin-3-ol

A mixture of 2-bromo-3-methoxycarbonyl-4-(2-phenylethyl)pyridine (1.42 g), hydrazine monohydrate (0.65 mL) and N-methylpyrrolidone (10 mL) was stirred at 100° C. for 2 hours. The reaction mixture was poured into water, and the precipitated crystals were collected by filtration, washed with water and dried under reduced pressure to give the title compound (0.74 g).

$^1$H-NMR (DMSO-d$_6$) δ ppm: 2.9-3.0 (2H, m), 3.15-3.25 (2H, m), 6.81 (1H, d, J=4.8 Hz), 7.15-7.35 (5H, m), 8.25 (1H, d, J=4.8 Hz)

Reference Example 10

4-[2-(4-Bromophenyl)ethyl]-1H-pyrazolo[3,4-b]pyridin-3-ol

The title compound was prepared in a similar manner to that described in Reference Example 9 using 2-bromo-4-[2-(4-bromophenyl)ethyl]-3-methoxycarbonylpyridine instead of 2-bromo-3-methoxycarbonyl-4-(2-phenylethyl)-pyridine.

$^1$H-NMR (CD$_3$OD) δ ppm: 2.95-3.05 (2H, m), 3.25-3.4 (2H, m), 6.78 (1H, d, J=4.8 Hz), 7.1-7.2 (2H, m), 7.35-7.45 (2H, m), 8.23 (1H, d, J=4.8 Hz)

Reference Example 11

4-[2-(4-Hydroxyphenyl)ethyl]-1H-pyrazolo[3,4-b]pyridin-3-ol

The title compound was prepared in a similar manner to that described in Reference Example 9 using 2-bromo-4-[2-(4-hydroxyphenyl)ethyl]-3-methoxycarbonylpyridine instead of 2-bromo-3-methoxycarbonyl-4-(2-phenylethyl)-pyridine.

$^1$H-NMR (DMSO-d$_6$) δ ppm: 2.8-2.9 (2H, m), 3.1-3.2 (2H, m), 6.6-6.7 (2H, m), 6.79 (1H, d, J=4.8 Hz), 6.95-7.05 (2H, m), 8.24 (1H, d, J=4.8 Hz), 9.12 (1H, s)

Reference Example 12

4-[2-(4-Benzyloxyphenyl)ethyl]-1H-pyrazolo[3,4-b]pyridin-3-ol

To a solution of 2-bromo-4-[2-(4-hydroxyphenyl)ethyl]-3-methoxycarbonylpyridine (1 g) in N,N-dimethylformamide (10 mL) were addedpotassium carbonate (0.49 g) and benzyl bromide (0.37 mL), and the mixture was stirred at room temperature for 3 days. The reaction mixture was poured into water, and the resulting mixture was extracted with diethyl ether. The extract was washed with water twice and brine, and dried over anhydrous magnesium sulfate. The solvent was removed under reduced pressure. To the residue were added N-methylpyrrolidone (10 mL) and hydrazine monohydrate (0.38 mL), and the mixture was stirred at 100° C. for 6 hours. The reaction mixture was poured into water, and the precipitated crystals were collected by filtration. The crystals were washed with water and dried under reduced pressure to give the title compound (0.71 g).

$^1$H-NMR (DMSO-d$_6$) δ ppm: 2.85-2.95 (2H, m), 3.1-3.25 (2H, m), 5.06 (2H, s), 6.8 (1H, d, J=4.8 Hz), 6.85-6.95 (2H, m), 7.1-7.2 (2H, m), 7.25-7.35 (1H, m), 7.35-7.5 (4H, m), 8.25 (1H, d, J=4.8 Hz)

Reference Example 13

4-{2-[4-(3-Benzyloxypropoxy)phenyl]ethyl}-1H-pyrazolo-[3,4-b]pyridin-3-ol

The title compound was prepared in a similar manner to that described in Reference Example 12 usingbenzyl 3-bromopropyl ether instead of benzyl bromide.

$^1$H-NMR (DMSO-d$_6$) δ ppm: 1.9-2.0 (2H, m), 2.85-2.95 (2H, m), 3.1-3.2 (2H, m), 3.58 (2H, t, J=6.3 Hz), 4.0 (2H, t, J=6.5 Hz), 4.48 (2H, s), 6.75-6.85 (3H, m), 7.1-7.2 (2H, m), 7.25-7.4 (5H, m), 8.25 (1H, d, J=4.7 Hz)

Example 7

4-(2-Phenylethyl)-3-(2,3,4,6-tetra-O-pivaloyl-β-D-glucopyranosyloxy)-1H-pyrazolo[3,4-b]pyridine A mixture of 4-(2-phenylethyl)-1H-pyrazolo[3,4-b]pyridin-3-ol (0.59 g), potassium carbonate (0.68 g), 2,3,4,6-tetra-O-pivaloyl-α-D-glucopyranosyl bromide (1.71 g) and acetonitrile (10 mL) was stirred at 50° C. overnight. The reaction mixture was poured into water, and the resulting mixture was extracted with diethyl ether. The extract was washed with water twice and brine, and dried over anhydrous magnesium sulfate. The solvent was removed under reduced pressure, and the residue was purified by column chromatography on silica gel (eluent: n-hexane/ethyl acetate=3/1-1/1) to give the title compound (0.22 g).

$^1$H-NMR (CDCl$_3$) δ ppm: 1.04 (9H, s), 1.13 (9H, s), 1.15 (9H, s), 1.18 (9H, s), 2.95-3.1 (2H, m), 3.15-3.25 (1H, m), 3.25-3.35 (1H, m), 3.95-4.05 (1H, m), 4.14 (1H, dd, J=12.4 Hz, 5.2 Hz), 4.22 (1H, dd, J=12.4 Hz, 2.0 Hz), 5.2-5.3 (1H, m), 5.4-5.55 (2H, m), 6.05 (1H, d, J=8.3 Hz), 6.71 (1H, d, J=4.9 Hz), 7.15-7.35 (5H, m), 8.31 (1H, d, J=4.9 Hz), 10.07 (1H, brs)

Example 8

4-[2-(4-Benzyloxyphenyl)ethyl]-3-(2,3,4,6-tetra-0-pivaloyl-β-D-glucopyranosyloxy)-1H-pyrazolo[3,4-b]pyridine The title compound was prepared in a similar manner to that described in Example 7 using 4-[2-(4-benzyloxyphenyl)-ethyl]-1H-pyrazolo[3,4-b]pyridin-3-ol instead of 4.-(2-phenylethyl)-1H-pyrazolo[3,4-b]pyridin-3-ol.

$^1$H-NMR (CDCl$_3$) δppm: 1.04 (9H, s), 1.13 (9H, s), 1.15 (9H, s), 1.17 (9H, s), 2.85-3.05 (2H, m), 3.1-3.3 (2H, m), 3.95-4.0 (1H, m), 4.13 (1H, dd, J=12.5 Hz, 5.2 Hz), 4.22 (1H, dd, J=12.5 Hz, 1.7 Hz), 5.05 (2H, s), 5.2-5.3 (1H, m), 5.4-5.55 (2H, m), 6.04 (1H, d, J=7.9 Hz), 6.7 (1H, d, J=4.8 Hz), 6.85-6.95 (2H, m), 7.05-7.15 (2H, m), 7.25-7.5 (5H, m), 8.3 (1H, d, J=4.8 Hz), 9.59 (1H, brs)

Reference Example 14

4-{2-[4-(3-Benzyloxypropoxy)phenyl]ethyl}-3-(2,3,4,6-tetra-O-pivaloyl-β-D-glucopyranosyloxy)-1H-pyrazolo-[3,4-b]pyridine The title compound was prepared in a similar manner to that described in Example 7 using 4-{2-[4-(3-benzyloxypropoxy)phenyl]ethyl}-1H-pyrazolo[3,4-b]pyridin-3-ol instead of 4-(2-phenylethyl)-1H-pyrazolo[3,4-b]pyridin-3-ol.

$^1$H-NMR (CDCl$_3$) δ ppm: 1.04 (9H, s), 1.13 (9H, s), 1.15 (9H, s), 1.17 (9H, s), 2.05-2.15 (2H, m), 2.85-3.05 (2H, m), 3.1-3.3 (2H, m), 3.67 (2H, t, J=6.1 Hz), 3.95-4.0 (1H, m), 4.06 (2H, t, J=6.3 Hz), 4.13 (1H, dd, J=12.4 Hz, 4.8 Hz), 4.22 (1H, dd, J=12.4 Hz, 1.9 Hz), 4.53 (2H, s), 5.2-5.3 (1H, m), 5.4-5.55 (2H, m), 6.04 (1H, d, J=7.9 Hz), 6.7 (1H, d, J=4.8 Hz), 6.75-6.85 (2H, m), 7.0-7.1 (2H, m), 7.25-7.35 (5H, m), 8.29 (1H, d, J=4.8 Hz), 9.6 (1H, s)

Example 9

4-[2-(4-Bromophenyl)ethyl]-3-(2,3,4,6-tetra-O-pivaloyl-β-D-glucopyranosyloxy)-1H-pyrazolo[3,4-b]pyridine The title compound was prepared in a similar manner to that described in Example 7 using 4-[2-(4-bromophenyl)ethyl]-1H-pyrazolo [3, 4-b]pyridin-3-ol instead of 4-(2-phenylethyl)-1H-pyrazolo[3,4-b]pyridin-3-ol.

$^1$H-NMR (CD$_3$OD) δ ppm: 1.05 (9H, s), 1.08 (9H, s), 1.16 (9H, s), 1.17 (9H, s), 2.9-3.1 (2H, m), 3.1-3.25 (1H, m), 3.25-3.4 (1H, m), 4.05-4.2 (2H, m), 4.2-4.3 (1H, m), 5.2-5.4 (2H, m), 5.5-5.6 (1H, m), 6.13 (1H, d, J=7.9 Hz), 6.85 (1H, d, J=4.8 Hz), 7.1-7.2 (2H, m), 7.35-7.45 (2H, m), 8.28 (1H, d, J=4.8 Hz)

Example 10

4-[2-(4-Hydroxyphenyl)ethyl]-3-(2,3,4,6-tetra-O-pivaloyl-β-D-glucopyranosyloxy)-1H-pyrazolo[3,4-b]pyridine 4-[2-(4-Hydroxyphenyl)ethyl]-1H-pyrazolo[3,4-b]-pyridin-3-ol (3.48 g) was stirred at 100° C. to be dissolved in N,N-dimethylformamide (55 mL). The solution was cooled to room temperature. To the solution were added potassium carbonate (3.77 g) and 2,3,4,6-tetra-O-pivaloyl-α-D-glucopyranosyl bromide (9.48 g), and the mixture was stirred at room temperature overnight. The reaction mixture was poured into water, and the resulting mixture was extracted with diethyl ether. The extract was washed with water and brine, and dried over anhydrous sodium sulfate. The solvent was removed under reduced pressure, and the residue was purified by column chromatography on silica gel (eluent: n-hexane/ethyl acetate=3/2-1/1-2/3) to give the title compound (2.26 g).

$^1$H-NMR (CDCl$_3$) δ ppm: 1.05 (9H, s), 1.12 (9H, s), 1.15 (9H, s), 1.18 (9H, s), 2.9-3.0 (2H, m), 3.1-3.35 (2H, m), 3.95-4.05 (1H, m), 4.15-4.25 (2H, m), 5.07 (1H, brs), 5.2-5.3 (1H, m), 5.35-5.55 (2H, m), 6.01 (1H, d, J=8.0 Hz), 6.65-6.75 (3H, m), 6.95-7.05 (2H, m), 8.31 (1H, d, J=4.8 Hz), 10.06 (1H, s)

Example 11

3-(β-D-Glucopyranosyloxy)-4-(2-phenylethyl)-1H-pyrazolo-[3,4-b]pyridine

To a solution of 4-(2-phenylethyl)-3-(2,3,4,6-tetra-O-pivaloyl-β-D-glucopyranosyloxy)-1H-pyrazolo-[3,4-b]pyridine (0.26 g) in methanol (5 mL) was added sodium methoxide (28% methanol solution, 0.067 mL), and the mixture was stirred at 50° C. for 5 hours. To the reaction mixture was added acetic acid (0.04 mL), and the resulting mixture was purified by column chromatography on silica gel (eluent: dichloromethane/methanol=10/1-5/1) to give the title compound (91 mg)

$^1$H-NMR (CD$_3$OD) δ ppm: 2.95-3.15(2H,m),3.2-3.35 (1H,m),3.35-3.55 (4H,m),3.55-3.65 (1H, m), 3.71 (1H, dd, J=12.2 Hz, 5.2 Hz), 3.88 (1H, dd, J=12.2 Hz, 2.2 Hz), 5.72 (1H, d, J=7.8 Hz), 6.87 (1H, d, J=4.8 Hz), 7.1-7.2 (1H, m), 7.2-7.3 (4H, m), 8.27 (1H, d, J=4.8 Hz)

Example 12

1-Carbamoylmethyl-3-(β-D-glucopyranosyloxy)-4-[2-(4-hydroxyphenyl)ethyl]-1H-pyrazolo[3,4-b]pyridine To a solution of 4-[2-(4-benzyloxyphenyl)ethyl]-3-(2,3,4,6-tetra-O-pivaloyl-β-D-glucopyranosyloxy)-1H-pyrazolo [3,4-b]pyridine (73 mg) in acetone (4 mL) were added cesium carbonate (56 mg), 2-bromoacetoamide (18 mg) and a catalytic amount of sodium iodide, and the mixture was stirred at room temperature overnight. The reaction mixture was purified by column chromatography on silica gel (eluent: dichloromethane/methanol=30/1-10/1) to give 4-[2-(4-benzyloxyphenyl)ethyl]-1-carbamoylmethyl-3-(2,3,4,6-tetra-O-pivaloyl-β-D-glucopyranosyloxy)-1H-pyrazolo[3,4-b]pyridine (63 mg). This material was dissolved in methanol (4 mL). To the solution was added sodium methoxide (28% methanol solution, 0.027 mL), and the mixture was stirred at 50° C. overnight. The reaction mixture was cooled to room temperature, and the precipitated crystals were collected by filtration. The crystals were washed with methanol and dried under reduced pressure to give 4-[2-(4-benzyloxyphenyl) ethyl]-1-carbamoylmethyl-3-(β-D-glucopyranosyloxy)-1H-pyrazolo-[3,4-b]pyridine (25 mg). To this material were added methanol (1 mL), tetrahydrofuran (1 mL) and 10% palladium-carbon powder (10 mg), and the mixture was stirred at room temperature under 5 a hydrogen atmosphere for 5 hours. The insoluble material was removed by filtration, and the filtrate was concentrated under reduced pressure to give the title compound (13 mg).

¹H-NMR (CD₃OD) δ ppm: 2.85-3.0 (2H,m), 3.1-3.65 (6H,m), 3.69 (1H, dd, J=12.0 Hz, 5.6 Hz), 3.87 (1H, dd, J=12.0 Hz, 2.1 Hz), 4.98 (1H, d, J=17.2 Hz), 5.03 (1H, d, J=17.2 Hz), 5.75 (1H, d, J=7.9 Hz), 6.65-6.7 (2H, m), 6.9 (1H, d, J=4.9 Hz), 7.0-7.1 (2H, m), 8.3 (1H, d, J=4.9 Hz)

Example 13

4-[2-(4-Benzyloxyphenyl)ethyl]-1-carboxymethyl-3-(β-D-glucopyranosyloxy)-1H-pyrazolo[3,4-b]pyridine To a solution of 4-[2-(4-benzyloxyphenyl)ethyl]-3-(2,3,4,6-tetra-O-pivaloyl-β-D-glucopyranosyloxy)-1H-pyrazolo[3,4-b]pyridine (0.43 g) in acetone (7 mL) were added cesium carbonate (0.33 g), methyl 2-bromoacetate (0.072 mL) and a catalytic amount of sodium iodide, and the mixture was stirred at room temperature overnight. The reaction mixture was purified by column chromatography on silica gel (eluent:
n-hexane/ethyl acetate=2/1-3/2) to give 4-[2-(4-benzyloxy-25 phenyl)ethyl]-1-methoxycarbonylmethyl-3-(2,3,4,6-tetra-O-pivaloyl-β-D-glucopyranosyloxy)-1H-pyrazolo[3,4-b]pyridine (0.42 g). This material was dissolved in a mixed solvent of methanol (10 mL) and tetrahydrofuran (5 mL). To the solution was added sodium methoxide (28% methanol solution, 0.3 mL), and the mixture was stirred at 55° C. for 4 hours. The reaction mixture was concentrated under reduced pressure. To the residue was added 2 mol/L aqueous sodium hydroxide solution (15 mL), and the mixture was stirred at room temperature overnight. To the reaction mixture was added 2 mol/L hydrochloric acid (17 mL), and the mixture was stirred at room temperature for 30 minutes. The mixture was extracted with ethyl acetate. The extract was washed with water and brine, and dried over anhydrous sodium sulfate. The solvent was removed under reduced pressure to give the title compound (0.16 g).

¹H-NMR (CD₃OD) δ ppm: 2.9-3.1 (2H, m), 3.15-3.65 (6H, m), 3.71 (1H, dd, J=12.1 Hz, 5.1 Hz), 3.86 (1H, dd, J=12.1 Hz, 2.3 Hz), 5.0-5.15 (4H, m), 5.74 (1H, d, J=8.1 Hz), 6.85-6.95 (3H, m), 7.15-7.2 (2H, m), 7.25-7.45 (5H, m), 8.29 (1H, d, J=4.6 Hz)

Example 14

3-(β-D-Glucopyranosyloxy)-4-[2-(4-hydroxyphenyl)ethyl]-1-(N,N-dimethylcarbamoylmethyl)-1H-pyrazolo[3,4-b]pyridine To a solution of 4-[2-(4-benzyloxyphenyl)ethyl]-1-carboxymethyl-3-(β-D-glucopyranosyloxy)-1H-pyrazolo-[3,4-b]pyridine (50 mg) in N,N-dimethylformamide (2 mL) were added dimethylamine hydrochloride (9 mg), 1-hydroxybenzotriazole (14 mg), 1-ethyl-3-(3-dimethylaminopropyl)-carbodiimide hydrochloride (34 mg) and triethylamine (0.049 mL), and the mixture was stirred at room temperature overnight. The reaction mixture was poured into water, and the resulting mixture was extracted with ethyl acetate. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: dichloromethane/methanol=10/1–8/1) to give 4-[2-(4-benzyloxyphenyl)ethyl]-3-(β-D-glucopyranosyloxy)-1-(N,N-dimethylcarbamoylmethyl)-1H-pyrazolo[3,4-b]pyridine (27 mg). This material was dissolved in methanol (4 mL). To the solution was added 10% palladium-carbon powder (10 mg), and the mixture was stirred at room temperature under a hydrogen atmosphere for 3 hours. The insoluble material was removed by filtration, and the solvent of the filtrate was removed under reduced pressure to give the title compound (20 mg).

¹H-NMR (CD₃OD) δ ppm: 2.85-3.05 (5H, m), 3.1-3.55 (8H, m), 3.55-3.65 (1H, m), 3.69 (1H, dd, J=12.2 Hz, 5.5 Hz), 3.86 (1H, dd, J=12.2 Hz, 1.8 Hz), 5.24 (1H, d, J=17.0 Hz), 5.28 (1H, d, J=17.0 Hz), 5.71 (1H, d, J=7.9 Hz), 6.65-6.75 (2H, m), 6.88 (1H, d, J=4.9 Hz), 7.0-7.1 (2H, m), 8.27 (1H, d, J=4.9 Hz)

Example 15

3-(β-D-Glucopyranosyloxy)-4-[2-(4-hydroxyphenyl)ethyl]-1-(N-phenylcarbamoylmethyl)-1H-pyrazolo[3,4-b]pyridine The title compound was prepared in a similar manner to that described in Example 14 using aniline instead of dimethylamine hydrochloride.

¹H-NMR (CD₃OD) δ ppm: 2.85-3.05 (2H, m), 3.15-3.65 (6H, m), 3.69 (1H, dd, J=12.0 Hz, 5.3 Hz), 3.85 (1H, dd, J=12.0 Hz, 1.8 Hz), 5.15 (1H, d, J=17.0 Hz), 5.22 (1H, d, J=17.0 Hz), 5.76 (1H, d, J=7.9 Hz), 6.65-6.75 (2H, m), 6.91 (1H, d, J=5.1 Hz), 7.0-7.15 (3H, m), 7.25-7.35 (2H, m), 7.5-7.6 (2H, m), 8.31 (1H, d, J=5.1 Hz)

Example 16

3-(β-D-Glucopyranosyloxy)-4-[2-(4-hydroxyphenyl)ethyl]-1H-pyrazolo[3,4-b]pyridine To a solution of 4-[2-(4-benzyloxyphenyl)ethyl]-3-(2,3,4,6-tetra-O-pivaloyl-β-D-glucopyranosyloxy)-1H-pyrazolo[3,4-b]pyridine (49 mg) in methanol (4 mL) was added sodium methoxide (0.056 mL), and the mixture was stirred at 50° C. for 5 hours. To the reaction mixture was added acetic acid (0.033 mL), and the resulting mixture was purified by column chromatography on silica gel (eluent: dichloromethane/methanol=10/1–5/1) to give 4-[2-(4-benzyloxyphenyl)ethyl]-3-(β-D-glucopyranosyloxy)-1H-pyrazolo[3,4-b]pyridine (25 mg). This material was dissolved in methanol (4 mL). To the solution was added 10% palladium-carbon powder (10 mg), and the mixture was stirred at room temperature under a hydrogen atmosphere overnight. The insoluble material was removed by filtration, and the filtrate was concentrated under reduced pressure to give the title compound (16 mg).

¹H-NMR (CD₃OD) δ ppm: 2.85-3.05 (2H, m), 3.1-3.6 (6H, m), 3.71 (1H, dd, J=12.0 Hz, 5.2 Hz), 3.88 (1H, dd, J=12.0 Hz, 2.1 Hz), 5.7 (1H, d, J=8.0 Hz), 6.65-6.75 (2H, m), 6.86 (1H, d, J=4.6 Hz), 7.0-7.1 (2H, m), 8.27 (1H, d, J=4.6 Hz)

Reference Example 15

1-(2-Benzyloxyethyl)-4-(2-phenylethyl)-3-(2,3,4,6-tetra-O-pivaloyl-β-D-glucopyranosyloxy)-1H-pyrazolo[3,4-b]pyridine To a solution of 4-(2-phenylethyl)-3-(2,3,4,6-tetra-O-pivaloyl-β-D-glucopyranosyloxy)-1H-pyrazolo[3,4-b]pyridine (98 mg) in acetone (4 mL) were added cesium carbonate (87 mg), benzyl 2-bromoethyl ether (0.032 mL) and a catalytic amount of sodium iodide, and the mixture was stirred at room temperature for 3 days. The reaction mixture was purified by column chromatography on silica gel (eluent: n-hexane/ethyl acetate=3/1) to give the title compound (0.11 g).

$^1$H-NMR (CDCl$_3$) δ ppm: 1.02 (9H, s), 1.12 (9H, s), 1.15 (9H, s), 1.17 (9H, s), 2.9-3.1 (2H, m), 3.1-3.35 (2H, m), 3.85-3.95 (3H, m), 4.05-4.15 (1H, m), 4.16 (1H, dd, J=12.8 Hz, 1.8 Hz), 4.45-4.7 (4H, m), 5.2-5.3 (1H, m), 5.35-5.55 (2H, m), 6.02 (1H, d, J=7.8 Hz), 6.66 (1H, d, J=4.8 Hz), 7.15-7.4 (10H, m), 8.28 (1H, d, J=4.8 Hz)

Example 17

3-(β-D-Glucopyranosyloxy)-1-(2-hydroxyethyl)-4-(2-phenylethyl)-1H-pyrazolo[3,4-b]pyridine The title compound was prepared in a similar manner to that described in Example 16 using 1-(2-benzyloxyethyl)-4-(2-phenylethyl)-3-(2,3,4,6-tetra-O-pivaloyl-β-D-glucopyranosyloxy)-1H-pyrazolo[3,4-b]pyridine instead of 4-[2-(4-benzyloxyphenyl)ethyl]-3-(2,3,4,6-tetra-O-pivaloyl-β-D-glucopyranosyloxy)-1H-pyrazolo[3,4-b]pyridine.

$^1$H-NMR (CD$_3$OD) δ ppm: 2.95-3.15 (2H, m), 3.2-3.55 (5H, m), 3.55-3.65 (1H, m), 3.69 (1H, dd, J=12.1 Hz, 5.6 Hz), 3.88 (1H, dd, J=12.1 Hz, 2.2 Hz), 3.95 (2H, t, J=5.6 Hz), 4.4-4.5 (2H, m), 5.77 (1H, d, J=7.8 Hz), 6.86 (1H, d, J=4.9 Hz), 7.1-7.2 (1H, m), 7.2-7.3 (4H, m), 8.28 (1H, d, J=4.9 Hz)

Example 18

4-{2-[4-(3-Hydroxypropoxy)phenyl]ethyl}-3-(2,3,4,6-tetra-O-pivaloyl-β-D-glucopyranosyloxy)-1H-pyrazolo[3,4-b]pyridine 4-{2-[4-(3-Benzyloxypropoxy)phenyl]ethyl}-3-(2,3,4,6-tetra-O-pivaloyl-β-D-glucopyranosyloxy)-1H-pyrazolo-[3,4-b]pyridine (0.4 g) was dissolved in a mixed solvent of tetrahydrofuran (6 mL) and methanol (6 mL). To the solution was added 10% palladium-carbon powder (160 mg), and the mixture was stirred at room temperature under a hydrogen atmosphere for 3 hours. The insoluble material was removed by filtration, and the filtrate was concentrated under reduced pressure to give the title compound (0.36 g).

$^1$H-NMR (CDCl$_3$) δ ppm: 1.05 (9H, s), 1.13 (9H, s), 1.15 (9H, s), 1.17 (9H, s), 2.0-2.1 (2H, m), 2.85-3.05 (2H, m), 3.1-3.3 (2H, m), 3.8-3.9 (2H, m), 3.95-4.05 (1H, m), 4.05-4.25 (4H, m), 5.2-5.3 (1H, m), 5.4-5.55 (2H, m), 6.04 (1H, d, J=7.9 Hz), 6.71 (1H, d, J=4.7 Hz), 6.8-6.85 (2H, m), 7.05-7.15 (2H, m), 8.31 (1H, d, J=4.7 Hz), 9.77 (1H, s)

Example 19

4-[2-(4-{3-[1-Carbamoyl-1-(methyl)ethylamino]propoxy}-phenyl)ethyl]-3-(β-D-glucopyranosyloxy)-1H-pyrazolo-[3,4-b]pyridine To a solution of 4-{2-[4-(3-hydroxypropoxy)phenyl]-ethyl}-3-(2,3,4,6-tetra-O-pivaloyl-β-D-glucopyranosyloxy)-1H-pyrazolo[3,4-b]pyridine (0.22 g) and triethylamine (0.056 mL) in dichloromethane (4 mL) was added methanesulfonyl chloride (0.025 mL) under ice-cooling, and the mixture was stirred at room temperature for 2 hours. The reaction mixture was poured into water, and the resulting mixture was extracted with diethyl ether. The extract was washed with water and brine, and dried over anhydrous magnesium sulfate. The solvent was removed under reduced pressure to give 4-{2-[4-(3-methanesulfonyloxy-propoxy)phenyl]ethyl}-3-(2,3,4,6-tetra-O-pivaloyl-β-D-glucopyranosyloxy)-1H-pyrazolo[3,4-b]pyridine. This material was dissolved in a mixed solvent of acetonitrile (3 mL) and ethanol (3 mL). To the solution were added 2-amino-2-methylpropionamide (0.14 g) and a catalytic amount of sodium iodide, and the mixture was stirred at 60° C. for 3 days. The reaction mixture was poured into a saturated aqueous sodium hydrogen carbonate solution, and the resulting mixture was extracted with ethylacetate. The extract was washed with brine and dried over anhydrous magnesium sulfate. The solvent was removed under reduced pressure, and the residue was purified by column chromatography on silica gel (eluent: dichloromethane/methanol =20/1–10/1) to give 4-[2-(4-{3-[1-carbamoyl-1-(methyl)ethylamino]propoxy}phenyl)ethyl]-3-(2,3,4,6-tetra-O-pivaloyl-β-D-glucopyranosyloxy)-1H-pyrazolo[3,4-b]-pyridine (0.12 g). This material was dissolved in methanol (6 mL). To the solution was added sodium methoxide (28% methanol solution, 0.077 mL), and the mixture was stirred at 50° C. overnight. To the reaction mixture was added acetic acid (0.034 mL), and the resulting mixture was concentrated under reduced pressure. The residue was purified by solid phase extraction on ODS (washing solvent: distilled water, eluent: methanol) to give the title compound (62 mg).

$^1$H-NMR (CD$_3$OD) δ ppm: 1.37 (6H, s), 1.9-2.05 (2H, m), 2.77 (2H, t, J=7.1 Hz), 2.9-3.05 (2H, m), 3.15-3.65 (6H, m), 3.71 (1H, dd, J=12.1 Hz, 5.0 Hz), 3.88 (1H, dd, J=12.1 Hz, 2.0 Hz), 4.04 (2H, t, J=6.0 Hz), 5.71 (1H, d, J=7.8 Hz), 6.8-6.9 (3H, m), 7.1-7.2 (2H, m), 8.26 (1H, d, J=5.0 Hz)

Example 20

3-(β-D-Glucopyranosyloxy)-4-[2-(4-{3-[4-(2-hydroxyethyl)-piperazin-1-yl]propoxy}phenyl)ethyl]-1H-pyrazolo[3,4-b]-pyridine The title compound was prepared in a similar manner to that described in Example 19 using 1-(2-hydroxyethyl)piperazine instead of 2-amino-2-methylpropionamide.

$^1$H-NMR (CD$_3$OD) δ ppm: 1.9-2.05 (2H, m), 2.4-3.05 (14H, m), 3.15-3.65 (6H, m), 3.65-3.75 (3H, m), 3.88 (1H, dd, J=12.1 Hz, 2.0 Hz), 4.0 (2H, t, J=6.0 Hz), 5.7 (1H, d, J=8.1 Hz), 6.75-6.9 (3H, m), 7.1-7.2 (2H, m), 8.26 (1H, d, J=4.6 Hz)

Example 21

4-(2-{4-[(E)-3-Carboxyprop-1-enyl]phenyl}ethyl)-3-(2,3,4,6-tetra-O-pivaloyl-β-D-glucopyranosyloxy)-1H-pyrazolo[3,4-b]-pyridine A mixture of 4-[2-(4-bromophenyl)ethyl]-3-(2,3,4,6-tetra-O-pivaloyl-β-D-glucopyranosyloxy)-1H-pyrazolo[3,4-b]-pyridine (0.27 g), 3-butenoic acid (56 mg), triethylamine (0.23 mL), palladium (II) acetate (7 mg) and tris(2-methyl-phenyl)phosphine (20 mg) in acetonitrile (5 mL) was heated for reflux under an argon atmosphere overnight. The reaction mixture was diluted with dichloromethane, and the insoluble material was removed by filtration. The filtrate was washed with 1 mol/L hydrochloric acid, water and brine successively, and dried over anhydrous magnesium sulfate. The solvent was removed under reduced pressure, and the residue was purified by column chromatography on silica gel (eluent: dichloromethane/methanol=20/1) to give the title compound (0.19 g).

¹H-NMR (CDCl₃) δ ppm: 1.05 (9H, s), 1.13 (9H, s), 1.15 (9H, s), 1.17 (9H, s), 3.0-3.1 (2H, m), 3.15-3.35 (4H, m), 3.95-4.05 (1H, m), 4.1-4.2 (1H, m), 4.22 (1H, dd, J=12.5 Hz, 1.9 Hz), 5.2-5.3 (1H, m), 5.4-5.55 (2H, m), 6.03 (1H, d, J=7.8 Hz), 6.2-6.3 (1H, m), 6.47 (1H, d, J=15.9 Hz), 6.56 (1H, d, J=4.8 Hz), 6.95-7.05 (2H, m), 7.2-7.25 (2H, m), 8.15 (1H, d, J=4.8 Hz)

Example 22

3-(β-D-Glucopyranosyloxy)-4-[2-(4-{3-[(S)-2-hydroxy-1-(methyl)ethylcarbamoyl]propyl}phenyl)ethyl]-1H-pyrazolo-[3,4-b]pyridine To a solution of 4-(2-{4-[(E)-3-carboxyprop-1-enyl]-phenyl}ethyl)-3-(2,3,4,6-tetra-O-pivaloyl-β-D-glucopyranosyloxy) -1H-pyrazolo[3,4-b]pyridine (0.19 g) in N,N-dimethyl-formamide (5 mL) were added (S)-2-amino-1-propanol (52 mg), 1-hydroxybenzotriazole (94 mg), 1-ethyl-3-(3-dimethylamino-propyl)carbodiimide hydrochloride (0.13 g) and triethylamine (0.03 mL), and the mixture was stirred at room temperature overnight. The reaction mixture was poured into water, and the resulting mixture was extracted with diethyl ether. The extract was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: dichloromethane/methanol=30/1) to give 4-[2-(4-((E)-3-[(S)-2-hydroxy-1-(methyl)ethylcarbamoyl]prop-1-enyl)phenyl)ethyl]-3-(2,3,4,6-tetra-O-pivaloyl-β-D-glucopyranosyloxy)-1H-pyrazolo[3,4-b]pyridine (78 mg). The obtained material (60 mg) was dissolved in methanol (1.3 mL). To the solution was added 10% palladium-carbon powder (6 mg), and the mixture was stirred at room temperature under a hydrogen atmosphere for 2 hours. The insoluble material was removed by filtration, and the solvent of the filtrate was removed under reduced pressure to give 4-[2-(4-{3-[(S)-2-hydroxy-1-(methyl)-ethylcarbamoyl]propyl}phenyl)ethyl]-3-(2,3,4,6-tetra-O-pivaloyl-β-D-glucopyranosyloxy)-1H-pyrazolo[3,4-b]pyridine (58 mg). This material was dissolved in methanol (1 mL). To the solution was added sodium methoxide (28% methanol solution, 0.03 mL), and the mixture was stirred at 50° C. overnight. To the reaction mixture was added acetic acid (0.07 mL), and the resulting mixture was concentrated under reduced pressure. The residue was purified by solid phase extraction on ODS (washing solvent: distilled water, eluent: methanol) to give the title compound (26 mg).

¹H-NMR (CD₃OD) δ ppm: 1.12 (3H, d, J=6.7 Hz), 1.85-1.95 (2H, m), 2.19 (2H, t, J=7.6 Hz), 2.59 (2H, t, J=7.7 Hz), 2.9-3.1 (2H, m), 3.15-3.3 (1H, m), 3.3-3.65 (7H, m), 3.71 (1H, dd, J=12.1 Hz, 5.2 Hz), 3.85-4.0 (2H, m), 5.72 (1H, d, J=7.8 Hz), 6.87 (1H, d, J=4.9 Hz), 7.05-7.15 (2H, m), 7.15-7.25 (2H, m), 8.27 (1H, d, J=4.9 Hz)

Example 23

3-(2,3,4,6-Tetra-O-pivaloyl-β-D-glucopyranosyloxy)-4-[2-(4-pivaloyloxyphenyl)ethyl]-1H-pyrazolo[3,4-b]pyridine To a solution of 4-[2-(4-hydroxyphenyl)ethyl]-3-(2,3,4,6-tetra-O-pivaloyl-β-D-glucopyranosyloxy)-1H-pyrazolo[3,4-b]pyridine (1.6 g) in dichloromethane (20 mL) were added triethylamine (0.44 mL) and pivaloyl chloride (0.31 mL), and the mixture was stirred at room temperature for 1 hour. The reaction mixture was poured into 0.5 mol/L hydrochloric acid, and the resulting mixture was extracted with diethyl ether. The extract was washed with water and brine, and dried over anhydrous sodium sulfate. The solvent was removed under reduced pressure, and the residue was purified by column chromatography on silica gel (eluent: n-hexane/ethyl acetate =2/1–1/1) to give the title compound (1.76 g).

¹H-NMR (CDCl₃) δ ppm: 1.04 (9H, s), 1.13 (9H, s), 1.15 (9H, s), 1.18 (9H, s), 1.35 (9H, s), 2.9-3.1 (2H, m), 3.15-3.35 (2H, m), 3.95-4.05 (1H, m), 4.1-4.2 (1H, m), 4.23 (1H, dd, J=12.6 Hz, 1.7 Hz), 5.2-5.3 (1H, m), 5.4-5.55 (2H, m), 6.06 (1H, d, J=7.9 Hz), 6.7 (1H, d, J=4.8 Hz), 6.95-7.0 (2H, m), 7.15-7.2 (2H, m), 8.32 (1H, d, J=4.8 Hz), 10.3 (1H, s)

Example 24

3-(β-D-Glucopyranosyloxy)-4-[2-(4-hydroxyphenyl)ethyl]-1-isopropyl-1H-pyrazolo[3,4-b]pyridine To a solution of 3-(2,3,4,6-tetra-O-pivaloyl-β-D-glucopyranosyloxy)-4-[2-(4-pivaloyloxyphenyl)ethyl]-1H-pyrazolo-[3,4-b]pyridine (84 mg) in acetone (1.5 mL) were added cesium carbonate (0.11 g) and 2-iodopropane (0.03 mL), and the mixture was stirred at room temperature for 2 days. The reaction mixture was purified by column chromatography on silica gel (eluent: n-hexane/ethyl acetate=10/1–2/1) to give 1-isopropyl-3-(2,3,4,6-tetra-O-pivaloyl-β-D-glucopyranosyloxy)-4-[2-(4-pivaloyloxyphenyl)ethyl]-1H-pyrazolo[3,4-b]pyridine (61 mg). This material was dissolved in methanol (2 mL). To the solution was added sodium methoxide (28% methanol solution, 0.04 mL), and the mixture was stirred at 60° C. overnight. The reaction mixture was concentrated under reduced pressure, and the residue was purified by solid phase extraction on ODS (washing solvent: distilled water, eluent: methanol) to give the title compound (26 mg).

¹H-NMR (CD₃OD) δ ppm: 1.48 (6H, d, J=6.6 Hz), 2.85-3.05 (2H, m), 3.1-3.4 (2H, m), 3.4-3.65 (4H, m), 3.7 (1H, dd, J=11.9 Hz, 5.0 Hz), 3.8-3.9 (1H, m), 5.05-5.2 (1H, m), 5.78 (1H, d, J=7.4 Hz), 6.65-6.75 (2H, m), 6.83 (1H, d, J=4.7 Hz), 7.0-7.15 (2H, m), 8.25 (1H, d, J=4.7 Hz)

Example 25

3-(β-D-Glucopyranosyloxy)-4-[2-(4-hydroxyphenyl)ethyl]-1-(2-methoxyethyl)-1H-pyrazolo[3,4-b]pyridine The title compound was prepared in a similar manner to that described in Example 24 using 1-bromo-2-methoxyethane instead of 2-iodopropane.

¹H-NMR (CD₃OD) δ ppm: 2.85-3.05 (2H, m), 3.15-3.4 (5H, m), 3.4-3.65 (4H, m), 3.71 (1H, dd, J=12.1 Hz, 5.2 Hz), 3.81 (2H, t, J=5.7 Hz), 3.87 (1H, dd, J=12.1 Hz, 2.1 Hz), 4.4-4.55 (2H, m), 5.75 (1H, d, J=7.7 Hz), 6.65-6.75 (2H, m), 6.84 (1H, d, J=4.7 Hz), 7.0-7.1 (2H, m), 8.27 (1H, d, J=4.7 Hz)

Example 26

1-Benzyl-3-(β-D-glucopyranosyloxy)-4-[2-(4-hydroxyphenyl)-ethyl]-1H-pyrazolo[3,4-b]pyridine The title compound was prepared in a similar manner to that described in Example 24 using benzyl bromide instead of 2-iodopropane.

¹H-NMR (CD₃OD) δ ppm: 2.85-3.05 (2H, m), 3.1-3.65 (6H, m), 3.65-3.75 (1H, m), 3.8-3.9 (1H, m), 5.48 (1H, d, J=15.7 Hz), 5.57 (1H, d, J=15.7 Hz), 5.73 (1H, d, J=7.9 Hz), 6.6-6.7 (2H, m), 6.87 (1H, d, J=4.9 Hz), 7.0-7.3 (7H, m), 8.3 (1H, d, J=4.9 Hz)

Example 27

3-(β-D-Glucopyranosyloxy)-4-[2-(4-hydroxyphenyl)ethyl]-1-(2-phenylethyl)-1H-pyrazolo[3,4-b]pyridine The title compound was prepared in a similar manner to that described in Example 24 using 1-bromo-2-phenylethane instead of 2-iodopropane.

¹H-NMR (CD₃OD) δ ppm: 2.85-3.0 (2H, m), 3.1-3.25 (3H, m), 3.25-3.4 (1H, m), 3.4-3.65 (4H, m), 3.74 (1H, dd, J=12.2 Hz, 4.8 Hz), 3.89 (1H, dd, J=12.2 Hz, 2.3 Hz), 4.45-4.6 (2H, m), 5.75 (1H, d, J=7.5 Hz), 6.65-6.75 (2H, m), 6.77 (1H, d, J=4.9 Hz), 7.1-7.25 (7H, m), 8.18 (1H, d, J=4.9 Hz)

Example 28

1-(3-Carboxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine To a solution of benzyl alcohol (1 mL) and triethylamine (2.69 mL) in dichloromethane (15 mL) was added 4-bromobutyryl chloride (1.68 mL), and the mixture was stirred at room temperature for 2 hours. The reaction mixture was poured into 1 mol/L hydrochloric acid, and the resulting mixture was extracted with diethyl ether. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=8/1) to give benzyl 4-bromobutyrate (2.45 g). To a solution of 3-(2,3,4,6-tetra-O-pivaloyl-β-D-glucopyranosyloxy)-4-[2-(4-pivaloyloxyphenyl)ethyl]-1H-pyrazolo[3,4-b]pyridine (0.17 g) in acetone (3 mL) were added cesium carbonate (0.16 g), benzyl 4-bromobutyrate (0.1 g) and a catalytic amount of sodium iodide, and the mixture was stirred at room temperature for 2 days. The reaction mixture was purified by column chromatography on silica gel (eluent: n-hexane/ethyl acetate=10/1–3/1) to give 1-(3-benzyloxycarbonylpropyl)-3-(β-D-glucopyranosyloxy)-4-[2-(4-pivaloyloxyphenyl)ethyl]-1H-pyrazolo[3,4-b]pyridine (0.14 g). This material was dissolved in tetrahydrofuran (5 mL). To the solution was added 10% palladium-carbon powder (50 mg), and the mixture was stirred at room temperature under a hydrogen atmosphere for 3 hours. The insoluble material was removed by filtration, and the filtrate was concentrated under reduced pressure. The residue was purified by column chromatography on silica gel (eluent: n-hexane/ethyl acetate=1/2-dichloromethane/methanol=15/1) to give the title compound (95 mg).

¹H-NMR (CDCl₃) δ ppm: 1.04 (9H, s), 1.13 (9H, s), 1.15 (9H, s), 1.17 (9H, s), 1.35 (9H, s), 2.15-2.3 (2H, m), 2.3-2.45 (2H, m), 2.8-3.4 (4H, m), 3.95-4.05 (1H, m), 4.05-4.15 (1H, m), 4.31 (1H, dd, J=12.2 Hz, 1.7 Hz), 4.35-4.55 (2H, m), 5.2-5.35 (1H, m), 5.35-5.45 (1H, m), 5.45-5.55 (1H, m), 6.03 (1H, d, J=8.1 Hz), 6.7 (1H, d, J=4.9 Hz), 6.9-7.0 (2H, m), 7.15-7.25 (2H, m), 8.27 (1H, d, J=4.9 Hz)

Example 29

1-(3-Carbamoylpropyl)-3-(β-D-glucopyranosyloxy)-4-[2-(4-hydroxyphenyl)ethyl]-1H-pyrazolo[3,4-b]pyridine To a solution of 1-(3-carboxypropyl)-3-(2,3,4,6-tetra-O-pivaloyl-β-D-glucopyranosyloxy)-4-[2-(4-pivaloyloxyphenyl)-ethyl]-1H-pyrazolo[3,4-b]pyridine (95 mg) in N,N-dimethylformamide (2 mL) were added di (tert-butyl) dicarbonate (90 mg), pyridine (0.033 mL) and ammonium hydrogen carbonate (33 mg), and the mixture was stirred at room temperature for 3 hours. The reaction mixture was poured into 0.5 mol/L hydrochloric acid, and the resulting mixture was extracted with ethyl acetate. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=1/2-dichloromethane/methanol=15/1) to give 1-(3-carbamoylpropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (80 mg). This material was dissolved in methanol (2 mL). To the solution was added sodium methoxide (0.05 mL), and the mixture was stirred at 60° C. overnight. To the reaction mixture was added acetic acid (0.025 mL), and the resulting mixture was concentrated under reduced pressure. The residue was dissolved in a saturated aqueous potassium carbonate solution, and the solution was purified by solid phase extraction on ODS (washing solvent: distilled water, eluent: methanol) to give the product. The product was further purified by column chromatography on silica gel (eluent: dichloromethane/methanol =5/1–3/1) to give the title compound (23 mg).

¹H-NMR (CD₃OD) δ ppm: 2.05-2.3 (4H, m), 2.85-3.05 (2H, m), 3.15-3.25 (1H, m), 3.25-3.65 (5H, m), 3.7 (1H, dd, J=12.2 Hz, 5.7 Hz), 3.88 (1H, dd, J=12.2 Hz, 2.0 Hz), 4.3-4.45 (2H, m), 5.76 (1H, d, J=8.0 Hz), 6.65-6.75 (2H, m), 6.85 (1H, d, J=4.8 Hz), 7.0-7.1 (2H, m), 8.28 (1H, d, J=4.8 Hz)

Example 30

1-(3-Hydroxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine To a solution of 3-(2,3,4,6-tetra-O-pivaloyl-β-D-glucopyranosyloxy)-4-[2-(4-pivaloyloxyphenyl)ethyl]-1H-pyrazolo[3,4-b]pyridine (1 g) in acetone (10 mL) were added cesium carbonate (0.78 g), benzyl 3-bromopropyl ether (0.32 mL) and a catalytic amount of sodium iodide, and the mixture was stirred at room temperature for 2 days. The reaction mixture was purified by column chromatography on silica gel (eluent: n-hexane/ethyl acetate=4/1–2/1) to give 1-(3-benzyloxy-propyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (0.77 g). This material was dissolved in methanol (10 mL). To the solution was added 10% palladium-carbon powder (0.25 g), and the mixture was stirred at room temperature under a hydrogen atmosphere for 2 hours. The insoluble material was removed by filtration, and the filtrate was concentrated under reduced pressure. The residue was purified by column chromatography on silica gel (eluent: n-hexane/ethyl acetate =1/1–1/2) to give the title compound (0.54 g).

¹H-NMR (CDCl₃) δ ppm: 1.03 (9H, s), 1.14 (9H, s), 1.15 (9H, s), 1.17 (9H, s), 1.35 (9H, s), 1.9-2.1 (2H, m), 2.9-3.1 (2H, m), 3.1-3.35 (2H, m), 3.35-3.55 (2H, m), 3.95-4.1 (2H, m), 4.1-4.2 (1H, m), 4.24 (1H, dd, J=12.4 Hz, 1.7 Hz), 4.49 (2H, t, J=6.1 Hz), 5.2-5.3 (1H, m), 5.35-5.45 (1H, m), 5.45-5.55 (1H, m), 6.03 (1H, d, J=7.9 Hz), 6.68 (1H, d, J=4.8 Hz), 6.95-7.0 (2H, m), 7.15-7.2 (2H, m), 8.26 (1H, d, J=4.8 Hz)

Example 31

3-(β-D-Glucopyranosyloxy)-1-(3-hydroxypropyl)-4-[2-(4-hydroxyphenyl)ethyl]-1H-pyrazolo[3,4-b]pyridine To a solution of 1-(3-hydroxypropyl)-3-(2,3,4,6-tetra-pivaloyl-β-D-glucopyranosyloxy)-4-[2-(4-pivaloyloxy-phenyl)ethyl]-1H-pyrazolo [3, 4-b]pyridine (40 mg) in methanol (2 mL) was added sodium methoxide (28% methanol solution, 0.04 mL), and the mixture was stirred at 60° C. overnight. The reaction mixture was concentrated under reduced pressure, and the residue was purified by solid phase extraction on ODS (washing solvent: distilled water, eluent: methanol) to give the title compound (18 mg).

¹H-NMR (CD₃OD) δ ppm: 2.0-2.1 (2H, m), 2.85-3.05 (2H, m), 3.15-3.25 (1H, m), 3.25-3.4 (1H, m), 3.4-3.65 (6H, m), 3.71 (1H, dd, J=12.0 Hz, 5.0 Hz), 3.88 (1H, dd, J=12.0 Hz, 2.0 Hz), 4.43 (2H, t, J=6.8 Hz), 5.74 (1H, d, J=7.7 Hz), 6.65-6.75 (2H, m), 6.84 (1H, d, J=4.8 Hz), 7.0-7.1 (2H, m), 8.28 (1H, d, J=4.8 Hz)

Example 32

1-(3-Aminopropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine To a solution of 1-(3-hydroxypropyl)-3-(2,3,4,6-tetra-pivaloyl-β-D-glucopyranosyloxy)-4-[2-(4-pivaloyloxy-phenyl)ethyl]-1H-pyrazolo[3,4-b]pyridine (0.49 g) and triethylamine (0.11 mL) in dichloromethane (5 mL) was added methanesulfonyl chloride (0.051 mL), and the mixture was stirred at room temperature for 30 minutes. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure to give 1-(3-methanesulfonyloxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (0.53 g). To a solution of the obtained 1-(3-methanesulfonyloxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (0.16 g) in N,N-dimethylformamide (3 mL) was added sodium azide (16 mg), and the mixture was stirred at100° C. for 1 hour. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/1) to give 1-(3-azidopropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (94 mg). This material was dissolved in tetrahydrofuran (3 mL). To the solution was added 10% palladium-carbon powder (30 mg), and the mixture was stirred at room temperature under a hydrogen atmosphere for 3 hours. The insoluble material was removed by filtration, and the filtrate was concentrated under reduced pressure to give the title compound (90 mg).

¹H-NMR (CDCl₃) δ ppm: 1.03 (9H, s), 1.13 (9H, s), 1.15 (9H, s), 1.17 (9H, s), 1.35 (9H, s), 1.9-2.05 (2H, m), 2.55-2.7 (2H, m), 2.85-3.1 (2H, m), 3.1-3.3 (2H, m), 3.95-4.05 (1H, m), 4.13 (1H, dd, J=12.5 Hz, 4.7 Hz), 4.22 (1H, dd, J=12.5 Hz, 1.8 Hz), 4.3-4.55 (2H, m), 5.2-5.3 (1H, m), 5.35-5.45 (1H, m), 5.45-5.55 (1H, m), 6.06 (1H, d, J=8.2 Hz), 6.65 (1H, d, J=4.8 Hz), 6.95-7.0 (2H, m), 7.15-7.25 (2H, m), 8.27 (1H, d, J=4.8 Hz)

Example 33

1-(3-Aminopropyl)-3-(β-D-glucopyranosyloxy)-4-[2-(4-hydroxyphenyl)ethyl]-1H-pyrazolo[3,4-b]pyridine The title compound was prepared in a similar manner to that described in Example 31 using 1-(3-aminopropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine instead of 1-(3-hydroxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine.

¹H-NMR (CD₃OD) δ ppm: 1.95-2.1 (2H, m), 2.55-2.7 (2H, m), 2.85-3.05 (2H, m), 3.1-3.65 (6H, m), 3.7 (1H, dd, J=12.0 Hz, 5.7 Hz), 3.89 (1H, dd, J=12.0 Hz, 2.1 Hz), 4.35-4.5 (2H, m), 5.73 (1H, d, J=7.9 Hz), 6.65-6.75 (2H, m), 6.86 (1H, d, J=4.9 Hz), 7.0-7.1 (2H, m), 8.29 (1H, d, J=4.9 Hz)

Example 34

1-[3-(2-Aminoacetylamino)propyl]-3-(β-D-glucopyranosyloxy)-4-[2-(4-hydroxyphenyl)ethyl]-1H-pyrazolo[3,4-b]pyridine To a solution of 1-(3-aminopropyl)-3-(2,3,4,6-tetra-O-pivaloyl-β-D-glucopyranosyloxy)-4-[2-(4-pivaloyloxy-phenyl)ethyl]-1H-pyrazolo[3,4-b]pyridine (60 mg) in N,N-dimethylformamide (3 mL) were added 2-benzyloxycarbonylaminoacetic acid (17 mg), 1-hydroxybenzotriazole (11 mg), 1-ethyl-3-(3-dimethylaminopropyl)carbodiimide hydrochloride (26 mg) and triethylamine (0.037 mL), and the mixture was stirred at room temperature overnight. The reaction mixture was poured into 0.5 mol/L hydrochloric acid, and the resulting mixture was extracted with ethyl acetate. The extract was washed with water, a saturated aqueous sodium hydrogen carbonate solution and brine successively, and dried over anhydrous sodium sulfate. The solvent was removed under reduced pressure, and the residue was purified by column chromatography on silica gel (eluent: n-hexane/ethyl acetate=1/2–1/5) to give 1-{3-[2-(benzyloxycarbonylamino)acetylamino]propyl}-3-(2,3,4,6-tetra-O-pivaloyl-β-D-glucopyranosyloxy)-4-[2-(4-pivaloyloxyphenyl)ethyl]-1H-pyrazolo[3,4-b]pyridine (48 mg). This material was dissolved in methanol (2 mL). To the solution was added 10% palladium-carbon powder (20 mg), and the mixture was stirred at room temperature under a hydrogen atmosphere for 3 hours. The insoluble material was removed by filtration, and the solvent of the filtrate was removed under reduced pressure to give 1-[3-(2-aminoacetylamino)propyl]-3-(2,3,4,6-tetra-O-pivaloyl-β-D-glucopyranosyloxy)-4-[2-(4-pivaloyloxyphenyl)-ethyl]-1H-pyrazolo[3,4-b]pyridine (39 mg). This material was dissolved in methanol (2 mL). To the solution was added sodium methoxide (28% methanol solution, 0.02 mL), and the mixture was stirred at 50° C. overnight. The reaction mixture was concentrated under reduced pressure, and the residue was purified by solid phase extraction on ODS (washing solvent: distilled water, eluent: methanol) and preparative reverse phase column chromatography (Shiseido CAPCELL PAK UG120 ODS, 5 μm, 120 Å, 20×50 mm, flow rate 30 mL/minute linear gradient, water/methanol =90/10–10/90) successively to give the title compound (6 mg)

$^1$H-NMR (CD$_3$OD) δ ppm: 2.0-2.15 (2H, m), 2.85-3.05 (2H, m), 3.1-3.4 (6H, m), 3.4-3.65 (4H, m), 3.7 (1H, dd, J=12.3 Hz, 5.7 Hz), 3.88 (1H, dd, J=12.3 Hz, 2.2 Hz), 4.3-4.45 (2H, m), 5.75 (1H, d, J=7.7 Hz), 6.65-6.75 (2H, m), 6.85 (1H, d, J=4.7 Hz), 7.0-7.1 (2H, m), 8.29 (1H, d, J=4.7 Hz)

Example 35

3-(β-D-Glucopyranosyloxy)-4-[2-(4-hydroxyphenyl)ethyl]-1-(2-dimethylaminoethyl)-1H-pyrazolo[3,4-b]pyridine To a solution of 3-(2,3,4,6-tetra-O-pivaloyl-β-D-glucopyranosyloxy)-4-[2-(4-pivaloyloxyphenyl)ethyl]-1H-pyrazolo-[3,4-b]pyridine (75 mg) in tetrahydrofuran (0.5 mL) were added 2-dimethylaminoethanol (9 mg), triphenylphosphine (26 mg) and diethyl azodicarboxylate (40% toluene solution, 0.059 mL), and the mixture was stirred at room temperature for 3 hours. The reaction mixture was purified by column chromatography on silica gel (eluent: dichloromethane/methanol=15/1) to give 1-(2-dimethylaminoethyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine (79 mg). This material was dissolved in methanol (2 mL). To the solution was added sodium methoxide (28% methanol solution, 0.04 mL), and the mixture was stirred at 50° C. for 3 hours. The reaction mixture was purified by column chromatography on silica gel (eluent: dichloromethane/methanol =5/1–1/1) to give the title compound (16 mg).

$^1$H-NMR (CD$_3$OD) δ ppm: 2.3 (6H, s), 2.8-3.05 (4H, m), 3.15-3.25 (1H, m), 3.25-3.4 (1H, m), 3.4-3.65 (4H, m), 3.69 (1H, dd, J=12.0 Hz, 5.5 Hz), 3.86 (1H, dd, J=12.0 Hz, 2.1 Hz), 4.47 (2H, t, J=6.7 Hz), 5.75 (1H, d, J=7.8 Hz), 6.65-6.75 (2H, m), 6.84 (1H, d, J=4.6 Hz), 7.0-7.1 (2H, m), 8.29 (1H, d, J=4.6 Hz)

Example 36

3-(β-D-Glucopyranosyloxy)-4-[2-(4-hydroxyphenyl)ethyl]-1-[2-(morpholin-4-yl)ethyl]-1H-pyrazolo[3,4-b]pyridine The title compound was prepared in a similar manner to that described in Example 35 using 4-(2-hydroxyethyl)morpholine instead of 2-dimethylaminoethanol.

$^1$H-NMR (CD$_3$OD) δ ppm: 2.45-2.6 (4H, m), 2.8-3.05 (4H, m), 3.1-3.25 (1H, m), 3.25-3.4 (1H, m), 3.4-3.65 (8H, m), 3.7 (1H, dd, J=12.2 Hz, 5.2 Hz), 3.87 (1H, dd, J=12.2 Hz, 1.9 Hz), 4.48 (2H, t, J=6.6 Hz), 5.74 (1H, d, J=8.0 Hz), 6.65-6.75 (2H, m), 6.83 (1H, d, J=4.7 Hz), 7.0-7.1 (2H, m), 8.27 (1H, d, J=4.7 Hz)

Example 37

4-[2-(4-Methoxyphenyl)ethyl]-3-(2,3,4,6-tetra-O-pivaloyl-β-D-glucopyranosyloxy)-1H-pyrazolo[3,4-b]pyridine 4-[2-(4-Methoxyphenyl)ethyl]-1H-pyrazolo[3,4-b]-pyridin-3-ol was prepared in a similar manner to that described in Reference Example 12 using iodomethane instead of benzyl bromide, then the title compound was prepared in a similar manner to that described in Example 7 using this material instead of 4-(2-phenylethyl)-1H-pyrazolo[3,4-b]pyridin-3-ol.

$^1$H-NMR (CDCl$_3$) δ ppm: 1.04 (9H, s), 1.14 (9H, s), 1.15 (9H, s), 1.17 (9H, s), 2.85-3.05 (2H, m), 3.1-3.3 (2H, m), 3.79 (3H, s), 3.95-4.05 (1H, m), 4.05-4.25 (2H, m), 5.2-5.3 (1H, m), 5.4-5.55 (2H, m), 6.04 (1H, d, J=7.8 Hz), 6.7 (1H, d, J=4.9 Hz), 6.75-6.85 (2H, m), 7.05-7.15 (2H, m), 8.3 (1H, d, J=4.9 Hz), 9.76 (1H, s)

Examples 38 to 41

The compounds described in Table 1 were prepared in a similar manner to that described in Example 24 using the corresponding starting materials.

TABLE 1

| Example number | Chemical structure | $^1$H-NMR (CD$_3$OD) δ ppm |
|---|---|---|
| Example 38 | 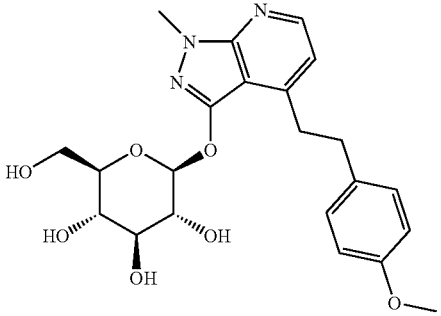 | 2.9-3.05(2H, m), 3.1-3.65(6H, m), 3.71 (1H, dd, J=12.2Hz, 5.2Hz), 3.75(3H, s), 3.88(1H, dd, J=12.2Hz, 2.2Hz), 3.93 (3H, s), 5.72(1H, d, J=7.8Hz), 6.75-6.9 (3H, m), 7.1-7.2(2H, m), 8.29(1H, d, J=4.8Hz) |

TABLE 1-continued

| Example number | Chemical structure | $^1$H-NMR (CD$_3$OD) δ ppm |
|---|---|---|
| Example 39 | 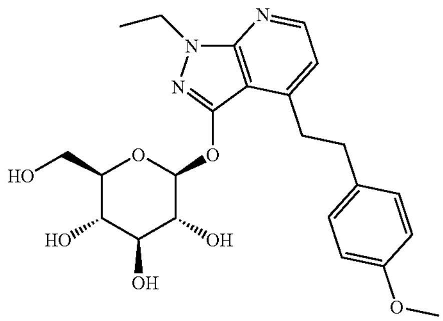 | 1.41(3H, t, J=7.0Hz), 2.9-3.05(2H, m), 3.1-3.65(6H, m), 3.71(1H, dd, J=12.4Hz, 5.4Hz), 3.75(3H, s), 3.87(1H, dd, J=12.4Hz, 2.1Hz), 4.3-4.45(2H, m), 5.75 (1H, d, J=8.1Hz), 6.75-6.9(3H,m), 7.1-7.2(2H, m), 8.28(1H, d, J=4.6Hz) |
| Example 40 | 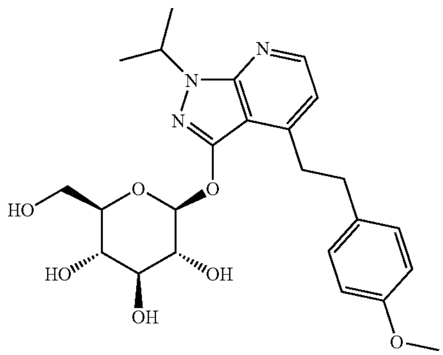 | 1.48(6H, d, J=6.5Hz), 2.85-3.05(2H, m), 3.1-3.65(6H, m), 3.7(1H, dd, J=12.1Hz, 5.2Hz), 3.75(3H, s), 3.86(1H, dd, J=12.1Hz, 2.0Hz), 5.05-5.15(1H, m), 5.79(1H, d, J=8.1Hz), 6.75-6.85(3H, m), 7.1-7.2(2H, m), 8.26(1H, d, J=4.8Hz) |
| Example 41 | 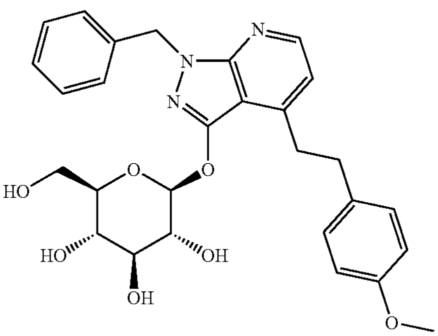 | 2.9-3.05(2H, m), 3.1-3.6(6H, m), 3.7 (1H, dd, J=12.1Hz, 4.7Hz), 3.75(3H, s), 3.83(1H, dd, J=12.1Hz, 2.2Hz), 5.48 (1H, d, J=15.8Hz), 5.57(1H, d, J=15.8Hz), 5.74(1H, d, J=7.9Hz), 6.75-6.85(2H, m), 6.88(1H, d, J=4.8Hz), 7.1-7.3(7H, m), 8.3(1H, d, J=4.8Hz) |

Example 42

3-(β-D-Glucopyranosyloxy)-1-(2-hydroxyethyl)-4-[2-(4-hydroxyphenyl)ethyl]-1H-pyrazolo[3,4-b]pyridine 1-(2-Hydroxyethyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine was prepared in a similar manner to that described in Example 30 using benzyl 2-bromoethyl ether instead of benzyl 3-bromopropyl ether, then the title compound was prepared in a similar manner to that described in Example 31 using this material instead of 1-(3-hydroxypropyl)-3-(2,3,4,6-tetra-O-pivaloyl-β-D-glucopyranosyloxy)-4-[2-(4-pivaloyloxyphenyl)ethyl]-1H-pyrazolo[3,4-b]pyridine.

$^1$H-NMR (CD$_3$OD) δ ppm: 2.85-3.05 (2H, m), 3.1-3.25 (1H, m), 3.25-3.65 (5H, m), 3.69 (1H, dd, J=12.2 Hz, 5.5 Hz), 3.88 (1H, dd, J=12.2 Hz, 1.9 Hz), 3.95 (2H, t, J=5.7 Hz), 4.35-4.5 (2H, m), 5.76 (1H, d, J=7.8 Hz), 6.65-6.75 (2H, m), 6.85 (1H, d, J=4.9 Hz), 7.0-7.1 (2H, m), 8.28 (1H, d, J=4.9 Hz)

Example 43

1-[N-(Ethoxycarbonylmethyl)carbamoylmethyl]-3-(β-D-glucopyranosyloxy)-4-[2-(4-hydroxyphenyl)ethyl]-1H-pyrazolo[3,4-b]pyridine The title compound was prepared in a similar manner to that described in Example 14 using ethyl 2-aminoacetate hydrochloride instead of dimethylamine hydrochloride.

$^1$H-NMR (CD$_3$OD) δ ppm: 1.24 (3H, t, J=7.2 Hz), 2.85-3.05 (2H, m), 3.1-3.65 (6H, m), 3.69 (1H, dd, J=12.1 Hz, 5.4 Hz), 3.87 (1H, dd, J=12.1 Hz, 2.2 Hz), 3.94 (2H, s), 4.16 (2H, q, J=7.2 Hz), 5.05 (1H, d, J=17.0 Hz), 5.09 (1H, d, J=17.0 Hz), 5.77 (1H, d, J=7.9 Hz), 6.65-6.75 (2H, m), 6.91 (1H, d, J=4.7 Hz), 7.05-7.15 (2H, m), 8.31 (1H, d, J=4.7 Hz)

Reference Example 16

4-Bromo-3-(2,3,4,6-tetra-O-pivaloyl-β-D-glucopyranosyloxy)-1-(2-pivaloyloxyethyl)-1H-indazole To a solution of 2-bromoethanol (0.36 mL) and pyridine (0.61 mL) in tetrahydrofuran (5 mL) was added pivaloyl chloride (0.62 mL) under ice-cooling, and the mixture was stirred at room temperature overnight. The reaction mixture was poured into a saturated aqueous ammonium chloride solution, and the resulting mixture was extracted with diethyl ether. The extract was washed with water, a saturated aqueous sodium hydrogen carbonate solution and brine, and dried over anhydrous sodium sulfate. The solvent was removed under reduced pressure to give (2-bromoethyl) pivalate (1.04 g). A mixture of 4-bromo-3-(2,3,4,6-tetra-O-pivaloyl-β-D-glucopyranosyloxy)-1H-indazole (0.93 g), (2-bromoethyl)pivalate (0.82 g), cesium carbonate (1.27 g) and sodium iodide (0.2 g) in N,N-dimethylformamide (10 mL) was stirred at 65° C. for 6 hours. The reaction mixture was poured into water, and the resulting mixture was extracted with diethyl ether. The extract was washed with water and brine, and dried over anhydrous sodium sulfate. The solvent was removed under reduced pressure, and the residue was purified by column chromatography on silica gel (eluent: n-hexane/ethyl acetate=4/1–3/1) to give the title compound (0.73 g).

$^1$H-NMR (CDCl$_3$) δ ppm: 1.02 (9H, s), 1.07 (9H, s), 1.14 (9H, s), 1.17 (9H, s), 1.2 (9H, s), 3.95-4.05 (1H, m), 4.16 (1H, dd, J=12.3 Hz, 5.0 Hz), 4.26 (1H, dd, J=12.3 Hz, 1.6 Hz), 4.3-4.5 (4H, m), 5.25-5.35 (1H, m), 5.4-5.5 (2H, m), 5.88 (1H, d, J=7.5 Hz), 7.1-7.25 (3H, m)

Reference Example 17

4-Bromo-1-isopropyl-3-(2,3,4,6-tetra-O-pivaloyl-β-D-glucopyranosyloxy)-1H-indazole The title compound was prepared in a similar manner to that described in Reference Example 16 using isopropyl iodide instead of (2-bromoethyl) pivalate.

$^1$H-NMR (CDCl$_3$) δ ppm: 1.06 (9H, s), 1.14 (9H, s), 1.17 (9H, s), 1.19 (9H, s), 1.4-1.55 (6H, m), 3.95-4.05 (1H, m), 4.16 (1H, dd, J=12.5 Hz, 5.0 Hz), 4.24 (1H, dd, J=12.5 Hz, 1.7 Hz), 4.55-4.7 (1H, m), 5.25-5.35 (1H, m), 5.4-5.5 (2H, m), 5.9-6.0 (1H, m), 7.05-7.25 (3H, m)

Reference Example 18

1-(2-Benzyloxyethyl)-4-bromo-3-(2,3,4,6-tetra-O-pivaloyl-β-D-glucopyranosyloxy)-1H-indazole The title compound was prepared in a similar manner to that described in Reference Example 16 using benzyl 2-bromoethyl ether instead of (2-bromoethyl) pivalate.

$^1$H-NMR (CDCl$_3$) δ ppm: 1.07 (9H, s), 1.14 (9H, s), 1.17 (9H, s), 1.19 (9H, s), 3.75-3.9 (2H, m), 3.9-4.0 (1H, m), 4.13 (1H, dd, J=12.6 Hz, 5.0 Hz), 4.23 (1H, dd, J=12.6 Hz, 1.7 Hz), 4.25-4.5 (4H, m), 5.25-5.35 (1H, m), 5.4-5.5 (2H, m), 5.85 (1H, d, J=7.6 Hz), 7.05-7.35 (8H, m)

Reference Example 19

4-Ethynyl-1-isopropyl-3-(2,3,4,6-tetra-O-pivaloyl-β-D-glucopyranosyloxy)-1H-indazole The title compound was prepared in a similar manner to that described in Reference Example 4 using 4-bromo-1-isopropyl-3-(2,3,4,6-tetra-O-pivaloyl-β-D-glucopyranosyloxy)-1H-indazole instead of 4-bromo-3-(2,3,4,6-tetra-O-pivaloyl-β-D-glucopyranosyloxy)-1H-indazole.

$^1$H-NMR (CDCl$_3$) δ ppm: 1.06 (9H, s), 1.14 (9H, s), 1.17 (9H, s), 1.2 (9H, s), 1.45-1.55 (6H, m), 3.33 (1H, s), 3.95-4.05 (1H, m), 4.17 (1H, dd, J=12.5 Hz, 5.1 Hz), 4.24 (1H, dd, J=12.5 Hz, 1.8 Hz), 4.6-4.7 (1H, m), 5.25-5.35 (1H, m), 5.4-5.5 (2H, m), 5.9-5.95 (1H, m), 7.15 (1H, dd, J=6.0 Hz, 2.2 Hz), 7.2-7.3 (2H, m)

Examples 44 to 53

The compounds described in Table 2 and Table 3 were prepared in a similar manner to that described in Example 3 and Example 4 using the corresponding starting materials. The compounds described in Example 51 and Example 52 were prepared without hydrogenation described in Example 4.

TABLE 2

| Example number | Chemical structure | $^1$H-NMR (CD$_3$OD) δ ppm |
|---|---|---|
| Example 44 | 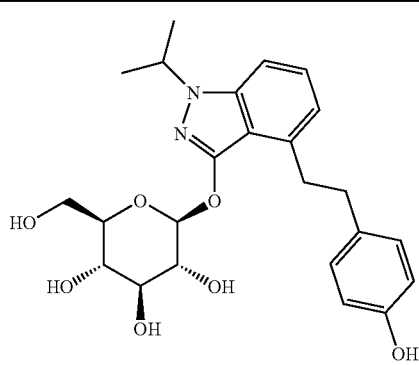 | 1.47(6H, d, J=6.5Hz), 2.75-3.0(2H, m), 3.05-3.2(1H, m), 3.25-3.65(5H, m), 3.69 (1H, dd, J=11.9Hz, 5.2Hz), 3.86(1H, dd, J=11.9Hz, 1.9Hz), 4.7-4.8(1H, m), 5.76 (1H, d, J=7.8Hz), 6.65-6.8(3H, m), 7.05-7.15(2H, m), 7.15-7.25(2H, m) |

TABLE 2-continued

| Example number | Chemical structure | $^1$H-NMR (CD$_3$OD) δ ppm |
|---|---|---|
| Example 45 | 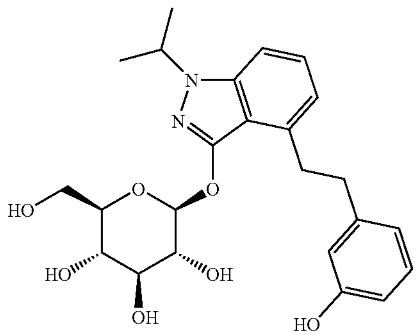 | 1.47(6H, d, J=6.6Hz), 2.8-3.0(2H, m), 3.1-3.25(1H, m), 3.25-3.4(1H, m), 3.4-3.65(4H, m), 3.71(1H, dd, J=12.1Hz, 5.0Hz), 3.87(1H, dd, J=12.1Hz, 2.0Hz), 4.7-4.8(1H, m), 5.76(1H, d, J=8.0Hz), 6.55-6.65(1H, m), 6.7-6.8(3H, m), 7.05-7.1(1H, m), 7.15-7.25(2H, m) |
| Example 46 | 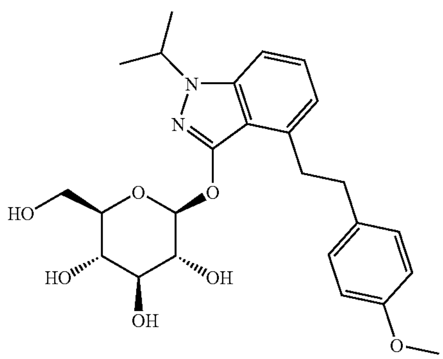 | 1.47(6H, d, J=6.7Hz), 2.8-3.05(2H, m), 3.05-3.2(1H, m), 3.25-3.4(1H, m), 3.4-3.65(4H, m), 3.69(1H, dd, J=12.0Hz, 5.3Hz), 3.76(3H, s), 3.86(1H, dd, J=12.0Hz, 1.9Hz), 4.7-4.8(1H, m), 5.76(1H, d, J=8.0Hz), 6.7-6.85(3H, m), 7.15-7.25(4H, m) |
| Example 47 | 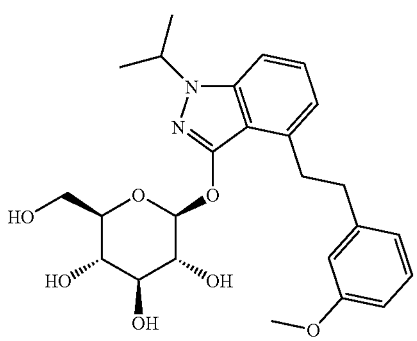 | 1.48(6H, d, J=6.7Hz), 2.85-3.05(2H, m), 3.1-3.25(1H, m), 3.25-3.65(5H, m), 3.7(1H, dd, J=12.1Hz, 5.4Hz), 3.76(3H, s), 3.86(1H, dd, J=12.1Hz, 2.1Hz), 4.7-4.8(1H, m), 5.77(1H, d, J=7.9Hz), 6.65-6.9(4H, m), 7.1-7.25(3H, m) |
| Example 48 | 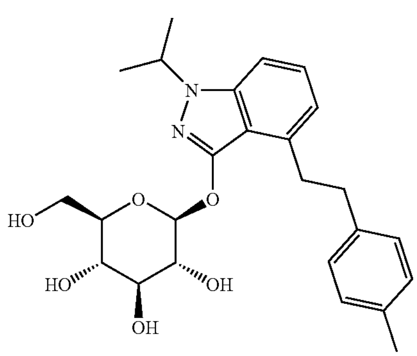 | 1.48(6H, d, J=6.6Hz), 2.29(3H, s), 2.85-3.1(2H, m), 3.1-3.25(1H, m), 3.25-3.65(5H, m), 3.69(1H, dd, J=12.0Hz, 5.5Hz), 3.86(1H, dd, J=12.0Hz, 2.2Hz), 4.7-4.8(1H, m), 5.76(1H, d, J=7.5Hz), 6.7-6.8(1H, m), 7.0-7.35(6H, m) |

TABLE 3

| Example number | Chemical structure | $^1$H-NMR (CD$_3$OD) δ ppm |
|---|---|---|
| Example 49 | 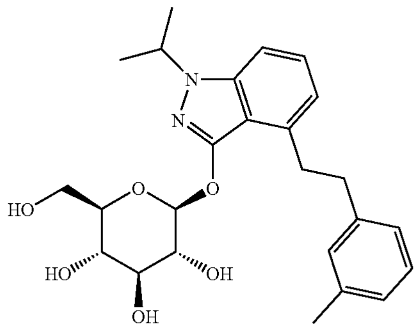 | 1.48(6H, d, J=6.7Hz), 2.31(3H, s), 2.85-3.1(2H, m), 3.1-3.25(1H, m), 3.25-3.65(5H, m), 3.7(1H, dd, J=12.2Hz, 5.3Hz), 3.86(1H, dd, J=12.2Hz, 1.8Hz), 4.7-4.8(1H, m), 5.78(1H, d, J=7.9Hz), 6.7-6.8(1H, m), 6.9-7.0(1H, m), 7.05-7.35(5H, m) |
| Example 50 | 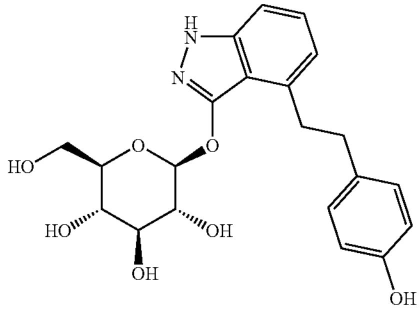 | 2.8-3.0(2H, m), 3.05-3.2(1H, m), 3.25-3.65(5H, m), 3.71(1H, dd, J=12.2Hz, 5.5Hz), 3.88(1H, dd, J=12.2Hz, 2.0Hz), 5.64(1H, d, J=7.9Hz), 6.65-6.8(3H, m), 7.05-7.1(2H, m), 7.16 (1H, d, J=8.4Hz), 7.21(1H, dd, J=8.4Hz, 6.8Hz) |
| Example 51 | 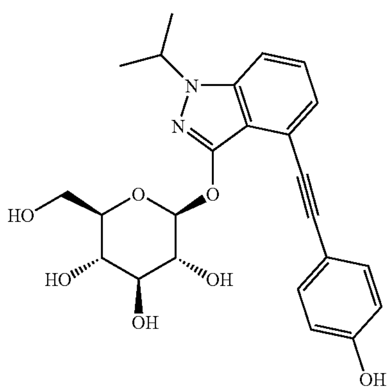 | 1.45-1.55(6H, m), 3.4-3.6(3H, m), 3.6-3.65(1H, m), 3.65-3.75(1H, m), 3.83 (1H, dd, J=11.9Hz, 1.4Hz), 4.75-4.9(1H, m), 5.81(1H, d, J=7.9Hz), 6.75-6.85(2H, m), 7.1-7.15(1H, m), 7.25-7.35(1H, m), 7.35-7.45(1H, m), 7.45-7.5(2H, m) |
| Example 52 | 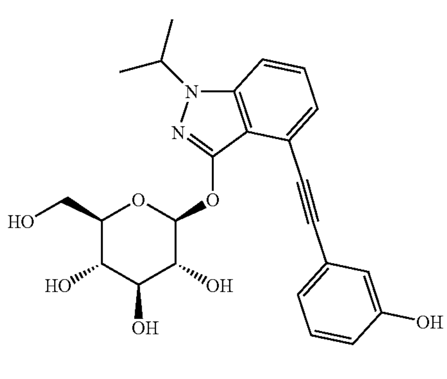 | 1.45-1.55(6H, m), 3.4-3.6(3H, m), 3.6-3.7(1H, m), 3.72(1H, dd, J=12.1Hz, 4.9Hz), 3.84(1H, dd, J=12.1Hz, 1.9Hz), 4.75-4.9(1H, m), 5.81(1H, d, J=7.9Hz), 6.75-6.85(1H, m), 7.0-7.05(1H, m), 7.05-7.15(1H, m), 7.15-7.25(2H, m), 7.25-7.35(1H, m), 7.4-7.5(1H, m) |

TABLE 3-continued

| Example number | Chemical structure | $^1$H-NMR (CD$_3$OD) δ ppm |
|---|---|---|
| Example 53 | 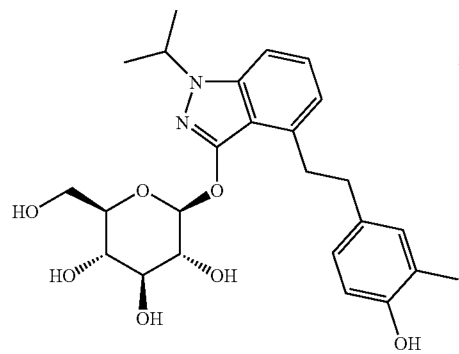 | 1.45-1.5(6H, m), 2.16(3H, s), 2.75-2.95 (2H, m), 3.05-3.15(1H, m), 3.25-3.4(1H, m), 3.4-3.65(4H, m), 3.7(1H, dd, J=12.1Hz, 5.3Hz), 3.86(1H, dd, J=12.1Hz, 2.3Hz), 4.7-4.8(1H, m), 5.76 (1H, d, J=7.9Hz), 6.64(1H, d, J=8.2Hz), 6.75(1H, dd, J=5.6Hz, 1.8Hz), 6.91(1H, dd, J=8.2Hz, 1.8Hz), 6.99(1H, d, J=1.8Hz), 7.15-7.25(2H, m) |

Reference Example 20

1-(3-Benzyloxypropoxy)-4-vinylbenzene

A mixture of 4-hydroxybenzaldehyde (1 g), benzyl 3-bromopropyl ether (1.88 g), cesium carbonate (3.2 g) and a catalytic amount of sodium iodide in N,N-dimethylformamide (15 mL) was stirred at room temperature overnight. The reaction mixture was poured into water, and the resulting mixture was extracted with diethyl ether. The extract was washed with water and dried over anhydrous magnesium sulfate. The solvent was removed under reduced pressure to give 4-(3-benzyloxypropoxy)-benzaldehyde (2.21 g). To a suspension of methyltriphenyl-phosphoniumbromide (2.92 g) in tetrahydrofuran (30 mL) was added n-butyl lithium (2.71 mol/L n-hexane solution, 3.02 mL) under ice-cooling, and the mixture was stirred for 5 minutes. To the reaction mixture was added a solution of 4-(3-benzyloxy-propoxy) benzaldehyde (2.21 g) in tetrahydrofuran (10 mL), and the mixture was stirred at room temperature for 30 minutes. To the reaction mixture was added a saturated aqueous ammonium chloride solution, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane/ethyl acetate=5/1) to give the title compound (1.4 g).

$^1$H-NMR (CDCl$_3$) δ ppm: 2.05-2.15 (2H, m), 3.6-3.7 (2H, m), 4.05-4.15 (2H, m), 4.52 (2H, s), 5.05-5.2 (1H, m), 5.55-5.65 (1H, m), 6.6-6.75 (1H, m), 6.8-6.9 (2H, m), 7.25-7.4 (7H, m)

Reference Example 21

1-Benzyloxy-4-vinylbenzene

The title compound was prepared in a similar manner to that described in Reference Example 20 using benzyl bromide instead of benzyl 3-bromopropyl ether.

$^1$H-NMR (CDCl$_3$) δ ppm: 5.07 (2H, s), 5.1-5.15 (1H, m), 5.55-5.65 (1H, m), 6.66 (1H, dd, J=17.6 Hz, 10.5 Hz), 6.9-7.0 (2H, m), 7.3-7.45 (7H, m)

Reference Example 22

1-Benzyloxy-3-vinylbenzene

The title compound was prepared in a similar manner to that described in Reference Example 20 using 3-hydroxybenzaldehyde and benzyl bromide instead of 4-hydroxybenzaldehyde and benzyl 3-bromopropyl ether, respectively.

$^1$H-NMR (CDCl$_3$) δ ppm: 5.08 (2H, s), 5.2-5.3 (1H, m), 5.7-5.8 (1H, m), 6.68 (1H, dd, J=17.5 Hz, 11.0 Hz), 6.85-6.9 (1H, m), 7.0-7.05 (2H, m), 7.2-7.3 (1H, m), 7.3-7.5 (5H, m)

Example 54

4-[(E)-2-(4-Benzyloxyphenyl)vinyl]-3-(2,3,4,6-tetra-O-pivaloyl-β-D-glucopyranosyloxy)-1H-indazole The title compound was prepared in a similar manner to that described in Example 1 using 1-benzyloxy-4-vinylbenzene instead of styrene.

$^1$H-NMR (CDCl$_3$) δ ppm: 0.99 (9H, s), 1.17 (9H, s), 1.18 (9H, s), 1.19 (9H, s), 3.95-4.05 (1H, m), 4.16 (1H, dd, J=12.6 Hz, 4.9 Hz), 4.24 (1H, dd, J=12.6 Hz, 1.8 Hz), 5.13 (2H, s), 5.25-5.35 (1H, m), 5.45-5.6 (2H, m), 5.95 (1H, d, J=7.9 Hz), 7.0-7.5 (1H, m), 7.55-7.7 (3H, m), 8.91 (1H, s)

Example 55

1-Carbamoylmethyl-3-(β-D-glucopyranosyloxy)-4-[2-(4-hydroxyphenyl)ethyl]-1H-indazole The title compound was prepared in a similar manner to that described in Example 12 using 4-[(E)-2-(4-benzyloxyphenyl)vinyl]-3-(2,3,4,6-tetra-O-pivaloyl-β-D-glucopyranosyloxy)-1H-indazole instead of 4-[2-(4-benzyloxy-phenyl)ethyl]-3-(2,3,4,6-tetra-O-pivaloyl-β-D-glucopyranosyloxy)-1H-pyrazolo[3,4-b]pyridine.

1H-NMR (CD$_3$OD) δ ppm: 2.8-3.0 (2H, m), 3.1-3.2 (1H, m), 3.25-3.65 (5H, m), 3.69 (1H, dd, J=12.2 Hz, 5.7 Hz), 3.88 (1H, dd, J=12.2 Hz, 2.4 Hz), 4.8-4.95 (2H, m), 5.74 (1H, d, J=7.9 Hz), 6.65-6.75 (2H, m), 6.82 (1H, d, J=7.1 Hz), 7.05-7.15 (2H, m), 7.18 (1H, d, J=8.3 Hz), 7.28 (1H, dd, J=8.3 Hz, 7.1 Hz)

Example 56

1-(2-Hydroxyethyl)-4-[2-(3-hydroxyphenyl)ethyl]-3-(2,3,4,6-tetra-O-pivaloyl-β-D-glucopyranosyloxy)-1H-indazole A mixture of 1-(2-benzyloxyethyl)-4-bromo-3-(2,3,4,6-tetra-O-pivaloyl-β-D-glucopyranosyloxy)-1H-indazole (0.85 g), 1-benzyloxy-3-vinylbenzene (0.32 g), triethylamine (2 mL), palladium (II) acetate (11 mg) and tris(2-methylphenyl)-phosphine (30 mg) in acetonitrile (8 mL) was heated for reflux under an argon atmosphere overnight. The reaction mixture was cooled to room temperature and diluted with diethyl ether, and the resulting mixture was stirred for 30 minutes. The insoluble material was removed by filtration, and the filtrate was concentrated under reduced pressure. The residue was purified by column chromatography on silica gel (eluent: n-hexane/ethyl acetate=4/1–3/1) to give 1-(2-benzyloxyethyl)-4-[(E)-2-(3-benzyloxyphenyl)vinyl]-3-(2,3,4,6-tetra-O-pivaloyl-β-D-glucopyranosyloxy)-1H-indazole (0.92 g). This material was dissolved in ethyl acetate (10 mL). To the solution was added 10% palladium-carbon powder (0.3 g), and the mixture was stirred at room temperature under a hydrogen atmosphere overnight. The insoluble material was removed by filtration, and the filtrate was concentrated under reduced pressure. The residue was purified by column chromatography on silica gel (eluent: n-hexane/ethyl acetate=2/1–1/1) to give the title compound (0.68 g).

$^1$H-NMR (CDCl$_3$) δ ppm: 1.05-1.2 (36H, m), 2.65-2.85 (1H, m), 2.95-3.2 (2H, m), 3.2-3.3 (1H, m), 3.9-4.0 (1H, m), 4.0-4.2 (4H, m), 4.25-4.35 (2H, m), 5.25-5.35 (1H, m), 5.4-5.6 (2H, m), 6.04 (1H, d, J=8.6 Hz), 6.7-6.95 (4H, m), 7.1-7.25 (2H, m), 7.25-7.35 (1H, m)

Example 57

1-(2-Hydroxyethyl)-4-[2-(4-hydroxyphenyl)ethyl]-3-(2,3,4,6-tetra-O-pivaloyl-β-D-glucopyranosyloxy)-1H-indazole The title compound was prepared in a similar manner to that described in Example 56 using 1-benzyloxy-4-vinylbenzene instead of 1-benzyloxy-3-vinylbenzene.

$^1$H-NMR (CDCl$_3$) δ ppm: 1.05 (9H, s), 1.12 (9H, s), 1.15 (9H, s), 1.17 (9H, s), 2.8-3.0 (2H, m), 3.05-3.15 (1H, m), 3.2-3.3 (1H, m), 3.9-4.1 (3H, m), 4.1-4.3 (4H, m), 4.74 (1H, brs), 5.25-5.35 (1H, m), 5.35-5.55 (2H, m), 5.97 (1H, d, J=7.9 Hz), 6.65-6.8 (3H, m), 7.0-7.1 (3H, m), 7.15-7.25 (1H, m)

Example 58

4-{2-[4-(3-Hydroxypropoxy)phenyl]ethyl}-3-(2,3,4,6-tetra-O-pivaloyl-β-D-glucopyranosyloxy)-1H-indazole The title compound was prepared in a similar manner to that described in Example 56 using 4-bromo-3-(2,3,4,6-tetra-O-pivaloyl-β-D-glucopyranosyloxy)-1H-indazole and 1-(3-benzyloxypropoxy)-4-vinylbenzene instead of 1-(2-benzyl-oxyethyl)-4-bromo-3-(2,3,4,6-tetra-O-pivaloyl-β-D-glucopyranosyloxy)-1H-indazole and 1-benzyloxy-3-vinylbenzene, respectively.

$^1$H-NMR (CDCl$_3$) δ ppm: 1.04 (9H, s), 1.13 (9H, s), 1.15 (9H, s), 1.17 (9H, s), 1.89 (1H, t, J=5.5 Hz), 2.0-2.1 (2H, m), 2.8-3.0 (2H, m), 3.05-3.15 (1H, m), 3.2-3.3 (1H, m), 3.85-3.9 (2H, m), 3.9-4.0 (1H, m), 4.05-4.15 (3H, m), 4.21 (1H, dd, J=12.1 Hz, 1.8 Hz), 5.25-5.3 (1H, m), 5.4-5.5 (2H, m), 6.04 (1H, d, J=7.9 Hz), 6.7 (1H, d, J=6.9 Hz), 6.8-6.85 (2H, m), 7.05-7.15 (3H, m), 7.2 (1H, dd, J=8.4 Hz, 6.9 Hz), 8.91 (1H, s)

Example 59

3-(β-D-Glucopyranosyloxy)-1-(2-hydroxyethyl)-4-[2-(4-hydroxyphenyl)ethyl]-1H-indazole To a solution of 1-(2-hydroxyethyl)-4-[2-(4-hydroxy-phenyl)ethyl]-3-(2,3,4,6-tetra-O-pivaloyl-β-D-glucopyranosyloxy)-1H-indazole (0.31 g) in methanol (6 mL) were added water (0.6 mL) and lithium hydroxide monohydrate (0.16 g), and the mixture was stirred at room temperature for 8 hours. The reaction mixture was concentrated under reduced pressure, and the residue was dissolved in water. To the solution was added acetic acid (0.45 mL), and the resulting mixture was purified by solid phase extraction on ODS (washing solvent: distilled water, eluent: methanol) to give the title compound (0.14 g)

$^1$H-NMR (CD$_3$OD) δ ppm: 2.8-3.0 (2H, m), 3.05-3.2 (1H, m), 3.25-3.65 (5H, m), 3.69 (1H, dd, J=12.0 Hz, 5.6 Hz), 3.85-3.95 (3H, m), 4.3 (2H, t, J=5.6 Hz), 5.72 (1H, d, J=7.9 Hz), 6.65-6.75 (2H, m), 6.76 (1H, dd, J=5.4 Hz, 2.7 Hz), 7.05-7.15 (2H, m), 7.2-7.3 (2H, m)

Example 60

3-(β-D-Glucopyranosyloxy)-4-{2-[4-(3-hydroxypropoxy)-phenyl]ethyl}-1H-indazole

The title compound was prepared in a similar manner to that described in Example 59 using 4-{2-[4-(3-hydroxypropoxy)-phenyl]ethyl}-3-(2,3,4, 6-tetra-O-pivaloyl-β-D-glucopyranosyloxy)-1H-indazole instead of 1-(2-hydroxyethyl)-4-[2-(4-hydroxyphenyl) ethyl]-3-(2,3,4,6-tetra-O-pivaloyl-β-D-glucopyranosyloxy)-1H-indazole.

$^1$H-NMR (CD$_3$OD) δ ppm: 1.9-2.0 (2H, m), 2.8-3.05 (2H, m), 3.05-3.2 (1H, m), 3.25-3.65 (5H, m), 3.65-3.8 (3H, m), 3.88 (1H, dd, J=12.2 Hz, 2.1 Hz), 4.04 (2H, t, J=6.4 Hz), 5.65 (1H, d, J=7.8 Hz), 6.7-6.85 (3H, m), 7.1-7.25 (4H, m)

Example 61

4-{2-[4-(3-Hydroxypropoxy)phenyl]ethyl}-3-(2,3,4, 6-tetra-O-pivaloyl-β-D-glucopyranosyloxy)-1-(2-pivaloyloxyethyl)-1H-indazole To a mixture of 1-(2-hydroxyethyl)-4-[2-(4-hydroxy-phenyl)ethyl]-3-(2,3,4,6-tetra-O-pivaloyl-β-D-glucopyranosyloxy)-1H-indazole (2 g), cesium carbonate (1.64 g) and sodium iodide (0.38 g) in N,N-dimethylformamide (10 mL) was added benzyl 3-bromopropyl ether (0.86 g), and the mixture was stirred at room temperature overnight. The reaction mixture was poured into water, and the resulting mixture was extracted with diethyl ether. The extract was washed with water and brine, and dried over anhydrous sodium sulfate. The solvent was removed under reduced pressure, and the residue was dissolved in dichloromethane (15 mL). To the solution were added triethylamine (1.22 mL) and pivaloyl chloride (0.93 mL), and the mixture was stirred at room temperature overnight. The reaction mixture was poured into 0.5 mol/L hydrochloric acid, and the resulting mixture was extracted with diethyl ether. The extract was washed with water, a saturated aqueous sodium hydrogen carbonate solution and brine, and dried over anhydrous sodium sulfate. The solvent was removed under reduced pressure, and the residue was purified by column chromatography on silica gel (eluent: n-hexane/ethyl acetate=3/1) to give 4-{2-[4-(3-benzyloxypropoxy)phenyl]ethyl}-3-(2,3,4,6-tetra-O-pivaloyl-β-D-glucopyranosyloxy)-1-(2-pivaloyloxyethyl)-1H-indazole (2.11 g). This material was dissolved in ethyl acetate (20 mL) To the solution was added 10% palladium-carbon powder (0.5 g), and the mixture was stirred at room temperature under a hydrogen atmosphere for 2 hours. The insoluble material was removed by filtration, and the filtrate was concentrated under reduced pressure. The residue was purified by column chromatography on silica gel (eluent: n-hexane/ethyl acetate=2/1–1/1) to give the title compound (1.59 g).

$^1$H-NMR (CDCl$_3$) δ ppm: 1.02 (9H, s), 1.03 (9H, s), 1.13 (9H, s), 1.15 (9H, s), 1.17 (9H, s), 2.0-2.1 (2H, m), 2.8-2.9 (1H, m), 2.9-3.0 (1H, m), 3.0-3.15 (1H, m), 3.2-3.3 (1H, m), 3.8-3.9 (2H, m), 3.9-4.0 (1H, m), 4.05-4.2 (3H, m), 4.21 (1H, dd, J=12.4 Hz, 1.6 Hz), 4.3-4.5 (4H, m), 5.2-5.3 (1H, m), 5.35-5.55 (2H, m), 6.05 (1H, d, J=7.8 Hz), 6.64 (1H, d, J=6.9 Hz), 6.75-6.85 (2H, m), 7.0-7.1 (3H, m), 7.15-7.2 (1H, m)

Examples 62 to 64

The compounds described in Table 4 were prepared in a similar manner to that described in Example 61.

TABLE 4

| Example number | Chemical structure | $^1$H-NMR (CDCl$_3$) δ ppm |
|---|---|---|
| Example 62 | 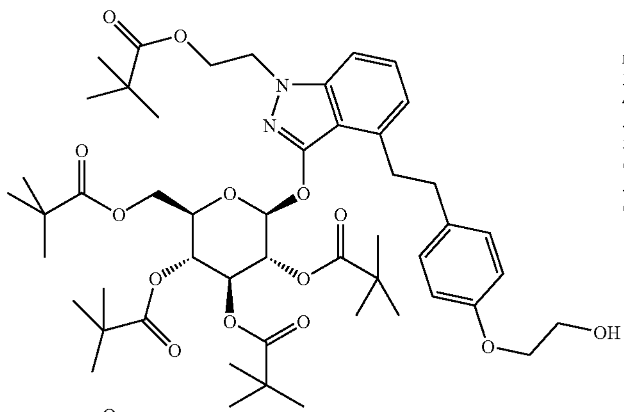 | 1.02(9H, s), 1.03(9H, s), 1.13(9H, s), 1.15(9H, s), 1.17(9H, s), 2.8-2.9(1H, m), 2.9-3.0(1H, m), 3.0-3.15(1H, m), 3.2-3.3(1H, m), 3.9-4.0(3H, m), 4.05-4.2(3H, m), 4.21(1H, dd, J=12.5Hz, 1.7Hz), 4.3-4.5(4H, m), 5.2-5.3(1H, m), 5.35-5.55(2H, m), 6.05(1H, d, J=8.3Hz), 6.64(1H, d, J=7.0Hz), 6.8-6.9(2H, m), 7.0-7.15 (3H, m), 7.15-7.2(1H, m) |
| Example 63 | 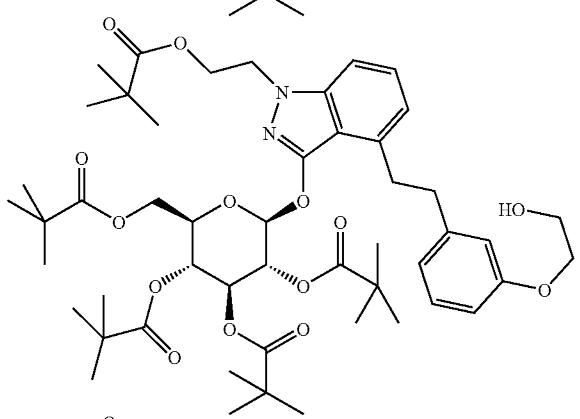 | 1.0-1.05(18H, m), 1.1(9H, s), 1.15 (9H, s), 1.17(9H, s), 2.75-2.9(1H, m), 2.95-3.15(2H, m), 3.2-3.35(1H, m), 3.9-4.0(3H, m), 4.1-4.2(3H, m), 4.21 (1H, dd, J=12.5Hz, 1.6Hz), 4.3-4.5 (4H, m), 5.25-5.35(1H, m), 5.4-5.55 (2H, m), 6.06(1H, d, J=8.0Hz), 6.7-6.85(3H, m), 6.85-6.95(1H, m), 7.05-7.15(1H, m), 7.15-7.25(2H, m) |
| Example 64 | 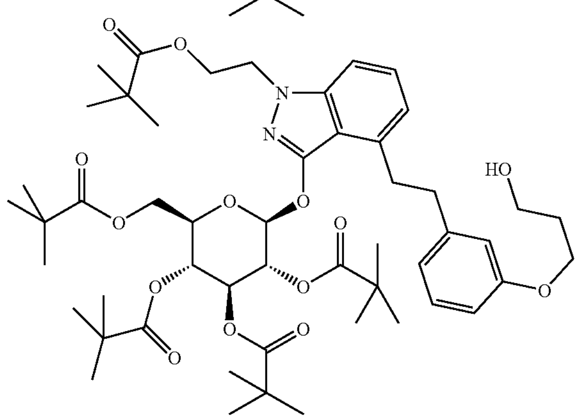 | 1.02(9H, s), 1.03(9H, s), 1.11(9H, s), 1.15(9H, s), 1.17(9H, s), 2.0-2.1(2H, m), 2.75-2.9(1H, m), 2.9-3.15(2H, m), 3.2-3.35(1H, m), 3.8-3.9(2H, m), 3.9-4.0(1H, m), 4.05-4.2(3H, m), 4.22(1H, dd, J=12.5Hz,1.7Hz), 4.3-4.5(4H, m), 5.2-5.3(1H, m), 5.35-5.55(2H, m), 6.06(1H, d, J=8.3Hz), 6.65-6.9(4H, m), 7.05-7.1 (1H, m), 7.15-7.25(2H, m) |

Example 65

3-(β-D-Glucopyranosyloxy)-1-(2-hydroxyethyl)-4-[2-(4-{3-[2-hydroxy-1-(hydroxymethyl)ethylamino]propoxy}phenyl)-ethyl]-1H-indazole To a solution of 4-{2-[4-(3-hydroxypropoxy)phenyl]-ethyl}-3-(2,3,4,6-tetra-O-pivaloyl-β-D-glucopyranosyloxy)-1-(2-pivaloyloxyethyl)-1H-indazole (1.59 g) and triethylamine (0.35 mL) in dichloromethane (10 mL) was added methanesulfonyl chloride (0.16 mL), and the mixture was stirred at room temperature for 1 hour. The reaction mixture was poured into 0.5 mol/L hydrochloric acid, and the resulting mixture was extracted with diethyl ether. The extract was washed with water and brine, and dried over anhydrous sodium sulfate. The solvent was removed under reduced pressure to give 4-{2-[4-(3-methane-sulfonyloxypropoxy)phenyl]ethyl}-3-(2,3,4,6-tetra-O-pivaloyl-β-D-glucopyranosyloxy)-1-(2-pivaloyloxyethyl)-1H-indazole (1.67 g). The obtained compound (0.52 g) was dissolved in a mixed solvent of acetonitrile (2.5 mL) and ethanol (2.5 mL). To the solution were added 2-amino-1,3-propanediol (0.12 g) and sodium iodide (77 mg), and the mixture was stirred at 75° C. for 24 hours. The reaction mixture was poured into water, and the resulting mixture was extracted with ethyl acetate. The extract was washed with brine and dried over anhydrous sodium sulfate. The solvent was removed under reduced pressure, and the residue was purified by column chromatography on silica gel (eluent: dichloromethane/methanol=20/1–10/1–8/1) to give 4-[2-(4-{3-[2-hydroxy-1-(hydroxymethyl)ethylamino]propoxy}-phenyl)ethyl]-3-(2,3,4,6-tetra-O-pivaloyl-β-D-glucopyranosyloxy)-1-(2-pivaloyloxyethyl)-1H-indazole (0.36 g). This material was dissolved in methanol (6 mL). To the solution was added lithium hydroxide monohydrate (75 mg), and the mixture was stirred at room temperature overnight. The reaction mixture was concentrated under reduced pressure, and the residue was purified by solid phase extraction on ODS (washing solvent: distilled water, eluent: methanol) to give the title compound (0.21 g).

$^1$H-NMR (CD$_3$OD) δ ppm: 1.9-2.05 (2H, m), 2.7-3.05 (5H, m), 3.05-3.2 (1H, m), 3.25-3.75 (10H, m), 3.8-3.95 (3H, m), 4.05 (2H, t, J=6.0 Hz), 4.3 (2H, t, J=5.4 Hz), 5.72 (1H, d, J=7.8 Hz), 6.7-6.9 (3H, m), 7.1-7.3 (4H, m)

Examples 66 to 87

The compounds described in Tables 5 to 9 were prepared in a similar manner to that described in Example 65 using the corresponding starting materials. For the synthesis of Examples 84 to 86, before hydrolysis described in Example 65, hydroxy groups were converted into amino groups in a similar manner to that described in Example 32.

TABLE 5

| Example number | Chemical structure | $^1$H-NMR (CD$_3$Cl) δ ppm |
|---|---|---|
| Example 66 | 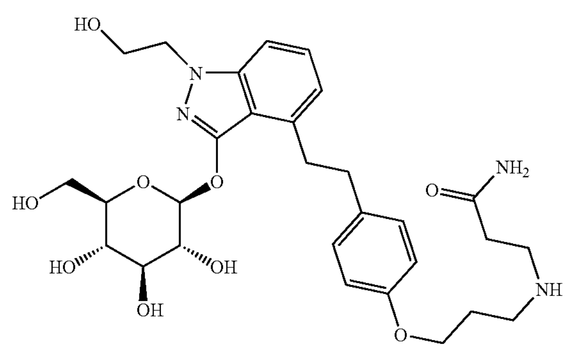 | 2.0-2.1(2H, m), 2.54(2H, t, J=6.6 Hz), 2.8-3.2(7H, m), 3.25-3.65(5H, m), 3.69(1H, dd, J=12.2Hz, 5.6Hz), 3.85-3.95(3H, m), 4.06(2H, t, J=6.0Hz), 4.3(2H, t, J=5.5Hz), 5.72 (1H, d, J=7.9Hz), 6.76(1H, dd, J=6.1Hz, 1.7Hz), 6.8-6.9(2H, m), 7.15-7.3(4H, m) |
| Example 67 | 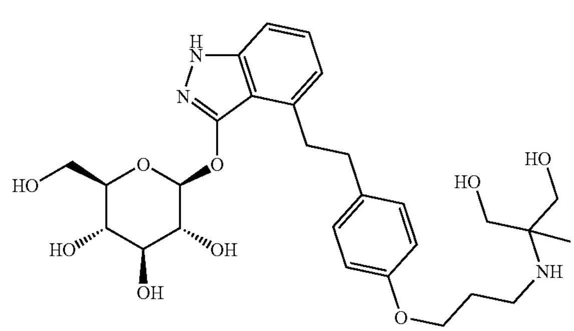 | 1.01(3H, s), 1.9-2.0(2H, m), 2.77 (2H, t, J=7.2Hz), 2.85-3.0(2H, m), 3.1-3.2(1H, m), 3.25-3.65(9H, m), 3.65-3.75(1H, m), 3.85-3.95(1H, m), 4.04(2H, t, J=6.1Hz), 5.65(1H, d, J=7.8Hz), 6.75(1H, d, J=6.3Hz), 6.8-6.9(2H, m), 7.1-7.25(4H, m) |

TABLE 5-continued

| Example number | Chemical structure | $^1$H-NMR (CD$_3$Cl) δ ppm |
|---|---|---|
| Example 68 | 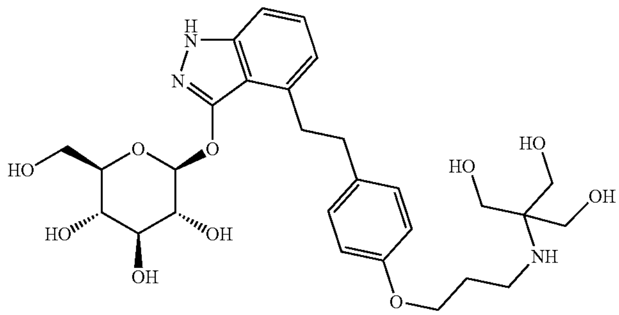 | 1.85-2.0(2H, m), 2.75-3.0(4H, m), 3.05-3.2(1H, m), 3.25-3.65(11H, m), 3.71(1H, dd, J=12.1Hz, 5.5Hz), 3.88 (1H, dd, J=12.1Hz, 2.2Hz), 4.04(2H, t, J=5.9Hz), 5.64(1H, d, J=7.6Hz), 6.7-6.85(3H, m), 7.1-7.25(4H, m) |
| Example 69 | 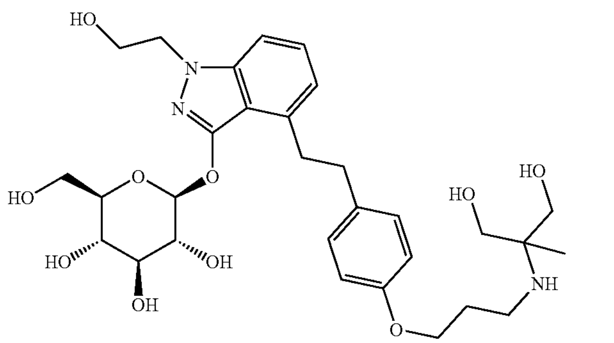 | MS(ESI, m/z): 606 [M + H]$^+$ |
| Example 70 | 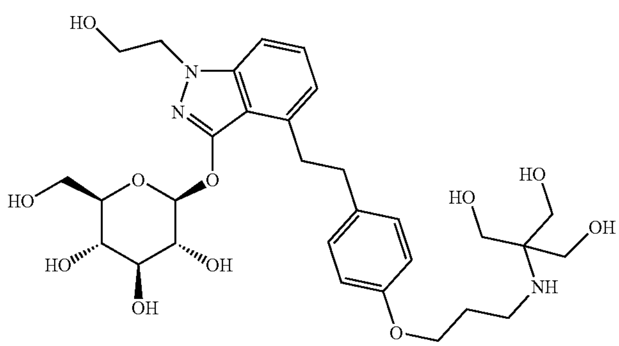 | 1.85-2.0(2H, m), 2.75-3.0(4H, m), 3.1-3.2(1H, m), 3.25-3.65(11H, m), 3.69(1H, dd, J=11.9Hz, 5.7Hz), 3.8-3.95(3H, m), 4.04(2H, t, J=6.3Hz), 4.3(2H, t, J=5.6Hz), 5.72 (1H, d, J=8.0Hz), 6.76(1H, dd, J=5.4Hz, 2.3Hz), 6.8-6.9(2H, m), 7.1-7.3(4H, m) |

TABLE 6

| Example number | Chemical structure | $^1$H-NMR (CD$_3$OD) δ ppm |
|---|---|---|
| Example 71 | 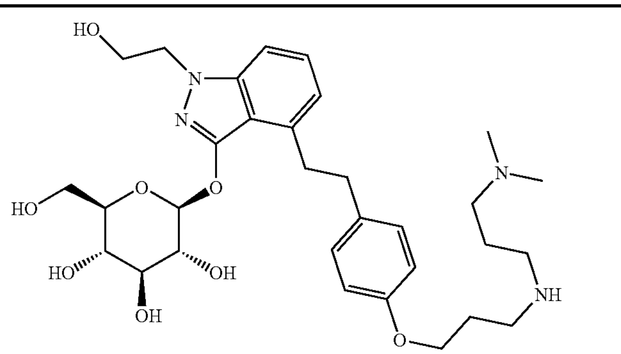 | 1.55-1.75(2H, m), 1.85-2.05(2H, m), 2.15-2.45(8H, m), 2.55-3.65(12H, m), 3.69(1H, dd, J=12.3Hz, 5.1Hz), 3.8-4.15(5H, m), 4.3(2H, t, J=5.4Hz), 5.72(1H, d, J=7.8Hz), 6.7-6.9(3H, m), 7.1-7.3(4H, m) |

TABLE 6-continued

| Example number | Chemical structure | $^1$H-NMR (CD$_3$OD) δ ppm |
|---|---|---|
| Example 72 | 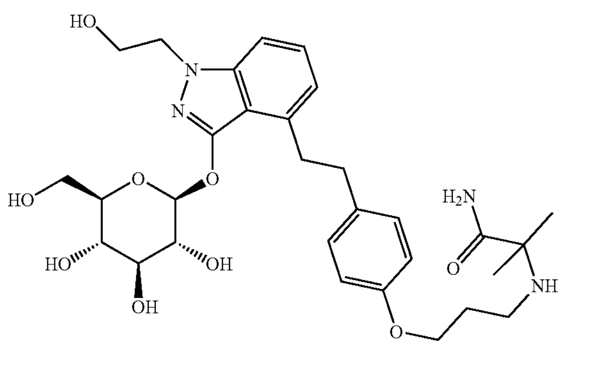 | 1.3(6H, s), 1.85-2.0(2H, m), 2.67 (2H, t, J=7.0Hz), 2.8-3.0(2H, m), 3.05-3.2(1H, m), 3.25-3.65(5H, m), 3.69(1H, dd, J=11.9Hz, 5.7Hz), 3.8-3.95(3H, m), 4.04(2H, t, J=6.0Hz), 4.29(2H, t, J=5.6Hz), 5.72(1H, d, J=7.6Hz), 6.7-6.9(3H, m), 7.1-7.3(4H, m) |
| Example 73 | 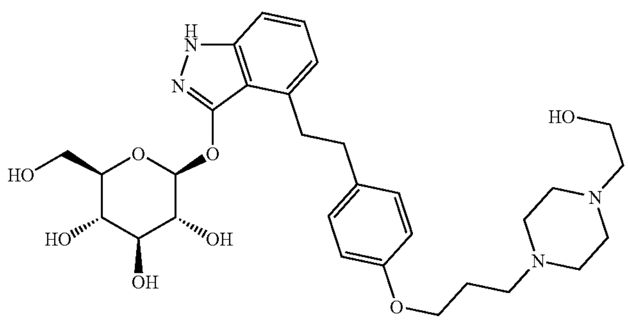 | 1.9-2.0(2H, m), 2.3-2.8(12H, m), 2.8-3.05(2H, m), 3.1-3.2(1H, m), 3.25-3.75(8H, m), 3.88(1H, dd, J=11.9Hz, 2.2Hz), 3.99(2H, t, J=6.1Hz), 5.65(1H, d, J=7.6Hz), 6.7-6.85(3H, m), 7.1-7.25(4H, m) |
| Example 74 | 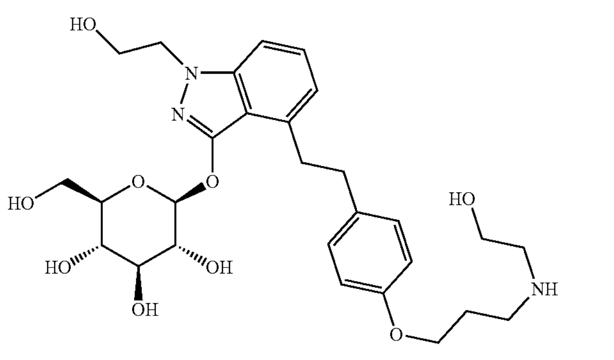 | 1.95-2.1(2H, m), 2.75-3.0(6H, m), 3.05-3.2(1H, m), 3.25-3.65(5H, m), 3.65-3.75(3H, m), 3.8-3.95(3H, m), 4.04(2H, t, J=6.0Hz), 4.3(2H, t, J=5.7Hz), 5.72(1H, d, J=7.5Hz), 6.7-6.9(3H, m), 7.1-7.3(4H, m) |
| Example 75 | 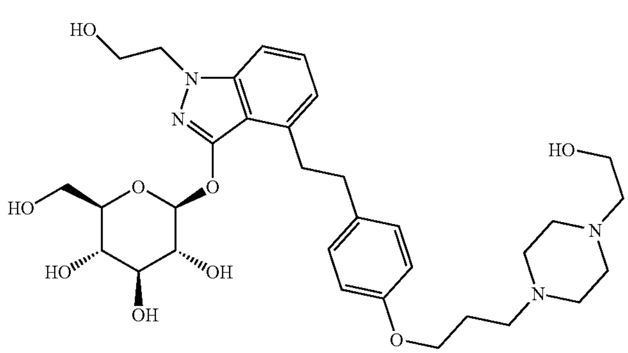 | 1.9-2.05(2H, m), 2.4-2.8(12H, m), 2.8-3.0(2H, m), 3.05-3.2(1H, m), 3.25-3.65(5H, m), 3.65-3.75(3H, m), 3.8-3.95(3H, m), 4.0(2H, t, J=6.2Hz), 4.3(2H, t, J=5.5Hz), 5.72(1H, d, J=7.9Hz), 6.7-6.85(3H, m), 7.1-7.3 (4H, m) |

TABLE 7

| Example number | Chemical structure | $^1$H-NMR (CD$_3$OD) δ ppm |
|---|---|---|
| Example 76 | 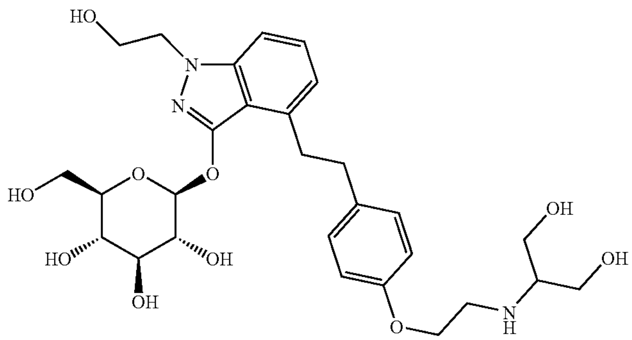 | 2.7-3.2(6H, m), 3.25-3.75(10H, m), 3.8-3.95(3H, m), 4.09(2H, t, J=5.2Hz), 4.3(2H, t, J=5.4Hz), 5.72 (1H, d, J=8.0Hz), 6.7-6.9(3H, m), 7.1-7.3(4H, m) |
| Example 77 | 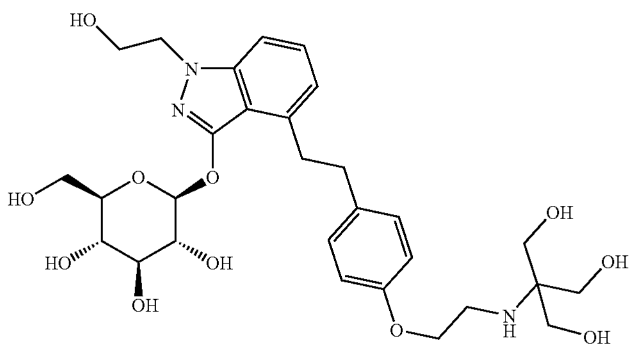 | 2.8-3.2(5H, m), 3.25-3.65(11H, m), 3.69(1H, dd, J=12.1Hz, 5.7Hz), 3.8-3.95(3H, m), 4.06(2H, t, J=5.2Hz), 4.3(2H, t, J=5.5Hz), 5.72 (1H, d, J=8.0Hz), 6.7-6.9(3H, m), 7.1-7.3(4H, m) |
| Example 78 | 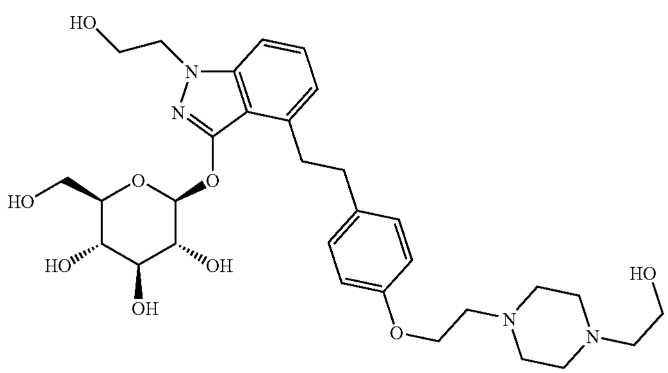 | 2.45-3.05(14H, m), 3.05-3.2(1H, m), 3.25-3.75(8H, m), 3.8-3.95(3H, m), 4.11(2H, t, J=5.5Hz), 4.3(2H, t, J=5.7Hz), 5.72(1H, d, J=7.8Hz), 6.7-6.9(3H, m), 7.1-7.3(4H, m) |
| Example 79 | 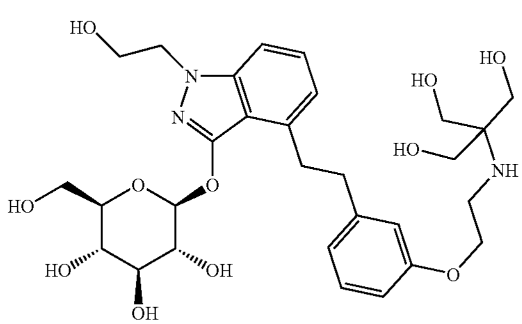 | 2.85-3.1(4H, m), 3.1-3.25(1H, m), 3.25-3.65(11H, m), 3.7(1H, dd, J=12.1Hz, 5.1Hz), 3.8-3.95(3H, m), 4.0-4.15(2H, m), 4.3(2H, t, J=5.6Hz), 5.73(1H, d, J=7.8Hz), 6.7-6.95(4H, m), 7.1-7.2(1H, m), 7.2-7.3(2H, m) |

TABLE 7-continued

| Example number | Chemical structure | $^1$H-NMR (CD$_3$OD) δ ppm |
|---|---|---|
| Example 80 | 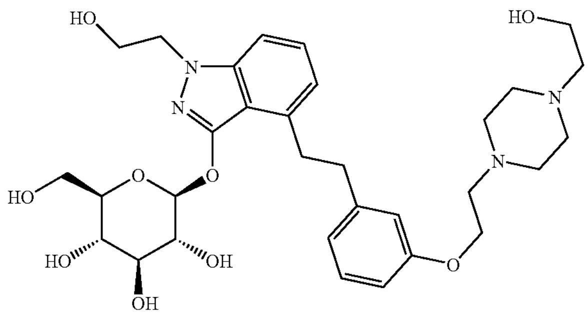 | 2.45-3.05(14H, m), 3.1-3.25(1H, m), 3.25-3.75(8H, m), 3.8-3.95(3H, m), 4.11(2H, t, J=5.3Hz), 4.3(2H, t, J=5.4Hz),(1H, d, J=7.9Hz), 6.65-6.95(4H, m), 7.1-7.3(3H, m) |
| Example 81 | 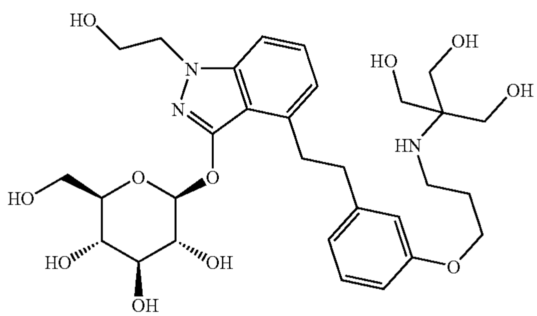 | 1.85-2.0(2H, m), 2.75-3.05(4H, m), 3.1-3.25(1H, m), 3.25-3.65(11H, m), 3.7(1H, dd, J=11.8Hz, 5.5Hz), 3.85-3.95(3H, m), 4.05(2H, t, J=6.0Hz), 4.3(2H, t, J=5.5Hz), 5.74(1H, d, J=7.9Hz), 6.65-6.9(4H, m), 7.1-7.3(3H, m) |

TABLE 8

| Example number | Chemical structure | $^1$H-NMR (CD$_3$OD) δ ppm |
|---|---|---|
| Example 82 | 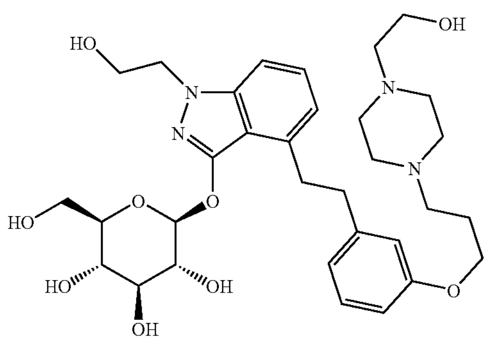 | 1.9-2.05(2H, m), 2.45-2.75(12H, m), 2.85-3.05(2H, m), 3.1-3.25(1H, m), 3.25-3.75(8H, m), 3.85-3.95(3H, m), 4.0(2H, t, J=6.2Hz), 4.3(2H, t, J=5.5Hz), 5.74(1H, d, J=8.2Hz), 6.65-6.9(4H, m), 7.1-7.3(3H, m) |
| Example 83 | 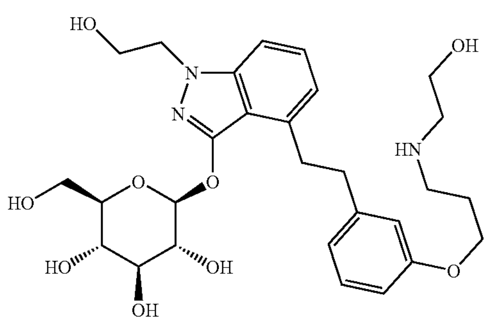 | 1.9-2.05(2H, m), 2.74(2H, t, J=5.5Hz), 2.82(2H, t, J=7.1Hz), 2.85-3.05(2H, m), 3.1-3.25(1H, m), 3.25-3.75(8H, m), 3.8-3.95(3H, m), 4.04(2H, t, J=6.0Hz), 4.3(2H, t, J=5.6Hz), 5.74(1H, d, J=7.8Hz), 6.65-6.9(4H, m), 7.1-7.3(3H, m) |

TABLE 8-continued

| Example number | Chemical structure | ¹H-NMR (CD₃OD) δ ppm |
| --- | --- | --- |
| Example 84 | 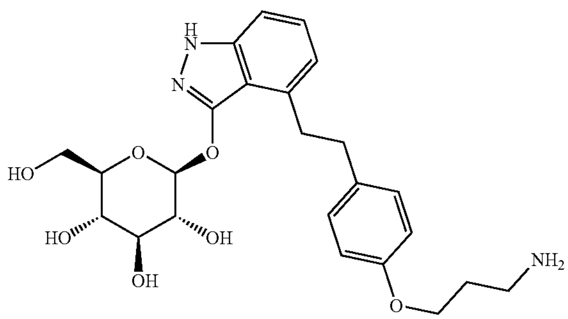 | 1.85-1.95(2H, m), 2.75-3.05(4H, m), 3.1-3.2(1H, m), 3.25-3.65(5H, m), 3.71(1H, dd, J=12.1Hz, 5.5Hz), 3.85-3.95(1H, m), 4.02(2H, t, J=6.2Hz), 5.64(1H, d, J=7.9Hz), 6.7-6.85(3H, m), 7.1-7.25(4H, m) |
| Example 85 | 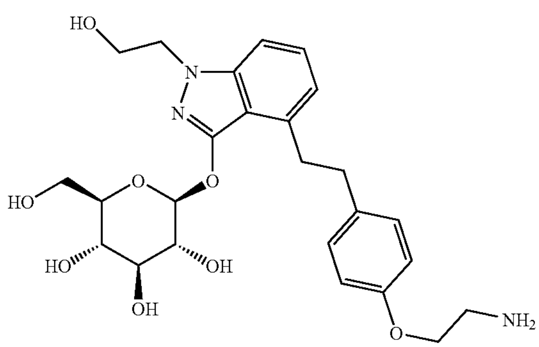 | 2.8-3.0(4H, m), 3.1-3.2(1H, m), 3.25-3.65(5H, m), 3.69(1H, dd, J=11.9Hz, 5.7Hz), 3.85-3.95(3H, m), 3.97(2H, t, J=5.3Hz), 4.29(2H, t, J=5.4Hz), 5.72(1H, d, J=7.8Hz), 6.75 (1H, dd, J=6.0Hz, 1.5Hz), 6.8-6.9(2H, m), 7.1-7.3(4H, m) |
| Example 86 | 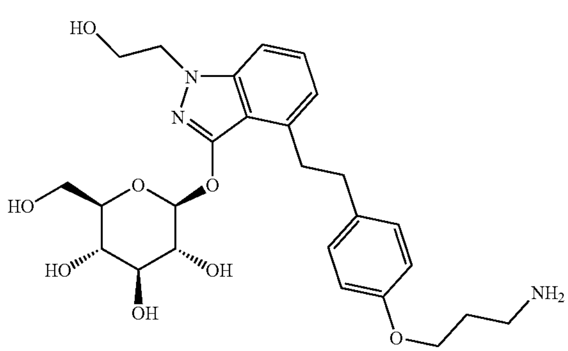 | 1.8-2.0(2H, m), 2.75-3.0(4H, m), 3.05-3.2(1H, m), 3.25-3.65(5H, m), 3.69(1H, dd, J=12.0Hz, 5.7Hz), 3.8-3.95(3H, m), 4.02(2H, t, J=6.2Hz), 4.29(2H, t, J=5.5Hz), 5.72 (1H, d J=8.0Hz) 6.7-6.9(3H, m), 7.1-7.3(4H, m) |

TABLE 9

| Example number | Chemical structure | $^1$H-NMR (CD$_3$OD) δ ppm |
|---|---|---|
| Example 87 | (structure) | 1.9-2.05(2H, m), 2.7-3.25(6H, m), 3.25-3.75(10H, m), 3.85-3.95(1H, m), 4.04(2H, t, J=6.1Hz), 5.64(1H, d, J=7.5Hz), 6.7-6.8(1H, m), 6.8-6.9 (2H, m), 7.1-7.3(4H, m) |

Example 88

1-Carbamoylmethyl-3-(β-D-glucopyranosyloxy)-4-[2-(4-{3-[2-hydroxy-1,1-bis(hydroxymethyl)ethylamino]propoxy}-phenyl)ethyl]-1H-indazole A mixture of 3-(β-D-glucopyranosyloxy)-4-[2-(4-{3-[2-hydroxy-1,1-bis(hydroxymethyl)ethylamino]propoxy}phenyl) -ethyl]-1H-indazole (57 mg), 2-bromoacetoamide (41 mg), cesium carbonate (97 mg) and a catalytic amount of sodium iodide in N,N-dimethylformamide (1 mL) was stirred at room temperature overnight. To the reaction mixture was added water, and the resulting mixture was purified by solid phase extraction on ODS (washing solvent: distilled water, eluent: methanol) and preparative reverse phase column chromatography (Shiseido CAPCELL PAK UG120 ODS, 5 μm, 120 Å, 20×50 mm, flow rate 30 mL/minute linear gradient, water/methanol=90/10–10/90) successively to give the title compound (7 mg).

$^1$H-NMR (CD$_3$OD) δ ppm: 1.9-2.05 (2H, m), 2.75-3.05 (4H, m), 3.1-3.25 (1H, m), 3.25-3.65 (11H, m), 3.69 (1H, dd, J=12.2 Hz, 5.9 Hz), 3.87 (1H, dd, J=12.2 Hz, 2. 0Hz), 4.0-4.1 (2H, m), 4.89 (2H, s), 5.74 (1H, d, J=7.8 Hz), 6.75-6.9 (3H, m), 7.1-7.35 (4H, m)

Example 89

4-[2-(4-Bromophenyl)ethynyl]-3-(2,3,4,6-tetra-O-pivaloyl-β-D-glucopyranosyloxy)-1-(2-pivaloyloxyethyl)-1H-indazole 4-Ethynyl-3-(2,3,4,6-tetra-O-pivaloyl-β-D-gluco -pyranosyloxy)-1-(2-pivaloyloxyethyl)-1H-indazole was prepared in a similar manner to that described in Reference Example 4 using 4-bromo-3-(2,3,4,6-tetra-O-pivaloyl-β-D-glucopyranosyloxy)-1-(2-pivaloyloxyethyl)-1H-indazole instead of 4-bromo-3-(2,3,4,6-tetra-O-pivaloyl-β-D-glucopyranosyloxy)-1H-indazole. Then the title compound was prepared in a similar manner to that described in Example 3 using this material and 1-bromo-4-iodobenzene instead of 4-ethynyl-3-(2,3,4,6-tetra-O-pivaloyl-β-D-glucopyranosyloxy)-1H-indazole and 4-iodo-2-methylphenol.

$^1$H-NMR (CDCl$_3$) δ ppm: 0.98 (9H, s), 1.02 (9H, s), 1.15 (9H, s), 1.16 (9H, s), 1.17 (9H, s), 3.95-4.05 (1H,m), 4.1-4.2 (1H, m), 4.24 (1H, dd, J=12.5 Hz, 1.8 Hz), 4.35-4.5 (4H, m), 5.2-5.3 (1H, m), 5.3-5.4 (1H, m), 5.4-5.5 (1H, m), 6.05 (1H, d, J=8.3 Hz), 7.2-7.35 (3H, m), 7.5-7.6 (4H, m)

Example 90

4-[2-(4-{3-[1-Carboxy-1-(methyl)ethylcarbamoyl] propyl}-phenyl)ethyl]-3-(2,3,4,6-tetra-O-pivaloyl-β-D-gluco-pyranosyloxy)-1-(2-pivaloyloxyethyl)-1H-indazole A mixture of 4-[2-(4-bromophenyl)ethynyl]-3-(2,3,4,6-tetra-O-pivaloyl-β-D-glucopyranosyloxy)-1-(2-pivaloyloxy-ethyl)-1H-indazole (0.35 g), 3-butenoicacid (64 mg), palladium (II) acetate (4 mg) and tris(2-methylphenyl)phosphine (11 mg) in triethylamine (4 mL) was stirred at 80° C. under an argon atmosphere for 2 hours. The reaction mixture was cooled to room temperature and diluted with ethyl acetate. To the mixture was added 2 mol/L hydrochloric acid (15 mL), and the resulting mixture was stirred at 30 minutes. The insoluble material was removed by filtration, and the organic layer was separated. The organic layer was washed with water and brine, and dried over anhydrous sodium sulfate. The solvent was removed under reduced pressure, and the residue was dissolved in N,N-dimethylformamide (5 mL). To the solution were added benzyl 2-amino-2-methylpropionate hydrochloride (WO2004/014932A1, 0.26 g), 1-hydroxybenzotriazole (0.15 g), 1-ethyl-3-(3-dimethylaminopropyl)carbodiimide hydrochloride (0.32 g) and triethylamine (0.52 mL), and the mixture was stirred at 45° C. for 3 days. The reaction mixture was poured into water, and the resulting mixture was extracted with ethyl acetate. The extract was washed with 1 mol/L hydrochloric acid, water, a saturated aqueous sodium hydrogen carbonate solution, water and brine successively, and dried over anhydrous sodium sulfate. The solvent was removed under reduced pressure, and the residue was purified by column chromatography on silica gel (eluent: n-hexane/ethyl acetate=3/1-2/1-3/2) and aminopropylated silica gel (eluent: n-hexane/ ethyl acetate=3/2-1/1) successively to give 4-[2-(4-{(E)-3-[1-benzyloxycarbonyl-1-(methyl)ethylcarbamoyl]prop-1-enyl}phenyl)ethynyl]-3-(2,3,4,6-tetra-O-pivaloyl-β-D-glucopyranosyloxy)-1-(2-pivaloyloxyethyl)-1H-indazole (0.3 g). This material was dissolved in ethyl acetate (6 mL). To the solution was added 10% palladium-carbonpowder (0.15 g), and the mixture was stirred at room temperature under a hydrogen atmosphere for 4 hours. The insoluble material was removed by filtration, and the solvent of the filtrate was removed under reduced pressure to give the title compound (0.27 g).

¹H-NMR (CDCl₃) δ ppm: 1.01 (9H, s), 1.02 (9H, s), 1.11 (9H, s), 1.14 (9H, s), 1.18 (9H, s), 1.55-1.65 (6H, m), 1.9-2.05 (2H, m), 2.15-2.25 (2H, m), 2.6-2.7 (2H, m), 2.8-2.9 (1H, m), 2.9-3.15 (2H, m), 3.2-3.35 (1H, m), 3.95-4.05 (1H, m), 4.14 (1H, dd, J=12.5 Hz, 5.0 Hz), 4.21 (1H, dd, J=12.5 Hz, 1.7 Hz), 4.3-4.5 (4H, m), 5.25-5.35 (1H, m), 5.4-5.55 (2H, m), 6.0-6.1 (2H, m), 6.72 (1H, d, J=7.0 Hz), 7.05-7.25 (6H, m)

Examples 91 to 92

The compounds described in Table 10 were prepared in a similar manner to that described in Example 90 using the corresponding starting materials.

added 1-(2-hydroxyethyl)piperazine (6 mg), 1-hydroxybenzotriazole (6 mg), 1-ethyl-3-(3-dimethylaminopropyl)carbodiimide hydrochloride (11 mg) and triethylamine (0.016 mL), and the mixture was stirred at 50° C. overnight. The reaction mixture was poured into water, and the resulting mixture was extracted with ethyl acetate. The extract was washed with water, a saturated aqueous sodium hydrogen carbonate solution and brine, and dried over anhydrous sodium sulfate. The solvent was removed under reduced pressure, and the residue was purified by column chromatography on silica gel (eluent: dichloromethane/methanol=10/1-8/1) to give 4-[2-(4-{3-[1-{[4-(2-hydroxyethyl)-piperazin-1-yl]carbonyl}-1-(methyl)ethylcarbamoyl]propyl}-phenyl)ethyl]-3-(2,3,4,6-tetra-O-pivaloyl-β-D-glucopyranosy loxy)-1-(2-pivaloyloxyethyl)-1H-indazole

TABLE 10

| Example number | Chemical structure | ¹H-NMR δ ppm |
|---|---|---|
| Example 91 | 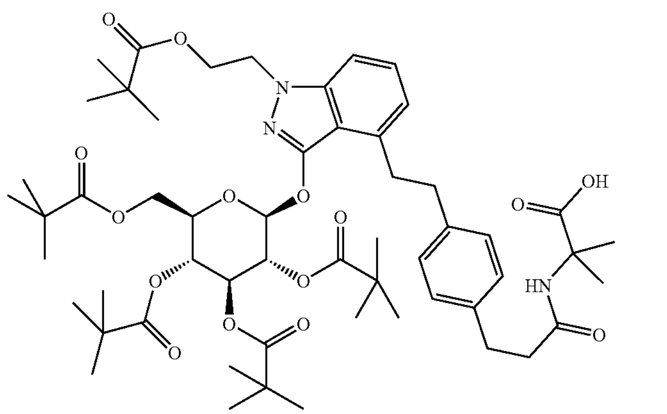 | (CDCl₃) 1.017(9H, s), 1.023(9H, s), 1.12(9H, s), 1.15(9H, s), 1.17(9H, s), 1.49(6H, s), 2.53(2H, t, J=7.3Hz), 2.8-2.9(1H, m), 2.9-3.15(4H, m), 3.2-3.3(1H, m), 3.95-4.05(1H, m), 4.14(1H, dd, J=12.5Hz, 5.0Hz), 4.21 (1H, dd, J=12.5Hz, 1.7Hz), 4.3-4.5 (4H, m), 5.2-5.3(1H, m), 5.35-5.45 (1H, m), 5.45-5.55(1H, m), 5.86(1H, brs), 6.06(1H, d, J=8.1Hz), 6.7(1H, d, J=6.9Hz), 7.05-7.25(6H, m) |
| Example 92 | 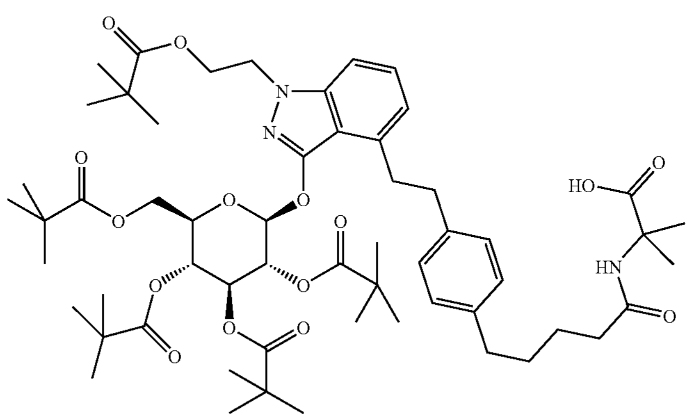 | (CD₃OD) 0.91(9H, s), 1.03(9H, s), 1.07(9H, s), 1.16(9H, s), 1.17(9H, s), 1.45(6H, s), 1.55-1.7(4H, m), 2.15-2.25(2H, m), 2.55-2.65(2H, m), 2.7-2.85(1H, m), 2.85-3.1(2H, m), 3.15-3.35(1H, m), 4.05-4.3(3H, m), 4.35-4.6(4H, m), 5.2-5.4(2H, m), 5.5-5.6(1H, m), 6.16(1H, d, J=8.2Hz), 6.65-6.75(1H, m), 7.0-7.3 (6H, m) |

Example 93

3-(β-D-Glucopyranosyloxy)-1-(2-hydroxyethyl)-4-[2-(4-{3-[1-{[4-(2-hydroxyethyl)piperazin-1-yl]carbonyl}-1-(methyl)-ethylcarbamoyl]propyl}phenyl)ethyl]-1H-indazole To a solution of 4-[2-(4-{3-[1-carboxy-1-(methyl)ethylcarbamoyl]propyl}phenyl)ethyl]-3-(2,3,4,6-tetra-O-pivaloyl-β-D-glucopyranosyloxy)-1-(2-pivaloyloxyethyl)-1H-indazole (40 mg) in N,N-dimethylformamide (1 mL) were (22 mg). This material was dissolved in methanol (2 mL). To the solution was added lithium hydroxide monohydrate (8 mg), and the mixture was stirred at room temperature overnight. To the reaction mixture was added acetic acid (0.1 mL), and the resulting mixture was concentrated under reduced pressure. To the residue was added a saturated aqueous potassium carbonate solution, and the mixture was purified by solid phase extraction on ODS (washing solvent: distilled water, eluent:methanol) to give the title compound (11 mg).

¹H-NMR (CD₃OD) δ ppm: 1.43 (6H, s), 1.8-1.95 (2H, m), 2.19 (2H, t, J=7.7 Hz), 2.4-2.55 (6H, m), 2.61 (2H, t, J=7.4 Hz), 2.85-3.05 (2H, m), 3.1-3.2 (1H, m), 3.25-3.75 (12H, m), 3.85-3.95 (3H, m), 4.3 (2H, t, J=5.3 Hz), 5.73 (1H, d, J=7.7 Hz), 6.75-6.85 (1H, m), 7.05-7.15 (2H, m), 7.15-7.3 (4H, m)

Examples 94 to 106

The compounds described in Tables 11 to 14 were prepared in a similar manner to that described in Example 22 or Example 93 using the corresponding starting materials.

TABLE 11

| Example number | Chemical structure | ¹H-NMR(CD₃OD) δ ppm |
| --- | --- | --- |
| Example 94 | 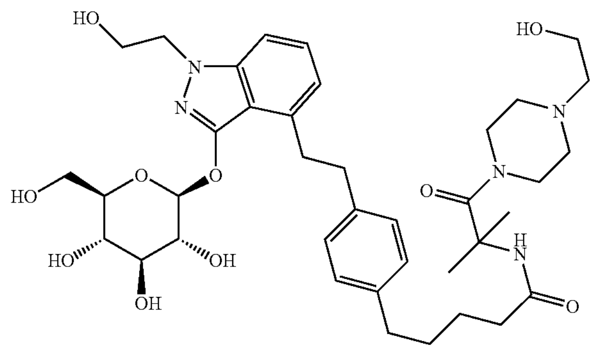 | 1.43(6H, s), 1.55-1.7(4H, m), 2.2 (2H, t, J=6.9Hz), 2.35-2.55(6H, m), 2.6(2H, t, J=7.0Hz), 2.85-3.05(2H, m), 3.1-3.2(1H, m), 3.25-3.75(12H, m), 3.85-3.95(3H, m), 4.3(2H, t, J=5.5Hz), 5.73(1H, d, J=7.9Hz), 6.77 (1H, dd, J=5.9Hz, 1.6Hz), 7.05-7.15 (2H, m), 7.15-7.3(4H, m) |
| Example 95 | 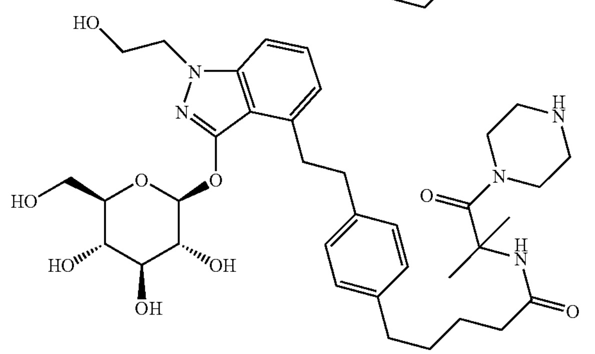 | 1.42(6H, s), 1.55-1.7(4H, m), 2.19 (2H, t, J=7.1Hz), 2.6(2H, t, J=6.5Hz), 2.65-2.8(4H, m), 2.85-3.05(2H, m), 3.1-3.2(1H, m), 3.25-3.75(10H, m), 3.85-3.95(3H, m), 4.3(2H, t, J=5.5Hz), 5.73(1H, d, J=7.9Hz), 6.78 (1H, dd, J=5.8Hz, 1.7Hz), 7.05-7.15 (2H, m), 7.15-7.3(4H, m) |
| Example 96 | 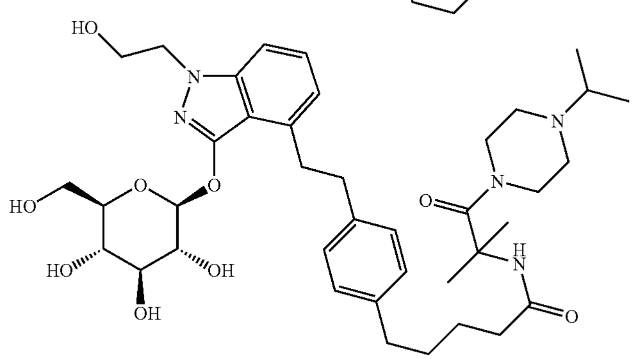 | 1.03(6H, d, J=6.4Hz), 1.43(6H, s), 1.55-1.7(4H, m), 2.2(2H, t, J=7.1Hz), 2.4-2.55(4H, m), 2.55-2.7(3H, m), 2.85-3.05(2H, m), 3.1-3.2(1H, m), 3.25-3.75(10H, m), 3.85-3.95 (3H, m), 4.3(2H, t, J=5.6Hz), 5.73 (1H, d, J=7.9Hz), 6.77(1H, dd, J=6.0Hz, 1.6Hz), 7.05-7.15(2H, m), 7.15-7.3(4H, m) |
| Example 97 | 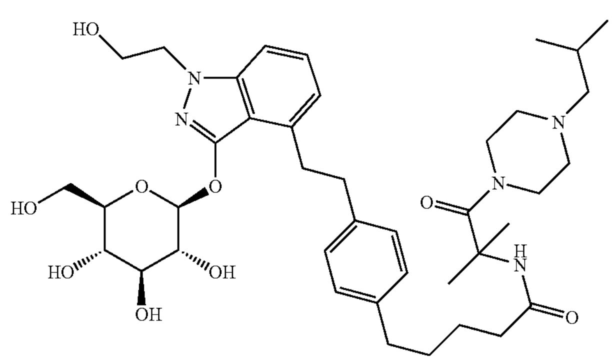 | 0.9(6H, d, J=6.8Hz), 1.43(6H, s), 1.55-1.7(4H, m), 1.7-1.85(1H, m), 2.07(2H, d, J=7.2Hz), 2.2(2H, t, J=6.7Hz), 2.25-2.45(4H, m), 2.55-2.65 (2H, m), 2.85-3.05(2H, m), 3.1-3.2(1H, m), 3.25-3.75(10H, m), 3.85-3.95(3H, m), 4.3(2H, t, J=5.4Hz), 5.73(1H, d, J=7.9Hz), 6.7-6.8(1H, m), 7.05-7.15(2H, m), 7.15-7.3(4H, m) |

TABLE 12

| Example number | Chemical structure | ¹H-NMR(CD₃OD) δ ppm |
|---|---|---|
| Example 98 | 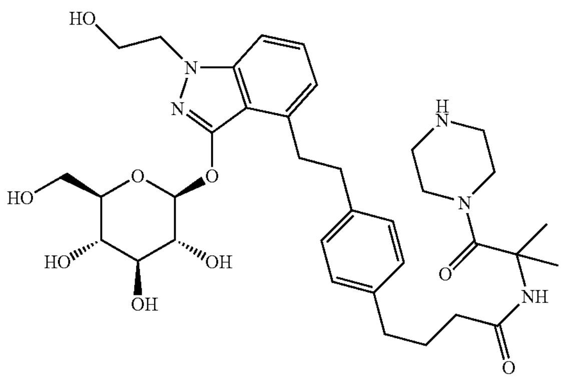 | 1.43(6H, s), 1.8-1.95(2H, m), 2.19 (2H, t, J=7.8Hz), 2.61(2H, t, J=7.5Hz), 2.65-2.8(4H, m), 2.85-3.05(2H, m), 3.1-3.2(1H, m), 3.25-3.75(10H, m), 3.85-3.95(3H, m), 4.3(2H, t, J=5.5Hz), 5.73(1H, d, J=8.0Hz), 6.78 (1H, dd, J=5.8Hz, 1.8Hz), 7.05-7.15 (2H, m), 7.15-7.3(4H, m) |
| Example 99 | 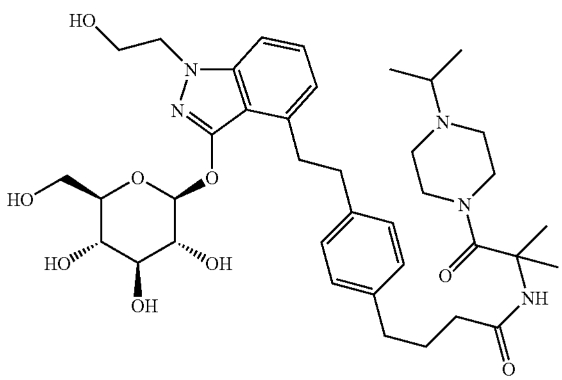 | 1.04(6H, d, J=6.4Hz), 1.43(6H, s), 1.8-1.95(2H, m), 2.19(2H, t, J=7.7Hz), 2.4-2.55(4H, m), 2.55-2.7 (3H, m), 2.85-3.05(2H, m), 3.1-3.2 (1H, m), 3.25-3.75(10H, m), 3.85-3.95 (3H, m), 4.3(2H, t, J=5.5Hz), 5.73 (1H, d, J=8.0Hz), 6.77(1H, dd, J=5.9Hz, 1.3Hz), 7.05-7.15(2H, m), 7.15-7.3(4H, m) |
| Example 100 | 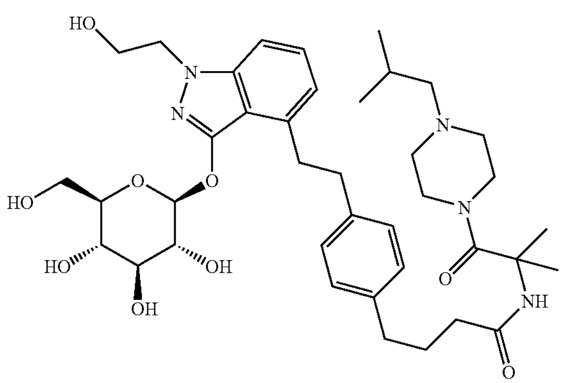 | 0.9(6H, d, J=6.5Hz), 1.43(6H, s), 1.7-1.95 (3H, m), 2.08(2H, d, J=7.2Hz), 2.19(2H, t, J=7.6Hz), 2.25-2.4(4H, m), 2.61(2H, t, J=7.7Hz), 2.85-3.05 (2H, m), 3.1-3.2(1H, m), 3.25-3.75 (10H, m), 3.85-3.95(3H, m), 4.3(2H, t, J=5.5Hz), 5.73(1H, d, J=7.8Hz), 6.7-6.8(1H, m), 7.05-7.15(2H, m), 7.15-7.3(4H, m) |
| Example 101 | 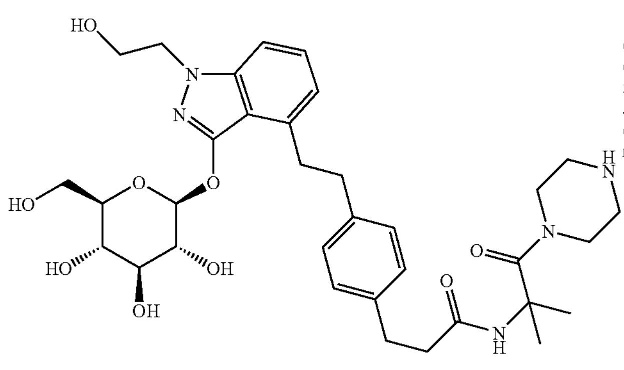 | 1.367(3H, s), 1.370(3H, s), 2.4-3.05 (10H, m), 3.1-3.2(1H, m), 3.25-3.6 (9H, m), 3.69(1H, dd, J=12.1Hz, 5.5Hz), 3.85-3.95(3H, m), 4.3(2H, t, J=5.5Hz), 5.73(1H, d, J=7.6Hz), 6.77 (1H, dd, J=6.0Hz, 1.3Hz), 7.1-7.3(6H, m) |

TABLE 13

| Example number | Chemical structure | $^1$H-NMR(CD$_3$OD) δ ppm |
|---|---|---|
| Example 102 | 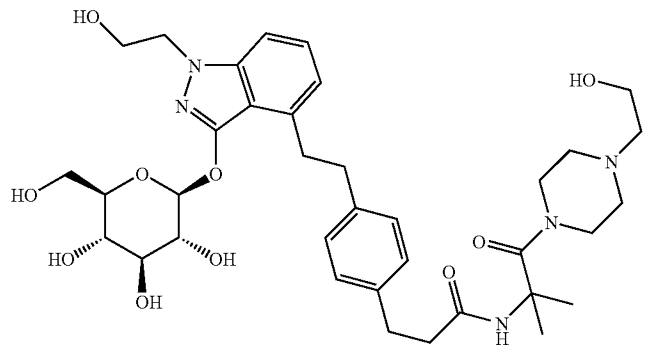 | 1.369(3H, s), 1.372(3H, s), 2.25-2.55 (8H, m), 2.8-3.05(4H, m), 3.1-3.2(1H, m), 3.25-3.75(12H, m), 3.85-3.95(3H, m), 4.3(2H, t, J=5.6Hz), 5.73(1H, d, J=7.8Hz) 6.7-6.8(1H, m) 7.05-7.3 (6H, m) |
| Example 103 | 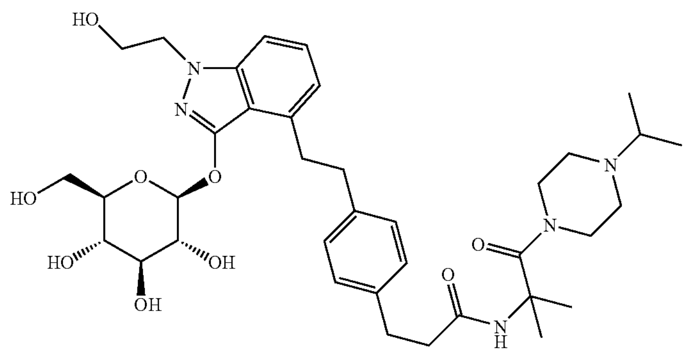 | 0.95-1.1(6H, m), 1.372(3H, s), 1.375 (3H, s), 2.3-2.55(6H, m), 2.55-2.7 (1H, m), 2.8-3.05(4H, m), 3.1-3.2(1H, m), 3.25-3.65(9H, m), 3.69(1H, dd, J=12.3Hz, 5.7Hz), 3.85-3.95(3H, m), 4.3(2H, t, J=5.8Hz), 5.73(1H, d, J=7.8Hz), 6.7-6.8(1H, m), 7.1-7.3 (6H, m) |
| Example 104 | 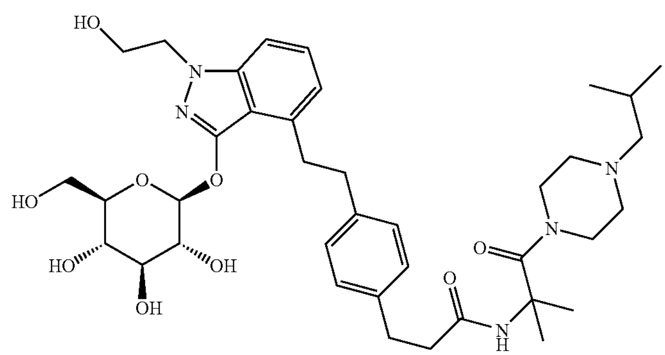 | 0.8-0.95(6H, m), 1.367(3H, s), 1.370 (3H, s), 1.7-1.85(1H, m), 2.06(2H, d, J=7.4Hz), 2.15-2.45(4H, m), 2.48 (2H, t, J=7.1Hz), 2.8-3.05(4H, m), 3.1-3.2(1H, m), 3.25-3.65(9H, m), 3.69(1H, dd, J=12.1Hz, 5.7Hz), 3.85-3.95(3H, m), 4.3(2H, t, J=5.8Hz), 5.73(1H, d, J=8.0Hz), 6.7-6.8(1H, m), 7.1-7.3(6H, m) |
| Example 105 | 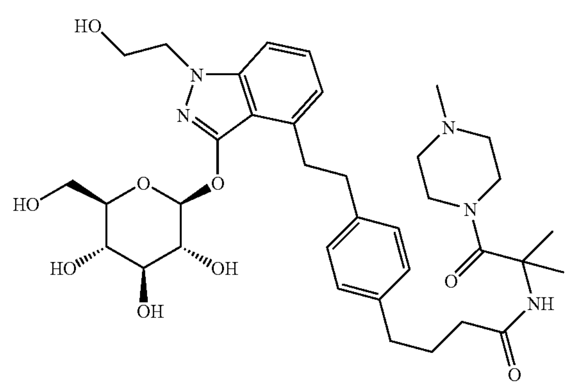 | 1.43(6H, s), 1.8-1.95(2H, m), 2.19 (2H, t, J=7.7Hz), 2.26(3H, s), 2.3-2.45(4H, m), 2.61(2H, t, J=7.5Hz), 2.85-3.05(2H, m), 3.1-3.2 (1H, m), 3.25-3.75(10H, m), 3.85-3.95 (3H, m), 4.3(2H, t, J=5.5Hz), 5.73 (1H, d, J=7.8Hz), 6.78(1H, dd, J=5.9Hz, 1.5Hz), 7.05-7.15(2H, m), 7.15-7.3(4H, m) |

TABLE 14

| Example number | Chemical structure | ¹H-NMR(CD₃OD) δ ppm |
|---|---|---|
| Example 106 | 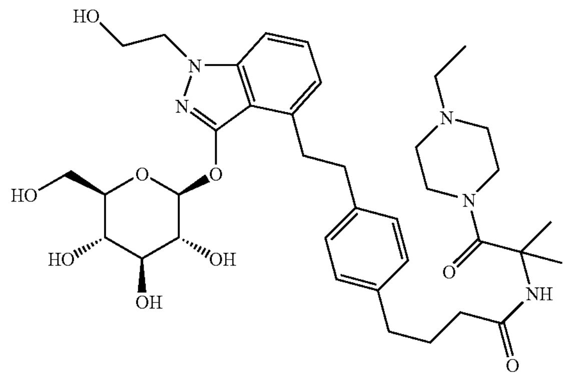 | 1.09(3H, t, J=7.3Hz), 1.43(6H, s), 1.8-1.95(2H, m), 2.19(2H, t, J=7.8Hz), 2.3-2.5(6H, m), 2.61(2H, t, J=7.4Hz), 2.85-3.05(2H, m), 3.1-3.2 (1H, m), 3.25-3.75(10H, m), 3.85-3.95 (3H, m), 4.3(2H, t, J=5.5Hz), 5.73 (1H, d, J=8.0Hz), 6.77(1H, dd, J=6.0Hz, 1.4Hz), 7.05-7.15(2H, m), 7.15-7.3(4H, m) |

Example 107

4-{2-[4-(3-Aminopropoxy)phenyl]ethyl}-1-carbamoylmethyl-3-(β-D-glucopyranosyloxy)-1H-indazole To a solution of 4-{2-[4-(3-hydroxypropoxy)phenyl]ethyl}-3-(2,3,4,6-tetra-O-pivaloyl-β-D-glucopyranosyloxy)-1H-indazole (0.35 g) and triethylamine (0.089 mL) in dichloromethane (4 mL) was added methane sulfonyl chloride (0.036 mL), and the mixture was stirred at room temperature for 1 hour. The reaction mixture was poured into 0.5 mol/L hydrochloric acid, and the resulting mixture was extracted with diethyl ether. The extract was washed with water and brine, and dried over anhydrous sodium sulfate. The solvent was removed under reduced pressure to give 4-{2-[4-(3-methanesulfonyloxy propoxy)phenyl]ethyl}-3-(2,3,4,6-tetra-O-pivaloyl-β-D-glucopyranosyloxy)-1H-indazole (0.35 g). The obtained compound (0.1 g) was dissolved in N,N-dimethylformamide (1 mL). To the solution was added sodium azide (11 mg), and the mixture was stirred at 100° C. for 2 hours. The reaction mixture was poured into water, and the resulting mixture was extracted with diethyl ether. The extract was washed with water and brine, and dried over anhydrous sodium sulfate. The solvent was removed under reduced pressure, and the residue was purified by column chromatography on silica gel (eluent:n-hexane/ethyl acetate=3/1-2/1) to give 4-{2-[4-(3-azidopropoxy)phenyl]ethyl}-3-(2,3,4,6-tetra-O-pivaloyl-β-D-glucopyranosyloxy)-1H-indazole (76 mg). This material was dissolved in a mixed solvent of methanol (1 mL) and tetrahydrofuran (1 mL). To the solution was added lithium hydroxide monohydrate (19 mg), and the mixture was stirred at room temperature overnight. To the reaction mixture was added acetic acid (0.05 mL), and the resulting mixture was concentrated under reduced pressure. To the residue was added a saturated aqueous sodium hydrogen carbonate solution, and the mixture was purified by solid phase extraction on ODS (washing solvent: distilled water, eluent:methanol) to give 4-{2-[4-(3-azidopropoxy)phenyl]ethyl}-3-(β-D-glucopyranosyloxy)-1H-indazole (44 mg). This material was dissolved in N,N-dimethylformamide (1 mL). To the solution were added 2-bromoacetoamide (24 mg), cesium carbonate (57 mg) and a catalytic amount of sodium iodide, and the mixture was stirred at room temperature for 3 days. To the reaction mixture was added water, and the resulting mixture was purified by solid phase extraction on ODS (washing solvent:distilled water, eluent: methanol) and column chromatography on silica gel (eluent: dichloromethane/methanol=8/1-5/1) successively to give 4-{2-[4-(3-azidopropoxy)phenyl]ethyl}-1-carbamoyl-methyl-3-(β-D-glucopyranosyloxy)-1H-indazole (36 mg). To this material were added methanol (3 mL), tetrahydrofuran (3 mL) and 10% palladium-carbon powder (30 mg), and the mixture was stirred at room temperature under a hydrogen atmosphere for 2 hours. The insoluble material was removed by filtration, and the solvent of the filtrate was removed under reduced pressure. The residue was treated with ethyl acetate and collected by filtration. The solid was washed with diethyl ether and dried under reduced pressure to give the title compound (10 mg).

¹H-NMR (CD₃OD) δ ppm: 1.9-2.05 (2H, m), 2.8-3.05 (4H, m), 3.1-3.2 (1H, m), 3.25-3.65 (5H, m), 3.69 (1H, dd, J=12.2 Hz, 5.7 Hz), 3.88 (1H, dd, J=12.2 Hz, 2.2 Hz), 4.04 (2H, t, J=6.1 Hz), 4.85-5.0 (2H, m), 5.74 (1H, d, J=7.8 Hz), 6.75-6.9 (3H, m), 7.1-7.35 (4H, m)

Example 108

4-[2-(4-{(E)-3-[1-{[4-(Benzyloxycarbonyl)piperazin-1-yl]-carbonyl}-1-(methyl)ethylcarbamoyl] prop-1-enyl}phenyl)-ethynyl]-3-(2,3,4,6-tetra-O-pivaloyl-β-D-glucopyranosyl-oxy)-1H-indazole 4-(2-{4-[(E)-3-Carboxyprop-1-enyl]phenyl}ethynyl)-3-(2,3,4,6-tetra-O-pivaloyl-β-D-glucopyranosyloxy)-1H-indazole (0.19 g), which was prepared in a similar manner to that described in Example 3 and Example 21 using the corresponding starting materials, was dissolved in N,N-dimethylformamide (3 mL). To the solution were added 1-(2-amino-2-methylpropionyl)-4-(benzyloxycarbonyl)piperazine (WO2004/014932A1, 0.16 g), 1-hydroxybenzotriazole (93 mg), 1-ethyl-3-(3-dimethylamino-propyl)carbodiimide hydrochloride (0.13 g) and triethylamine (0.16 mL), and the mixture was stirred at room temperature for 2 hours. The reaction mixture was diluted with diethyl ether, and the resulting mixture was washed with water, a saturated aqueous sodium hydrogen carbonate solution, water and brine, and dried over anhydrous magnesium sulfate. The solvent was removed under reduced pressure, and the residue was purified by column chromatography on silica gel (eluent:

n-hexane/ethyl acetate=1/1-dichloromethane/methanol=40/1) to give the title compound (0.12 g).

¹H-NMR (CDCl₃) δ ppm: 1.01 (9H, s), 1.15 (9H, s), 1.16 (9H, s), 1.17 (9H, s), 1.57 (6H, s), 3.15-3.2 (2H, m), 3.45-3.75 (8H, m), 3.95-4.05 (1H, m), 4.13 (1H, dd, J=12.4 Hz, 5.6 Hz), 4.24 (1H, dd, J=12.4 Hz, 1.8 Hz), 5.15 (2H, s), 5.2-5.3 (1H, m), 5.35-5.5 (2H, m), 6.05 (1H, d, J=8.0 Hz), 6.3-6.4 (1H, m), 6.5-6.65 (2H, m), 7.2-7.45 (10H, m), 7.6-7.65 (2H, m), 9.04 (1H, s)

Example 109

3-(β-D-Glucopyranosyloxy)-4-{2-[4-(3-{1-[(piperazin-1-yl)-carbonyl]-1-(methyl)ethylcarbamoyl}propyl)phenyl]ethyl}-1H-indazole To a solution of 4-[2-(4-{(E)-3-[1-{[4-(benzyloxy-carbonyl)piperazin-1-yl]carbonyl}-1-(methyl)ethyl-carbamoyl]prop-1-enyl}phenyl)ethynyl]-3-(2,3,4,6-tetra-O-pivaloyl-β-D-glucopyranosyloxy)-1H-indazole (34 mg) in methanol (3 mL) was added 10% palladium-carbon powder (10 mg), and the mixture was stirred at room temperature under a hydrogen atmosphere for 2 hours. The insoluble material was removed by filtration, and the solvent of the filtrate was removed under reduced pressure to give 4-{2-[4-(3-{1-[(piperazin-1-yl)-carbonyl]-1-(methyl)ethylcarbamoyl}propyl)phenyl]ethyl}-3-(2,3,4, 6-tetra-O-pivaloyl-β-D-glucopyranosyloxy)-1H-indazole (30 mg). This material was dissolved in methanol (3 mL). To the solution was added lithium hydroxide monohydrate (6 mg), and the mixture was stirred at room temperature overnight. To the reaction mixture was added acetic acid (0.1 mL), and the resulting mixture was concentrated under reduced pressure. The residue was purified by solid phase extraction on ODS (washing solvent: distilled water, eluent:methanol) to give the title compound (17 mg).

¹H-NMR (CD₃OD) δ ppm: 1.43 (6H, s), 1.8-1.95 (2H, m), 2.19 (2H, t, J=7.8 Hz), 2.61 (2H, t, J=7.5 Hz), 2.65-2.8 (4H, m), 2.85-3.05 (2H, m), 3.1-3.2 (1H, m), 3.25-3.75 (10H, m), 3.88 (1H, dd, J=12.1 Hz, 1.8 Hz), 5.65 (1H, d, J=8.0 Hz), 6.78 (1H, d, J=6.9 Hz), 7.05-7.3 (6H, m)

Example 110

1-Carbamoylmethyl-3-(β-D-glucopyranosyloxy)-4-{2-[4-(3-{1-[(piperazin-1-yl)carbonyl]-1-(methyl)ethylcarbamoyl}-propyl)phenyl]ethyl}-1H-indazole To a solution of 4-[2-(4-{(E)-3-[1-{[4-(benzyloxy-carbonyl)piperazin-1-yl]carbonyl}-1-(methyl)ethyl-carbamoyl]prop-1-enyl}phenyl)ethynyl]-3-(2,3,4,6-tetra-O-pivaloyl-β-D-glucopyranosyloxy)-1H-indazole (73 mg) in acetone (4 mL) were added 2-bromoacetoamide (18 mg), cesium carbonate (54 mg) and a catalytic amount of sodium iodide, and the mixture was stirred at room temperature for 5 hours. The reaction mixture was diluted with diethyl ether, and the resulting mixture was washed with water twice and brine, and dried over anhydrous magnesium sulfate. The solvent was removed under reduced pressure, and the residue was purified by column chromatography on silica gel (eluent: dichloromethane/methanol=40/1-30/1) to give 4-[2-(4-{(E)-3-[1-{[4-(benzyloxycarbonyl)piperazin-1-yl]carbonyl}-1-(methyl)ethylcarbamoyl]prop-1-enyl}-phenyl)ethynyl]-1-carbamoylmethyl-3-(2,3,4,6-tetra-O-pivaloyl-β-D-glucopyranosyloxy)-1H-indazole (54 mg). The title compound (10 mg) was prepared in a similar manner to that described in Example 109 using this material as the starting material.

¹H-NMR (CD₃OD) δ ppm: 1.43 (6H, s), 1.8-1.95 (2H, m), 2.19 (2H, t, J=7.7 Hz), 2.5-2.85 (6H, m), 2.85-3.05 (2H, m), 3.1-3.25 (1H, m), 3.25-3.75 (10H, m), 3.87 (1H, dd, J=12.0 Hz, 2.0 Hz), 4.8-4.95 (2H, m), 5.75 (1H, d, J=7.9 Hz), 6.85 (1H, d, J=6.8 Hz), 7.05-7.35 (6H, m)

Example 111

4-Benzyl-1-(2-hydroxyethyl)-3-(β-D-glucopyranosyloxy)-1H-indazole

To a suspension of 1-(2-benzyloxyethyl)-4-bromo-3-(2,3,4,6-tetra-O-pivaloyl-β-D-glucopyranosyloxy)-1H-indazole (0.17 g) and tetrakis(triphenylphosphine)palladium (0) (12 mg) in tetrahydrofuran (2 mL) was added benzylzinc bromide (0.5 mol/L tetrahydrofuran solution, 0.8 mL), and the mixture was stirred at 60° C. under an argon atmosphere overnight. The reaction mixture was poured into 0.5 mol/L hydrochloric acid, and the resulting mixture was extracted with diethyl ether. The extract was washed with water and brine, and dried over anhydrous sodium sulfate. The solvent was removed under reduced pressure, and the residue was purified by column chromatography on silica gel (eluent:n-hexane/ethyl acetate=5/1-5/2) to give 4-benzyl-1-(2-benzyloxyethyl)-3-(2,3,4,6-tetra-O-pivaloyl-β-D-glucopyranosyloxy)-1H-indazole (40 mg). This material was dissolved in ethyl acetate (3 mL). To the solution was added 10% palladium-carbon powder (20 mg), and the mixture was stirred at room temperature under a hydrogen atmosphere for 2 hours. The insoluble material was removed by filtration, and the solvent of the filtrate was removed under reduced pressure to give 4-benzyl-1-(2-hydroxyethyl)-3-(2,3,4,6-tetra-O-pivaloyl-β-D-glucopyranosyloxy)-1H-indazole (32 mg). This material was dissolved in methanol (0.5 mL)-tetrahydrofuran (0.5 mL). To the solution was added lithium hydroxide monohydrate (9 mg), and the mixture was stirred at room temperature overnight. The reaction mixture was concentrated under reduced pressure, and the residue was purified by solid phase extraction on ODS (washing solvent:distilled water, eluent:methanol) to give the title compound (15 mg).

¹H-NMR (CD₃OD) δ ppm: 3.35-3.6 (4H, m), 3.67 (1H, dd, J=12.0 Hz, 5.4 Hz), 3.8-3.95 (3H, m), 4.29 (2H, t, J=5.6 Hz), 4.35 (1H, d, J=15.0 Hz), 4.46 (1H, d, J=15.0 Hz), 5.62 (1H, d, J=7.6 Hz), 6.7-6.8 (1H, m), 7.05-7.35 (7H, m)

The compounds described in Table 15 can be prepared in a similar manner to that described in the above Examples and Reference Examples.

TABLE 15

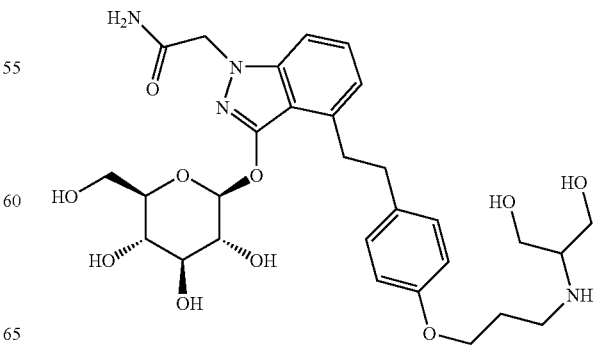

TABLE 15-continued
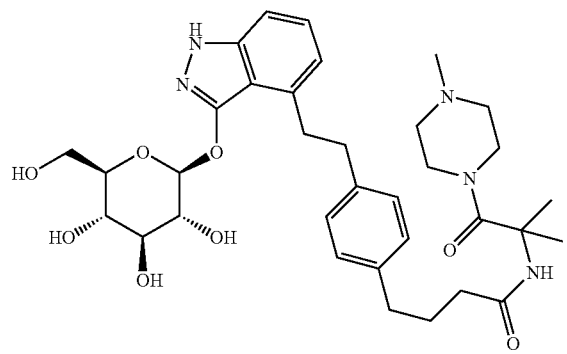
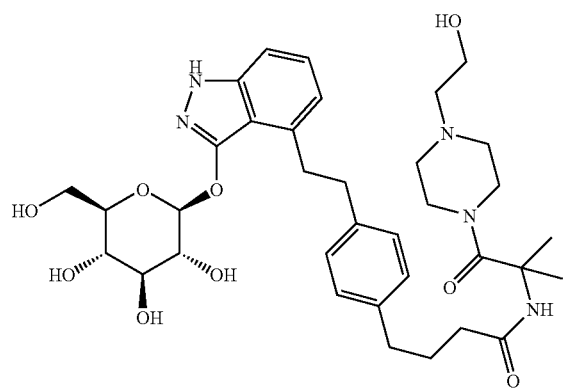
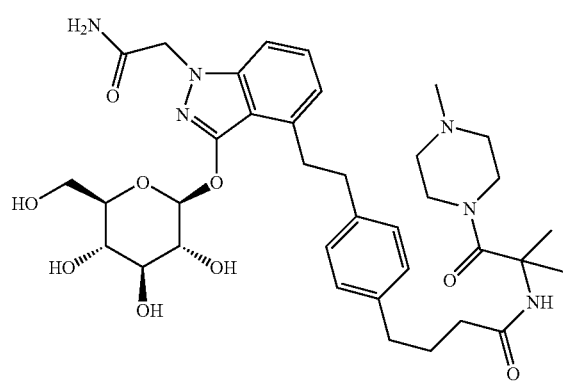
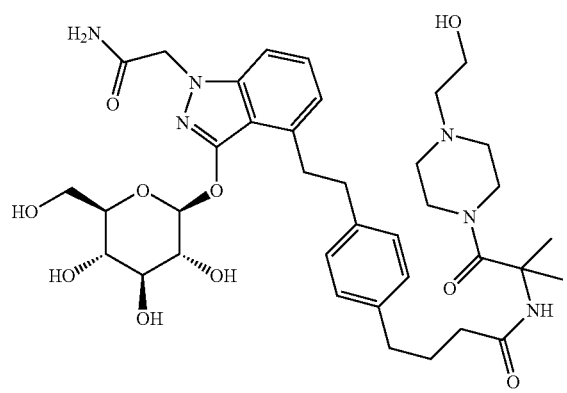
TABLE 15-continued
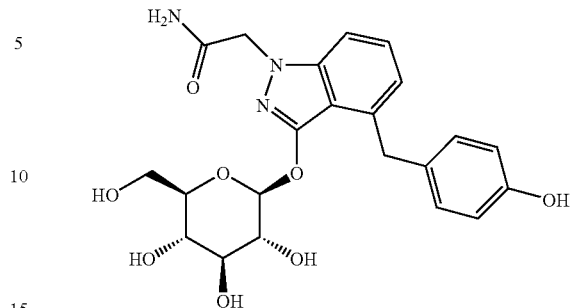
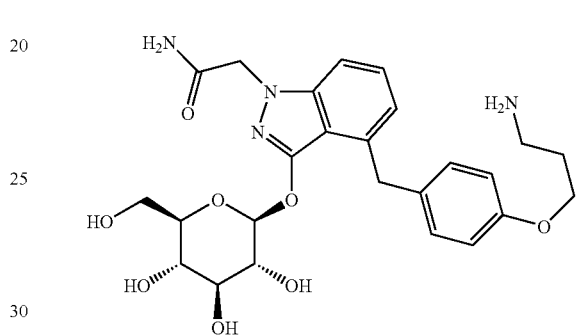
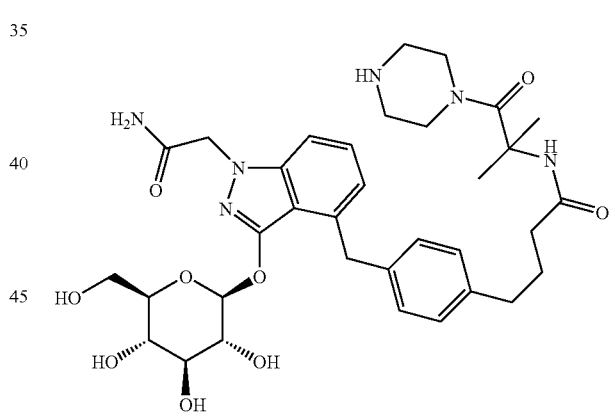
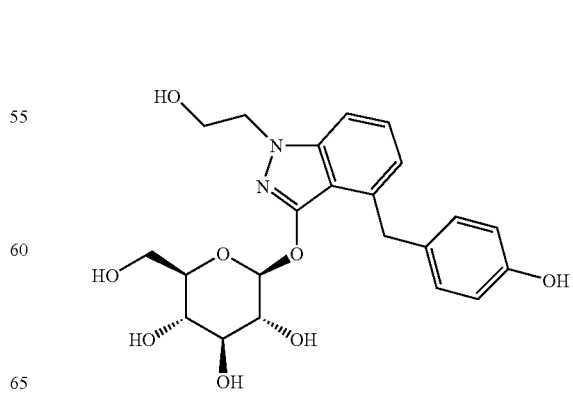

TABLE 15-continued
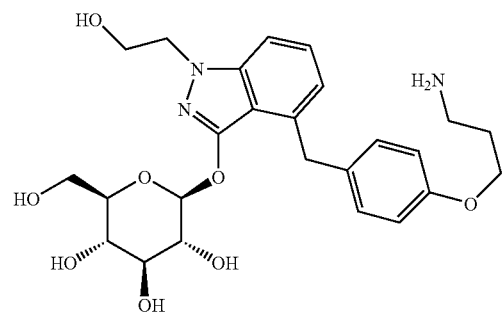
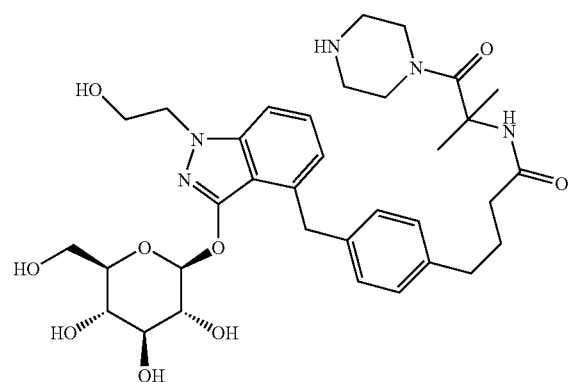
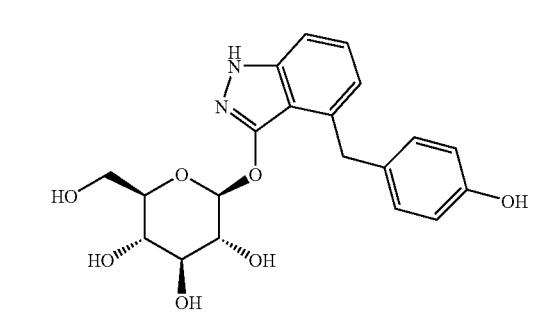
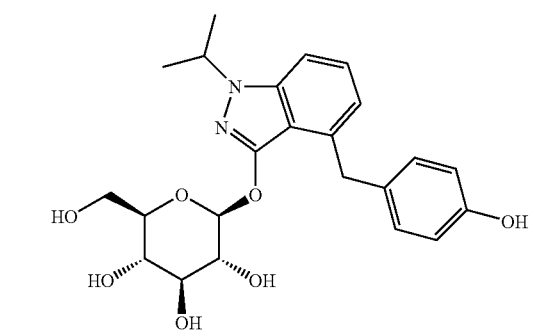
TABLE 15-continued
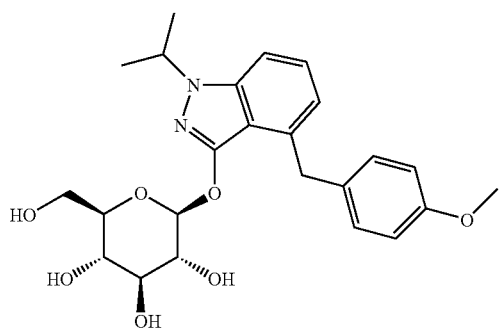
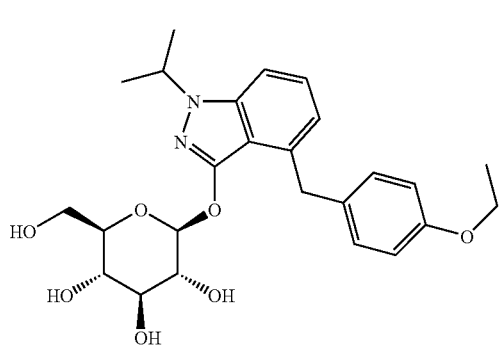
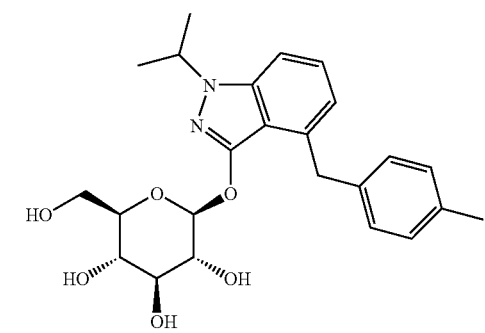
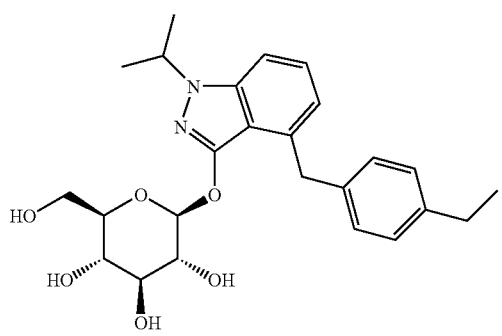

TABLE 15-continued

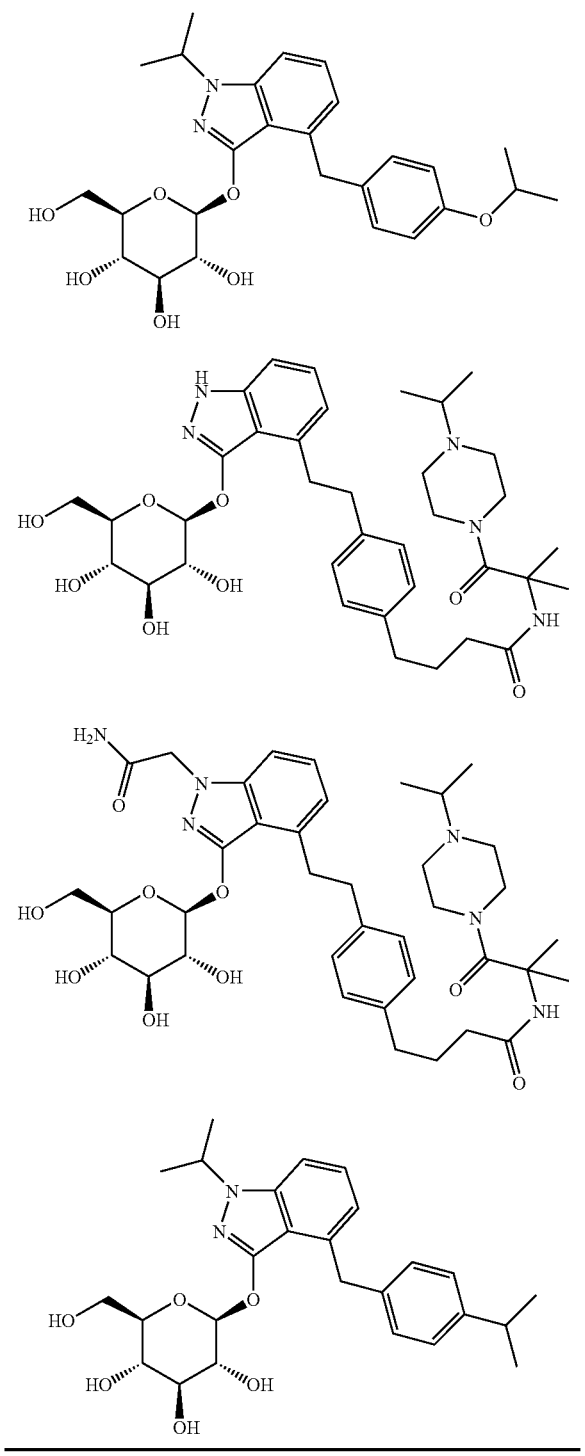

Test Example 1

Assay for Inhibitory Effects on Human SGLT1 Activity

1) Cloning and Construction of the Vector Expressing Human SGLT1

The cDNA library was prepared for PCR amplification by reverse transcription from total RNA deprived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT1

The expression vector of human SGLT1 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS1-5-11D. CS1-5-11D cells were cultured in the presence of G418 at 200 μg/mL.

3) Measurement of the Inhibitory Activity against the Uptake of methyl-(-D-glucopyranoside (α-MG)

CS1-5-11D cells were seeded into a 96-well culture plate at a density of $3 \times 10^4$ cells/well and cultured for 2 days, and were used in the uptake assay. A mixture of non-labeled (Sigma) and $^{14}C$-labeled a-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl) aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chlorine chloride instead of sodium chloride was prepared. After removing the culture medium of CS1-5-11D cells, 180 μL of the pre-treatment buffer (the basal uptake buffer without α-MG) was added to each well and incubated at 37° C. for 10 minutes. After repeating the same treatment, the pre-treatment buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter TopCount (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited ($IC_{50}$ value), was calculated using logit plot. The results are shown in Table 16.

TABLE 16

| Test compound | IC$_{50}$ value (nM) |
| --- | --- |
| Example 5 | 12 |
| Example 12 | 100 |

Test Example 2

Assay for Inhibitory Effects on Human SGLT2 Activity

1) Cloning and Construction of the Vector Expressing Human SGLT2

The cDNA library was prepared for PCR amplification by reverse transcription from total RNA deprived from human kidney (Ori gene) using oligo-dT as a primer. Using this cDNA library as a template, the DNA fragment coding 2 to 2039 bp of human SGLT2 (ACCESSION:M95549, M95299), which was reported by R. G. Wells et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT2

The expression vector of human SGLT2 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-(α-D-glucopyranoside was measured by the method described below. The cell line, which showed the greatest uptake activity, was selected and designated as CS2-5E. CS2-5E cells were cultured in the presence of G418 at 200 pg/mL.

3) Measurement of the Inhibitory Activity against the Uptake of methyl-α-D-glucopyranoside (α-MG)

CS2-5E cells were seeded into a 96-well culture plate at a density of 3×10$^4$ cells/well and cultured for 2 days, and were used in the up take assay. A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl) aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chlorine chloride instead of sodium chloride was prepared. After removing the culture medium of CS1-5-11D cells, 180 μL of the pre-treatment buffer (the basal uptake buffer without α-MG) was added to each well and incubated at 37° C. for 10 minutes. After repeating the same treatment, the pre-treatment buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter TopCount (Packard). One hundred % was set to the difference between the uptake in the control group and the basal uptake, and the uptake of methyl α-D-glucopyranoside at each drug concentration were calculated. The drug concentration, at which 50% uptake of methyl α-D-glucopyranoside was inhibited (IC$_{50}$ value), was calculated using logit plot. The results are shown in Table 17.

TABLE 17

| Test compound | IC$_{50}$ value (nM) |
| --- | --- |
| Example 4 | 90 |
| Example 17 | 68 |

Test Example 3

Assay for Inhibitory Effects on Blood Glucose Level Increase in Rats

1) Preparation of Diabetic Rat Model

Male Wistar rats (Japan Charles River), aged 8 weeks old, were injected nicotinamide (230 mg/kg) intraperitoneally. Fifteen minutes after injection, they were injected streptozotocin (85 mg/kg) intravenously from tail vain under anesthesia with ether. After a week, rats were fasted overnight and then glucose tolerance test (2 g/kg) was done. The rats which showed plasma glucose concentration at 1 hour after glucose load was over 260 mg/dL were selected to use liquidmeal tolerance test.

2) Liquid Meal Tolerance Test

After overnight fasted, the diabetic rats were orally administered a test compound (0.5, 2 mg/kg), which was dissolved in distilled water, in the drug-treating group, or distilled water alone in a control group. Immediately after the compound administration, 4.5 kcal/body of liquid meal (No. 038, Control diet, assorted with dextrin and maltose; Oriental Yeast Co., Ltd.) was loaded orally. The blood was collected from tail artery immediately before and after administration with the time course, and treated with heparin immediately. The blood was centrifuged, and the plasma was collected to quantify the plasma glucose concentration by glucose oxidase method. Plasma glucose concentrations at pretreatment (0 h), 0.5 and 1 hour after the drug administration are shown in Table 18. The values in the Table are presented as the mean±S.E.

TABLE 18

| Test compound | Plasma glucose concentration (mg/dL) | | |
| --- | --- | --- | --- |
| | 0 h | 0.5 h | 1 h |
| Control | 117 ± 2 | 224 ± 31 | 215 ± 24 |
| Example 59 0.5 mg/kg | 109 ± 2 | 173 ± 7 | 186 ± 6 |
| Example 59 2 mg/kg | 115 ± 3 | 141 ± 3 | 153 ± 4 |

INDUSTRIAL APPLICABILITY

The nitrogen-containing fused-ring derivatives represented by the above general formula (I) of the present invention, pharmaceutically acceptable salts thereof and prodrugs thereof exert an inhibitory activity in human SGLT and can suppress increase of blood glucose level or lower blood glucose level by inhibiting absorption of carbohydrate such as glucose at the small intestine or by inhibiting reabsorption of glucose at the kidney. Therefore, the present invention can provide excellent agents for the prevention or treatment of a disease associated with hyperglycemia such as diabetes, postprandial hyperglycemia, impaired glucose tolerance, diabetic complications, obesity or the like.

The invention claimed is:

1. A nitrogen-containing fused-ring derivative represented by the following general formula (I):

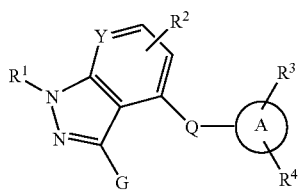

wherein $R^1$ represents a hydrogen atom, a $C_{1-6}$ alkyl group, a halo($C_{1-6}$ alkyl) group, a hydroxy($C_{1-6}$ alkyl) group, a dihydroxy($C_{1-6}$ alkyl) group, a $C_{1-6}$ alkoxy($C_{1-6}$ alkyl) group, a $C_{2-7}$ alkoxycarbonyl($C_{1-6}$ alkyl) group, a carboxy($C_{1-6}$ alkyl) group, a $C_{2-6}$ alkenyl group, -J-N($R^5$)-$Z^1$, -J-CON($R^5$)-$Z^1$, or any of the following substituents (a) to (d) which may have any 1 to 3 substituents selected from the later identified substituent group α on the ring;

(a) a $C_{3-7}$ cycloalkyl group, (b) a $C_{3-7}$ cycloalkyl($C_{1-6}$ alkyl) group, (c) a $C_{6-10}$ aryl group or (d) a $C_{6-10}$ aryl($C_{1-6}$ alkyl),group, $R^2$ represents a hydrogen atom, a halogen atom or a $C_{1-6}$ alkyl group;

$R^3$ and $R^4$ independently represent a hydrogen atom, a hydroxy group, a halogen atom, a $C_{1-6}$ alkyl group, a $C_{2-6}$ alkenyl group, a $C_{2-6}$ alkynyl group, a $C_{1-6}$ alkoxy group, a $C_{2-6}$ alkenyloxy group, a $C_{1-6}$ alkylthio group, a $C_{2-6}$ alkenylthio group, a halo ($C_{1-6}$ alkyl) group, a halo($C_{1-6}$ alkoxy) group, a halo($C_{1-6}$ alkylthio) group, a hydroxy($C_{1-6}$ alkyl) group, a hydroxy($C_{2-6}$ alkeny) group, a hydroxy($C_{1-6}$ alkoxy) group, a hydroxy($C_{1-6}$ alkylthio) group, a carboxy group, a carboxy($C_{1-6}$ alkyl) group, a carboxy($C_{2-6}$ alkenyl) group, a carboxy($C_{1-6}$ alkoxy) group, a carboxy($C_{1-6}$ alkylthio) group, a $C_{2-7}$ alkoxycarbonyl group, a $C_{2-7}$ alkoxycarbonyl($C_{1-6}$ alkyl) group, a $C_{2-7}$ alkoxycarbonyl($C_{2-6}$ alkenyl) group, a $C_{2-7}$ alkoxycarbonyl($C_{1-6}$ alkoxy) group, a $C_{2-7}$ alkoxycarbonyl($C_{1-6}$ alkylthio) group, a $C_{1-6}$ alkylsulfinyl group, a $C_{1-6}$ alkylsulfonyl group, —U—V—W—N($R^6$)-$Z^2$, or any of the following substituents (i) to (xxviii) which may have any 1 to 3 substituents selected from the later identified substituent group α on the ring;

(i) a $C_{6-10}$ aryl group, (ii) $C_{6-10}$ aryl-O—, (iii) $C_{6-10}$ aryl-S—, (iv) a $C_{6-10}$ aryl($C_{6-10}$ aryl)($C_{1-6}$ alkyl) group, (v) a $C_{6-10}$ aryl($C_{1-6}$ alkoxy) group, (vi) a $C_{6-10}$ aryl ($C_{1-6}$ alkylthio) group, (vii) a heteroaryl group, (viii) heteroaryl-O—, (ix) heteroaryl-S—, (x) a heteroaryl ($C_{1-6}$ alkyl) group, (xi) a heteroaryl($C_{1-6}$ alkdxy) group, (xii) a heteroaryl($C_{1-6}$ alkylthio) group, (xiii) a $C_{3-7}$ cycloalkyl group, (xiv) $C_{3-7}$ cycloaryl-O—, (xv) $C_{3-7}$ cycloalkyl-S—, (xvi) a $C_{3-7}$ cycloalkyl($C_{1-6}$ alkyl) group, (xvii) a $C_{3-7}$ cycloalkyl($C_{1-6}$ alkoxy) group, (xviii) a $C_{3-7}$ cycloalkyl($C_{1-6}$ alkylthio) group, (xix) a heterocycloalkyl group, (xx) heterocycloaryl-O—, (xxi) heterocycloalkyl-S—, (xxii) a heterocycloalkyl ($C_{1-6}$ alkyl) group, (xxiii) a heterocycloalkyl($C_{1-6}$ alkoxy) group, (xxiv) a heterocycloalkyl($C_{1-6}$ alkylthio) group, (xxv) an aromatic cyclic amino group, (xxvi) an aromatic cyclic amino($C_{1-6}$ alkyl) group, (xxvii) an aromatic cyclic amino($C_{1-6}$ alkoxy) group, or (xxviii) an aromatic cyclic amino($C_{1-6}$ alkylthio) group, J represents a $C_{1-6}$ alkylene group which may have a hydroxy group, or a $C_{2-6}$ alkenylene group;

U represents-O—, —S— or a single bond and with the proviso that at least one of V and W is not a single bond when U is —O— or —S—;

V represents a $C_{1-6}$ alkylene group which may have a hydroxy group, a $C_{2-6}$ alkenylene group or a single bond;

W represents —CO—, —SO$_2$—, —C(=NH)— or a single bond;

$Z^1$ and $Z^2$ independently represent a hydrogen atom, a $C_{2-7}$ alkoxycarbonyl group, a $C_{6-10}$ aryl($C_{2-7}$ alkoxycarbonyl) group, a formyl group, —$R^A$, —$COR^B$, —$SO_2R^B$, —$CON(R^C)R^D$, —$CSN(R^C)R^D$, —$SO^2NHR^A$ or —$C(=NR^E)N(R^F)R^G$;

$R^5$, $R^6$, $R^A$, $R^C$ and $R^D$ independently represent a hydrogen atom, a $C_{1-6}$ alkyl group which may have any 1 to 5 substituents selected from the later identified substituent group β or any of the following substituents (xxix) to (xxxii) which may have any 1 to 3 substituents selected from the later identified substituent group α;

(xxix) a $C_{6-10}$ aryl group, (xxx) a heteroaryl group, (xxxi) a $C_{3-7}$ cycloalkyl group or (xxxii) a heterocycloalkyl group, or both of $Z^1$ and $R^5$ or both of $Z^2$ and $R^6$ bind together with the neighboring nitrogen atom to form an aliphatic cyclic amino group which may have any 1 to 3 substituents selected from the later identified substituent group α;

or $R^C$ and $R^D$ bind together with the neighboring nitrogen atom to form an aliphatic cyclic amino group which may have any 1 to 3 substituents selected from the later identified substituent group α;

$R^B$ represents a $C_{2-7}$ alkoxycarbonyl group, a $C_{1-6}$ alkylsulfonylamino group, a $C_{6-10}$ arylsulfonylamino group, a $C_{1-6}$ alkyl group which may have any 1 to 5 substituents selected from the later identified substituent group β or any of the following substituents (xxxiii) to (xxxvi) which may have any 1 to 3 substituents selected from the later identified substituent group α;

(xxxiii) a $C_{6-10}$ aryl group, (xxxiv) a heteroaryl group, (xxxv) a $C_{3-7}$ cycloalkyl group or (xxxvi) a heterocycloalkyl group, $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl($C_{2-7}$ alkoxycarbyl) group, a nitro group, a $C_{1-6}$ alkylsulfonyl group, a sulfamoyl group, a carbamimidoyl group or a $C_{1-6}$ alkyl group which may have any 1 to 5 substituents selected from the later identified substituent group β;

or $R^E$ and $R^F$ bind together to form an ethylene group;

or $R^F$ and $R^G$ bind together with the neighboring nitrogen atom to form an aliphatic cyclic amino group which may have a substituent selected from the later identified substituent group α;

Y represents CH or N;

Q represents —$C_{1-6}$ alkylene-, —$C_{2-6}$ alkenylene-, —$C_{2-6}$ alkynylene-, —$C_{1-6}$ alkylene-O—, —$C_{1-6}$ alkylene-S—, —O—$C_{1-6}$ alkylene-, —S—$C_{1-6}$ alkylene-, —$C_{1-6}$ alkylene-O—$C_{1-6}$ alkylene-, —$C_{1-6}$ alkylene-S—$C_{1-6}$ alkylene-, —CON($R^7$)—, —N($R^7$)CO—, —$C_{1-6}$ alkylene—CON($R^7$)— or —CON($R^7$) —$C_{1-6}$ alkylene-;

$R^7$ represents a hydrogen atom or a $C_{1-6}$ alkyl group;

ring A represents a $C_{6-10}$ aryl group or a heteroaryl group;

G represents a group represented by a formula:

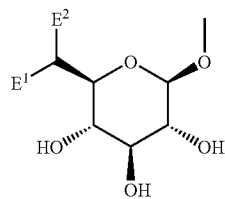

(G-1)

or a formula:

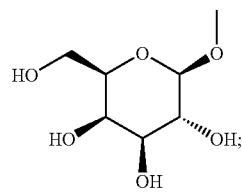

(G-2)

$E^1$ represents a hydrogen atom, a fluorine atom or a hydroxy group;

$E^2$ represents a hydrogen atom, a fluorine atom, a methyl group or a hydroxymethyl group;

substituent group α:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy)group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)]amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^H$)$R^I$ substituent group β:

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy($C_{1-6}$ alkoxy) group, a hydroxy($C_{1-6}$ alkylthio) group, an amino($C_{1-6}$ alkoxy) group, an amino($C_{1-6}$ alkylthio) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, —CON($R^H$)$R^I$, and any of the following substituents (xxxvii) to (xxxxviii) which may have any 1 to 3 substituents selected from the above substituent group α on the ring;

(xxxvii) a $C_{6-10}$ aryl group, (xxxviii) $C_{6-10}$ aryl-O—, (xxxix) a $C_{6-10}$ aryl($C_{1-6}$ alkoxy) group, (xxxx) a $C_{6-10}$ aryl($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloaryl-O—, (xxxxv) a heterocycloalkyl group, (xxxxvi) heterocycloaryl-O—, (xxxxvii) an aliphatic cyclic amino group or (xxxxviii) an aromatic cyclic amino group $R^H$ and $R^I$ independently represent a hydrogen atom or a $C_{1-6}$ alkyl group which may have any 1 to 3 substituents selected from the later identified substituent group γ;

or both of $R^H$ and $R^I$ bind together with the neighboring nitrogen atom to form an aliphatic cyclic amino group which may have any 1 to 3 substituents selected from the later identified substituent group δ;

substituent group γ:

a halogen atom, a hydroxy group, an amino group, a $C_{1-6}$ alkoxy group, a halo($C_{1-6}$ alkoxy) group, a hydroxy ($C_{1-6}$ alkoxy) group, an amino($C_{1-6}$ alkoxy) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy ($C_{1-6}$ alkyl)]sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group and —CON($R^J$)$R^K$ substituent group, δ:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)] amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di($C_{1-6}$ alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl)amino group, a $C_{1-6}$ alkyl group, a hydroxy($C_{1-6}$ alkyl) group, a $C_{2-7}$ alkoxycarbonyl group, a $C_{2-7}$ alkoxycarbonyl($C_{1-6}$ alkyl) group and a carbamoyl group, or a pharmaceutically acceptable salt thereof.

2. A nitrogen-containing fused-ring derivative as claimed in claim 1, wherein Q represents an ethylene group, or a pharmaceutically acceptable salt thereof.

3. A nitrogen-containing fused-ring derivative as claimed in claim 1, wherein Q represents a methylene group, or a pharmaceutically acceptable salt thereof.

4. A nitrogen-containing fused-ring derivative as claimed in claim 1, wherein G represents a group represented by the formula:

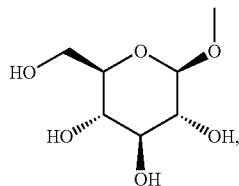

or a pharmaceutically acceptable salt thereof.

5. A nitrogen-containing fused-ring derivative as claimed in claim 1, wherein ring A represents a group derived from a benzene ring, a pyridine ring, a pyrimidine ring, a pyrazine ring or a pyridazine ring, or a pharmaceutically acceptable salt thereof.

6. A nitrogen-containing fused-ring derivative as claimed in claim 5, wherein the ring A represents a benzene ring, or a pharmaceutically acceptable salt thereof.

7. A nitrogen-containing fused-ring derivative as claimed in claim 5, wherein the ring A represents a pyridine ring, or a pharmaceutically acceptable salt thereof.

8. A nitrogen-containing fused-ring derivative as claimed in claim 5, wherein $R^3$ represents a hydrogen atom, a halogen atom or a $C_{1-6}$ alkyl group; $R^4$ represents a hydrogen atom, a hydroxy group, a halogen atom, a $C_{1-6}$ alkyl group, a $C_{1-6}$ alkoxy group, a $C_{1-6}$ alkylthio group, a hydroxy($C_{1-6}$ alkyl) group, a $C_{3-7}$ cycloalkyl group, or —$U^a$—$V^a$—$W^a$—N($R^{6a}$)-$Z^{2a}$-; $U^a$ represents —O— or a single bond and with the proviso that at least one of $V^a$ and $W^a$ does not represents a single bond when $U^a$ represents —O—; $V^a$ represents a $C_{1-6}$ alkylene group, a $C_{2-6}$ alkenylene group or a single bond; $W^a$ represents —CO— or a single bond; $Z^{2a}$ represents a hydrogen atom, —$R^{Aa}$, —CON($R^c$)$R^D$, or —C(=N$R^E$)N($R^F$)$R^G$; $R^{6a}$ and $R^{Aa}$ independently represent a hydrogen atom, or a $C_{1-6}$ alkyl group which may have any 1 to 5 groups selected from the later identified substituent group β; $R^C$ and $R^D$ independently represent a hydrogen atom, a $C_{1-6}$ alkyl group which may have any 1 to 5 groups selected from the later identified substituent group β, or any of the following substituents (xxix) to (xxxii) which may have any 1 to 3 substituents selected from the later identified substituent group α;

(xxix) a $C_{6-10}$ aryl group, (xxx) a heteroaryl group, (xxxi) a $C_{3-7}$ cycloalkyl group or (xxxii) a heterocycloalkyl group, or $R^C$ and $R^D$ bind together with the neighboring nitrogen atom to form an aliphatic cyclic amino group which may have any 1 to 3 substituents selected from the later identified substituent group α; $R^E$, $R^F$ and $R^G$ independently represent a hydrogen atom, a cyano group, a carbamoyl group, a $C_{2-7}$ acyl group, a $C_{2-7}$ alkoxycarbonyl group, a $C_{6-10}$ aryl($C_2$-7 alkoxycarbonyl) group, a nitro group, a $C_{1-6}$ alkylsulfonyl group, a sulfamoyl group, a carbamimidoyl group or a $C_{1-6}$ alkyl group which may have any 1 to 5 substituents selected from the later identified substituent group β; or $R^E$ and $R^F$ bind together to form an ethylene group; or $R^F$ and $R^G$ bind together with the neighboring nitrogen atom to form an aliphatic cyclic amino group which may have a substituent selected from the following substituent group α;

substituent group α:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy)group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl) group, an amino($C_{1-6}$ alkoxy) group, a mono or di($C_{1-6}$ alkyl)amino group, a mono or di[hydroxy($C_{1-6}$ alkyl)] amino group, a $C_{1-6}$ alkylsulfonyl group, a $C_{1-6}$ alkylsulfonylamino group, a $C_{1-6}$ alkylsulfonylamino ($C_{1-6}$ alkyl) group, a carboxy group, a $C_{2-7}$ alkoxycarbonyl group, a sulfamoyl group and —CON($R^H$)$R^I$ substituent group β:

a halogen atom, a hydroxy group, an amino group, a $C_{1-6}$ alkoxy group, a $C_{1-6}$ alkylthio group, a halo($C_{1-6}$ alkoxy) group, a halo($C_{1-6}$ alkylthio) group, a hydroxy ($C_{1-6}$ alkoxy) group, a hydroxy($C_{1-6}$ alkylthio) group, an amino($C_{1-6}$ alkoxy) group, an arnino($C_{1-6}$ alkylthio) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{1-6}$ alkyl)]ureido group, a mono or di($C_{1-6}$ alkyl)sulfamide group, a mono or di[hydroxy ($C_{1-6}$ alkyl)]-sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group, —CON($R^H$)$R^I$, and any of the following substituents (xxxvii) to (xxxxviii) which may have any 1 to 3 substituents selected from the above substituent group α on the ring;

(xxxvii) a $C_{6-10}$ aryl group, (xxxviii) $C_{6-10}$ aryl-O—, (xxxix) a $C_{6-10}$ aryl($C_{1-6}$ alkoxy) group, (xxxx) a $C_{6-10}$ aryl($C_{1-6}$ alkylthio) group, (xxxxi) a heteroaryl group, (xxxxii) heteroaryl-O—, (xxxxiii) a $C_{3-7}$ cycloalkyl group, (xxxxiv) $C_{3-7}$ cycloalkyl-O—, (xxxxv) a heterocycloalkyl group, (xxxxvi) heterocycloalkyl-O—, (xxxxvii) an aliphatic cyclic amino group or (xxxxviii) an aromatic cyclic amino group, $R^H$ and $R^I$ independently represent a hydrogen atom or a $C_{1-6}$ alkyl group which may have any 1 to 3 substituents selected from the later identified substituent group γ; or both of $R^H$ and $R^I$ bind together with the neighboring nitrogen atom to form an aliphatic cyclic amino group which may have any 1 to 3 substituents selected from the later identified substituent group δ;

substituent group γ:

a halogen atom, a hydroxy group, an amino group, a $C_{1-6}$ alkoxy group, a halo($C_{1-6}$ alkoxy) group, a hydroxy ($C_{1-6}$ alkoxy) group, an amino($C_{1-6}$ alkoxy) group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di[hydroxy($C_{I_6}$ alkyl)]ureido group, a mono or di($C_{1-6}$ alkyl)sulfamide group, a mono or di[hydroxy ($C_{1-6}$ alkyl)]sulfamide group, a $C_{2-7}$ acylamino group, an amino($C_{2-7}$ acylamino) group, a $C_{1-6}$ alkylsulfonyl group, a $C_{1-6}$ alkylsulfonylamino group, a carbamoyl ($C_{1-6}$ alkylsulfonylamino) group, a carboxy group, a $C_{2-7}$ alkoxycarbonyl group and —CON($R^J$)$R^K$ substituent group δ:

a halogen atom, a hydroxy group, an amino group, a $C_{1-6}$ alkyl group, a $C_{1-6}$ alkoxy group, a halo($C_{1-6}$ alkyl) group, a halo($C_{1-6}$ alkoxy) group, a hydroxy($C_{1-6}$ alkyl) group, a $C_{2-7}$ alkoxycarbonyl($C_{1-6}$ alkyl) group, a hydroxy($C_{1-6}$ alkoxy) group, an amino($C_{1-6}$ alkyl)

group, an amino($C_{1-6}$ alkoxy) group, a mono or di($C_{1-6}$ alkyl)amino group, a mono or di[hydroxy($C_{1-6}$ alkyl)] amino group, a $C_{1-6}$ alkylsulfonyl group, a $C_{1-6}$ alkylsulfonylamino group, a $C_{1-6}$ alkylsulfonylamino($C_{1-6}$ alkyl) group, a carboxy group, a $C_{2-7}$ alkoxycarbonyl group, a sulfamoyl group and —CON($R^J$)$R^K$ $R^J$ and $R^K$ independently represent a hydrogen atom or a $C_{1-6}$ alkyl group which may have any 1 to 3 substituents selected from a hydroxy group, an amino group, a mono or di($C_{1-6}$ alkyl)amino group, a $C_{2-7}$ alkoxycarbonyl group and a carbamoyl group;

or both of $R^J$ and $R^K$ bind together with the neighboring nitrogen atom to form an aliphatic cyclic amino group which may have any 1 to 3 substituents selected from a hydroxy group, an amino group, a mono or di($C_{1-6}$ alkyl)amino group, a $C_{1-6}$ alkyl group, a hydroxy($C_{1-6}$ alkyl) group, a $C_{2-7}$ alkoxycarbonyl group, a $C_{2-7}$ alkoxycarbonyl($C_{1-6}$ alkyl) group and a carbamoyl group, or a pharmaceutically acceptable salt thereof.

9. A nitrogen-containing fused-ring derivative as claimed in claim 5 or 8, wherein $R^1$ represents a hydrogen atom, a $C_{1-6}$ alkyl group, a hydroxy($C_{1-6}$ alkyl) group, or -$J^a$-$CONH_2$; $J^a$ represents a $C_{1-6}$ alkylene group; $R^2$ represents a hydrogen atom, or a pharmaceutically acceptable salt thereof.

10. A pharmaceutical composition comprising as an active ingredient a therapeutically effective amount of a nitro-containing fused-ring derivative as claimed in claim 1, or a pharmaceutically acceptable salt thereof.

11. A pharmaceutical composition as claimed in claim 10, wherein the dosage form is sustained release formulation.

* * * * *